United States Patent
Torgerson et al.

(10) Patent No.: US 9,987,493 B2
(45) Date of Patent: Jun. 5, 2018

(54) MEDICAL DEVICES AND METHODS FOR DELIVERY OF CURRENT-BASED ELECTRICAL STIMULATION THERAPY

(75) Inventors: Nathan A. Torgerson, Andover, MN (US); Matthew J. Michaels, St. Francis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1016 days.

(21) Appl. No.: 12/579,036

(22) Filed: Oct. 14, 2009

(65) Prior Publication Data
US 2010/0106231 A1    Apr. 29, 2010

Related U.S. Application Data

(60) Provisional application No. 61/109,032, filed on Oct. 28, 2008.

(51) Int. Cl.
*A61N 1/36* (2006.01)

(52) U.S. Cl.
CPC ..... *A61N 1/36185* (2013.01); *A61N 1/36082* (2013.01); *A61N 1/36125* (2013.01)

(58) Field of Classification Search
CPC ............ A61N 1/36125; A61N 1/36185; A61N 1/36157
USPC .......................................................... 607/2
See application file for complete search history.

(56) References Cited

U.S. PATENT DOCUMENTS

| | | |
|---|---|---|
| 4,532,930 A | 8/1985 | Crosby et al. |
| 4,592,359 A | 6/1986 | Galbraith |
| 4,686,987 A | 8/1987 | Salo et al. |
| 4,947,844 A | 8/1990 | McDermott |
| 5,387,228 A | 2/1995 | Shelton |
| 5,501,703 A | 3/1996 | Holsheimer et al. |
| 5,522,865 A | 6/1996 | Schulman et al. |
| 5,713,922 A | 2/1998 | King |
| 5,800,465 A | 9/1998 | Thompson et al. |
| 5,895,416 A | 4/1999 | Barreras, Sr. et al. |
| 5,941,906 A | 8/1999 | Barreras, Sr. et al. |

(Continued)

FOREIGN PATENT DOCUMENTS

| | | |
|---|---|---|
| WO | 9952588 A1 | 10/1999 |
| WO | 03090849 A1 | 11/2003 |
| WO | 2008049199 A1 | 5/2008 |

OTHER PUBLICATIONS

Jung et al., "Which programmable functions of pacemakers are available, and what is their clinical relevance?" Herz, Jun. 1991, vol. 16, No. 3, pp. 158-170.

(Continued)

*Primary Examiner* — William Levicky
(74) *Attorney, Agent, or Firm* — Shumaker & Sieffert, P.A.

(57) ABSTRACT

A medical electrical stimulator provides selective control of stimulation via a combination of two or more electrodes coupled to respective regulated current paths and one or more electrodes coupled to unregulated current paths. Constant current sources may control the current that is sourced or sunk via respective regulated current paths. An unregulated current path may sink or source current to and from an unregulated voltage source that serves as a reference voltage. Unregulated electrodes may function as unregulated anodes to source current from a reference voltage or unregulated cathodes to sink current to a reference voltage.

60 Claims, 25 Drawing Sheets

(56) References Cited

U.S. PATENT DOCUMENTS

| | | | |
|---|---|---|---|
| 6,002,966 | A | 12/1999 | Loeb et al. |
| 6,035,237 | A | 3/2000 | Schulman et al. |
| 6,181,969 | B1 | 1/2001 | Gord |
| 6,219,580 | B1 | 4/2001 | Faltys et al. |
| 6,301,500 | B1* | 10/2001 | Van Herk et al. .............. 607/2 |
| 6,516,227 | B1 | 2/2003 | Meadows et al. |
| 6,566,846 | B1 | 5/2003 | Voo |
| 6,609,032 | B1* | 8/2003 | Woods et al. .............. 607/46 |
| 6,690,974 | B2 | 2/2004 | Archer et al. |
| 6,799,070 | B2 | 9/2004 | Wolfe et al. |
| 6,895,280 | B2 | 5/2005 | Meadows et al. |
| 7,127,298 | B1 | 10/2006 | He et al. |
| 7,180,760 | B2 | 2/2007 | Varrichio et al. |
| 7,216,001 | B2 | 5/2007 | Hacker et al. |
| 7,251,529 | B2 | 7/2007 | Greenwood-Van Meerveld |
| 7,271,663 | B2 | 9/2007 | Baum et al. |
| 7,389,147 | B2 | 6/2008 | Wahlstrand et al. |
| 7,519,428 | B1 | 4/2009 | Palmer |
| 8,116,878 | B1 | 2/2012 | Palmer |
| 2001/0000187 | A1 | 4/2001 | Peckham et al. |
| 2003/0114899 | A1 | 6/2003 | Woods et al. |
| 2003/0120310 | A1 | 6/2003 | Mulhauser |
| 2003/0208244 | A1* | 11/2003 | Stein .............. A61N 1/37241 607/48 |
| 2005/0267546 | A1* | 12/2005 | Parramon et al. .............. 607/48 |
| 2007/0185551 | A1 | 8/2007 | Meadows et al. |
| 2007/0260169 | A1* | 11/2007 | Hause .............. 604/20 |
| 2008/0061630 | A1 | 3/2008 | Andreu et al. |

OTHER PUBLICATIONS

International Search Report and Written Opinion of international application No. PCT/US2009/061657, dated Mar. 15, 2010, 12 pp.
International Search Report and Written Opinion of international application No. PCT/US2009/061653, dated Apr. 1, 2010, 11 pp.
Säckinger et al., "A High-Swing, High-Impedance MOS Cascode Circuit," IEEE Journal of Solid-State Circuits, vol. 25, No. 1, Feb. 1990, pp. 289-298.
Patent Application Entitled "Adaptable Current Regulator for Delivery of Current-Based Electrical Stimulation Therapy," U.S. Appl. No. 12/579,220, filed Oct. 14, 2009.
Office Action for U.S. Appl. No. 12/579,220, dated May 31, 2011, 59 pages.
Response to office action for U.S. Appl. No. 12/579,220, filed Aug. 19, 2011, 37 pages.
Office action for U.S. Appl. No. 12/579,220, dated Oct. 28, 2011, 7 pages.
Response to office action and interview summary for U.S. Appl. No. 12/579,220, filed Jan. 30, 2012, 31 pages.
Final office action for U.S. Appl. No. 12/579,220, dated Apr. 13, 2012, 10 pages.
Response to office action for U.S. Appl. No. 12/579,220, filed Nov. 2, 2012, 9 pages.
Office action for U.S. Appl. No. 12/579,220, dated Aug. 2, 2012, 9 pages.
Response to final office action for U.S. Appl. No. 12/579,220, filed Apr. 29, 2013, 33 pages.
Final office action for U.S. Appl. No. 12/579,220, dated Jan. 29, 2013, 10 pages.
Office Action for U.S. Appl. No. 12/579,220, dated Oct. 4, 2013, 24 pp.
Response to Office Action dated Oct. 4, 2013, from U.S. Appl. No. 12/579,220, filed Jan. 6, 2014, 39 pp.
Office Action from U.S. Appl. No. 12/579,220, dated Apr. 18, 2014, 23 pp.
Response to Final Office Action dated Apr. 18, 2014, from U.S. Appl. No. 12/579,220, filed Jun. 18, 2014, 18 pp.
Notice of Appeal from U.S. Appl. No. 12/579,220, filed Jul. 18, 2014, 1 pp.
Pre-Appeal Brief Request for Review from U.S. Appl. No. 12/579,220, filed Jul. 18, 2014, 5 pp.
Response to European Office Action dated Jul. 24, 2014 from counterpart European Application No. 09744554.8, filed on Jan. 30, 2015, 9 pp.
Summons to attend oral proceedings pursuant to Rule 115(1) EPC from counterpart European Application No. 9744554.8, dated Jan. 27, 2017, 6 pp.
Examination Report from Counterpart European Patent Application No. 09744554.8, dated Jul. 24, 2014, 5 pp.
Notice of Allowance from U.S. Appl. No. 12/579,220, dated Feb. 13, 2015, 38 pp.
Response to Oral Proceedings Request including Main Request from European Patent Application No. 09744554.8, dated Jan. 27, 2017, filed May 12, 2017, 8 pp.
First Auxiliary from European Patent Application No. 09744554.8, filed May 12, 2017, 10 pp.
Second Auxiliary from European Patent Application No. 09744554.8, filed May 12, 2017, 11 pp.
Third Auxiliary from European Patent Application No. 09744554.8, filed May 12, 2017, 7 pp.
Modified Second Auxiliary from European Patent Application No. 09744554.8, filed Jun. 6, 2017, 12 pp.
Kim et al., "A 64-Site Multishank CMOS Low-Profile Neural Stimulating Probe," Journal of Solid-State Circuits, vol. 31, No. 9, Sep. 1996, 9 pp.
St-Amand et al., "Design and Optimization of a Low DC Offset CMOS Current-Source Dedicated to Implantable Miniaturized Stimulators," Analog Integrated Circuits and Signal Processing, Dec. 19, 1995, 15 pp.

* cited by examiner

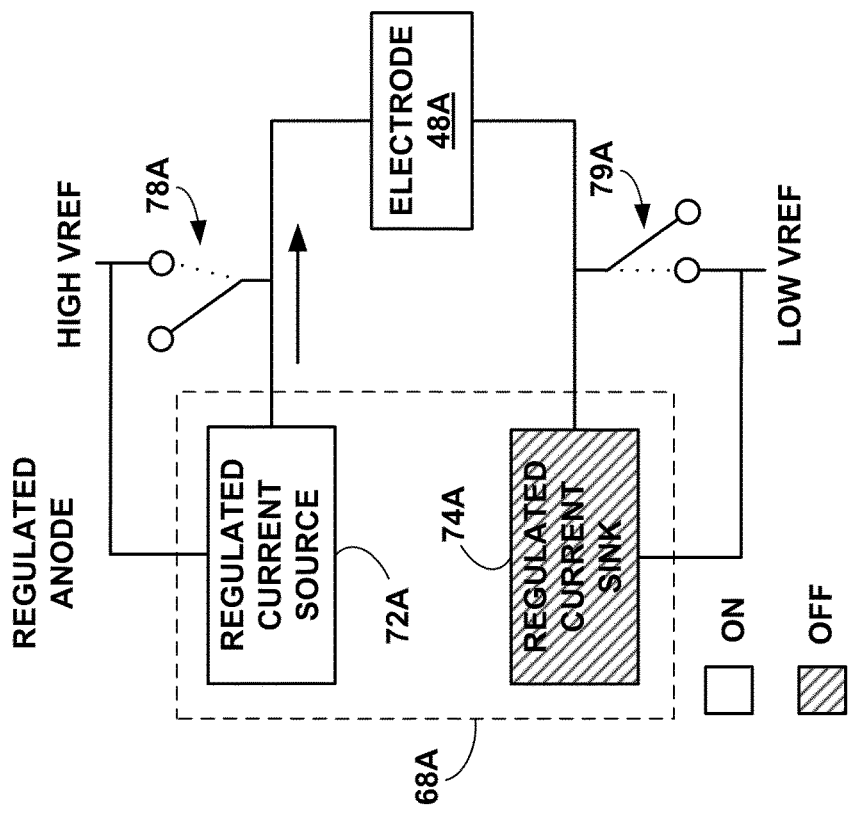
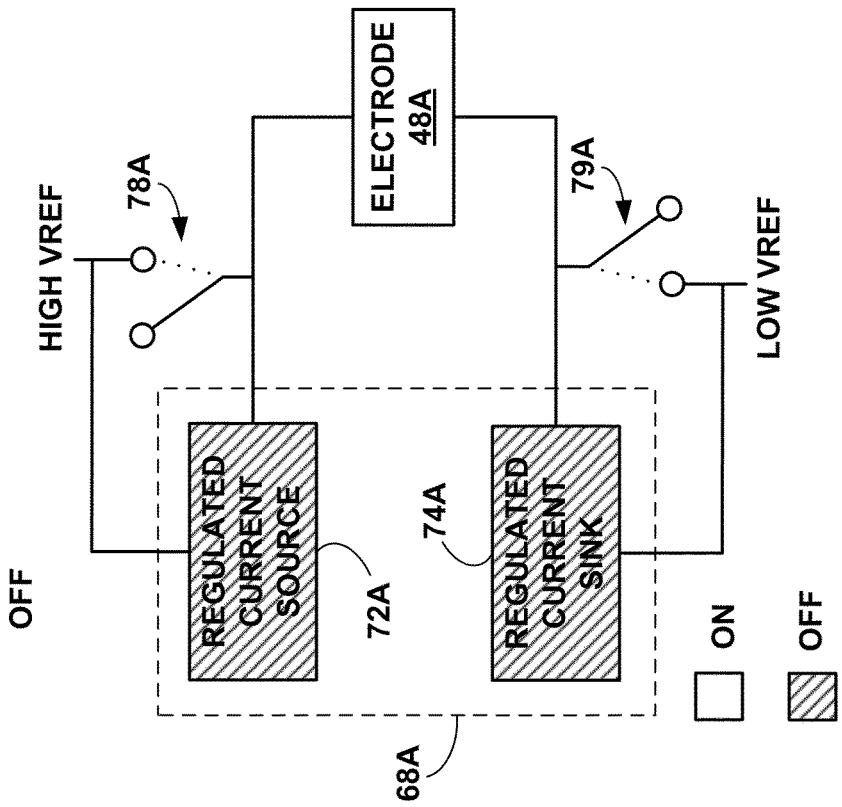

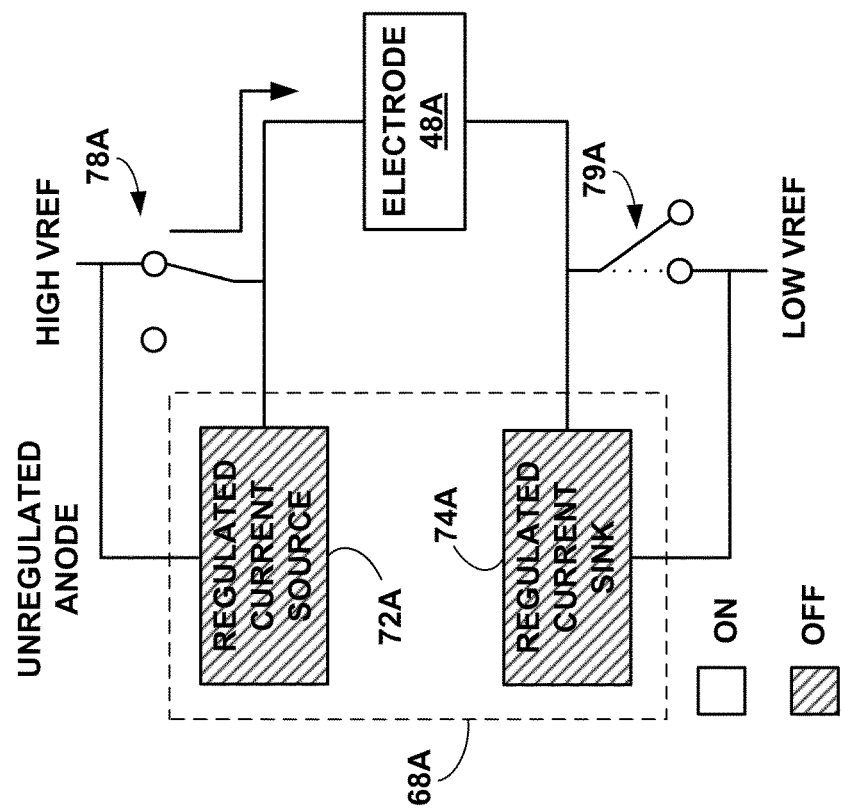
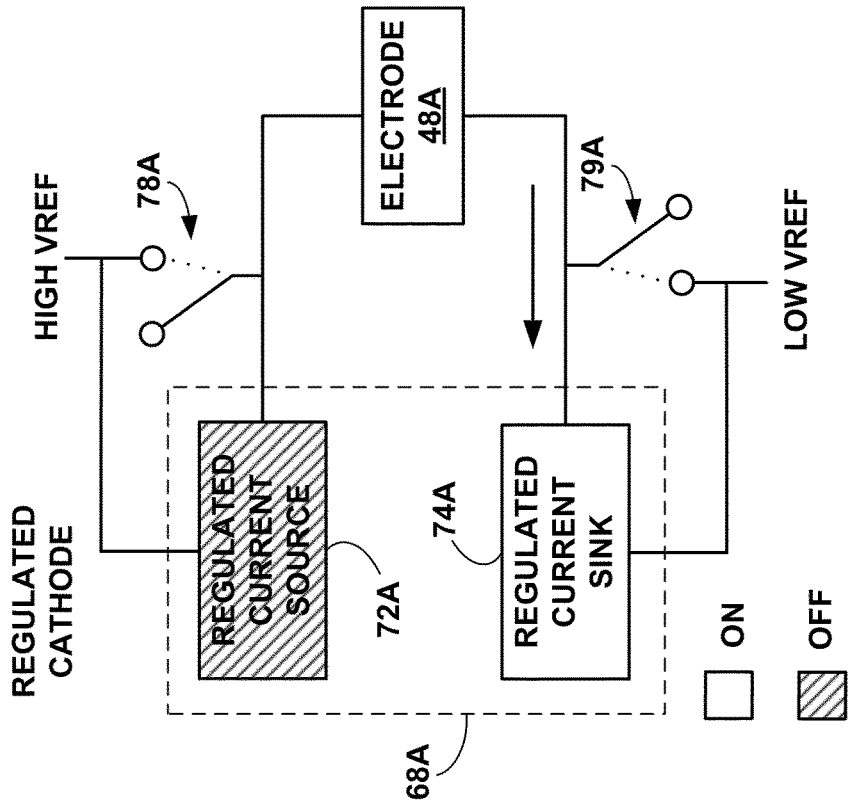

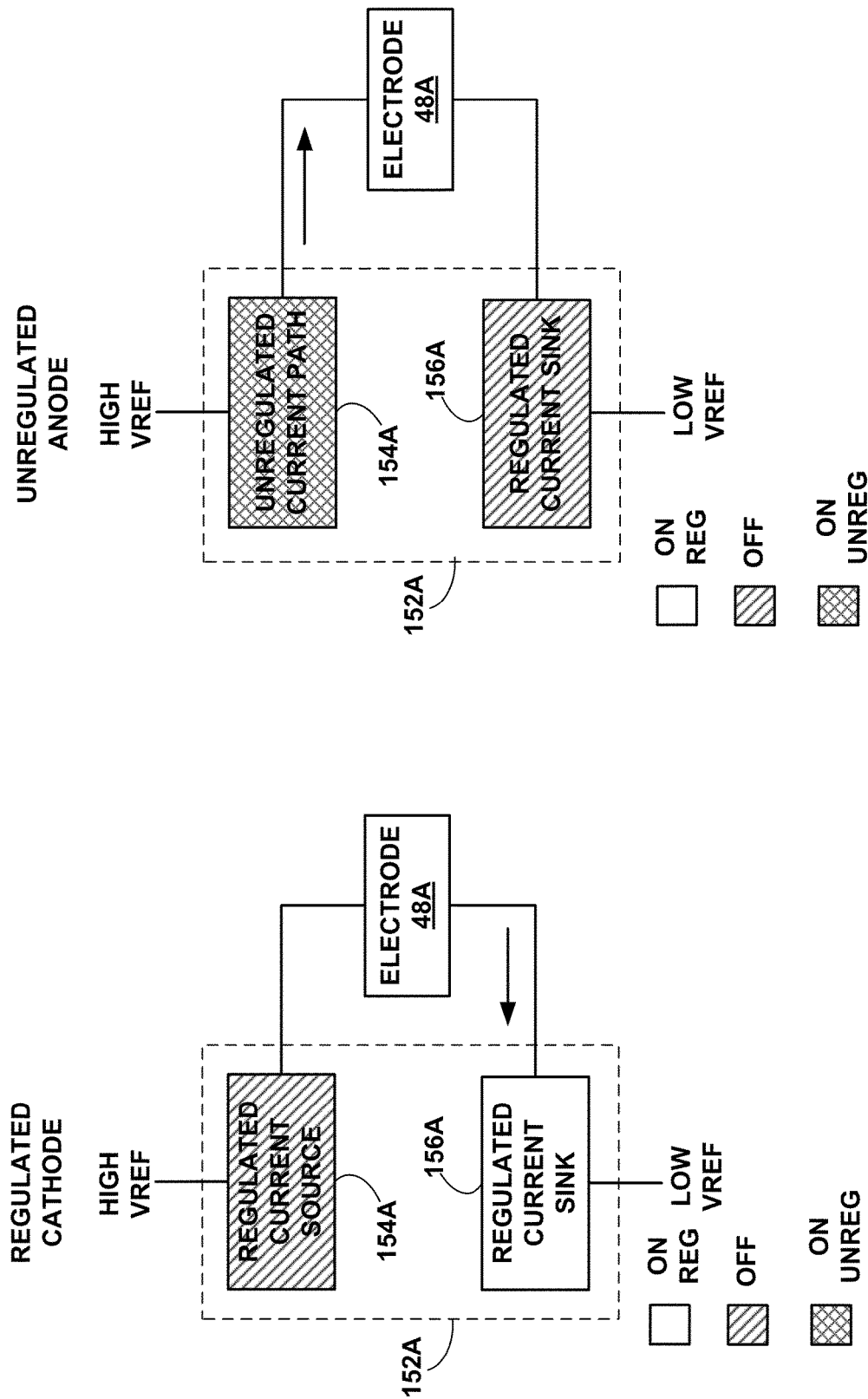

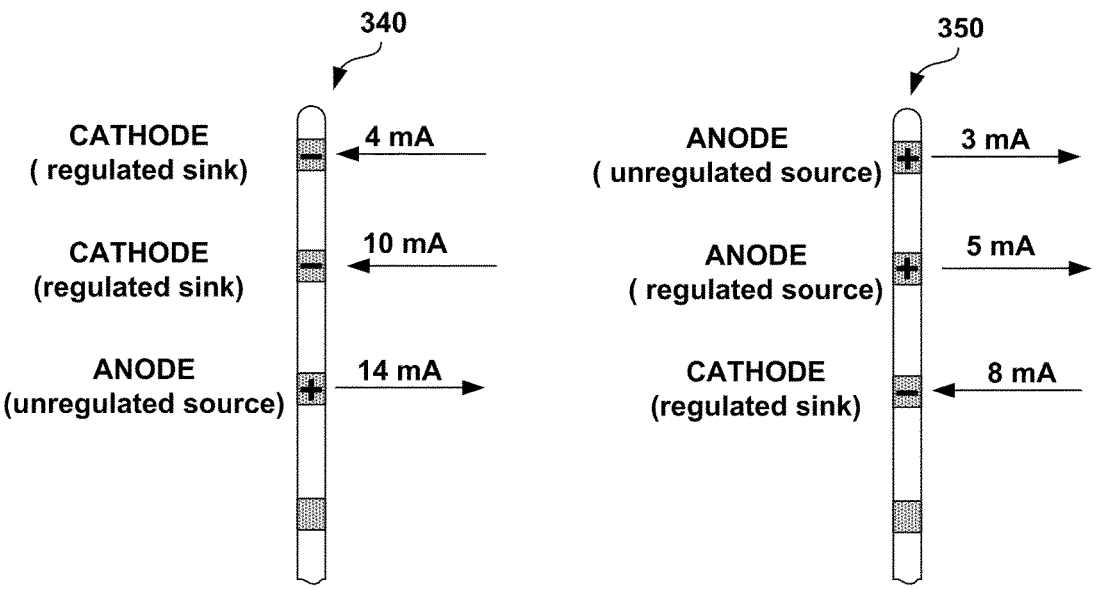
FIG. 18A  FIG. 18B
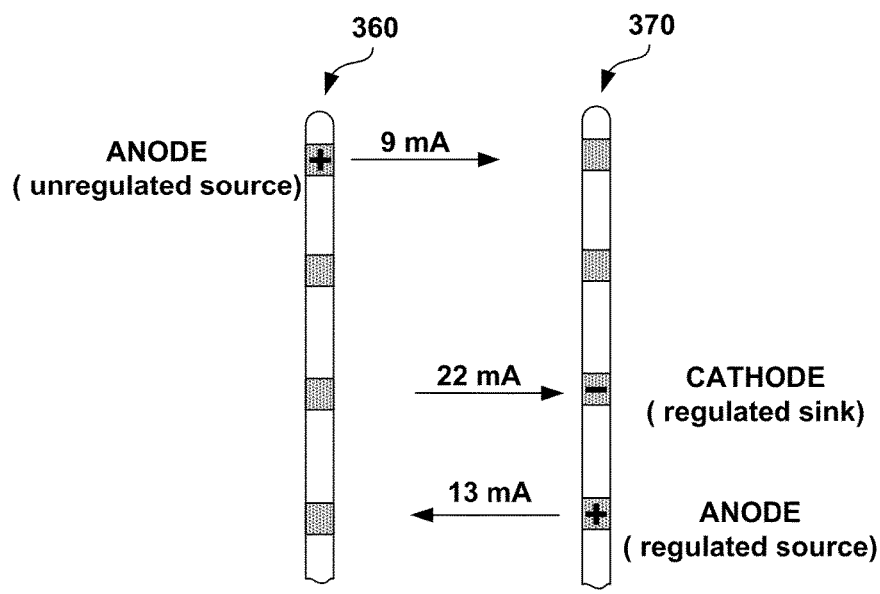
FIG. 18C

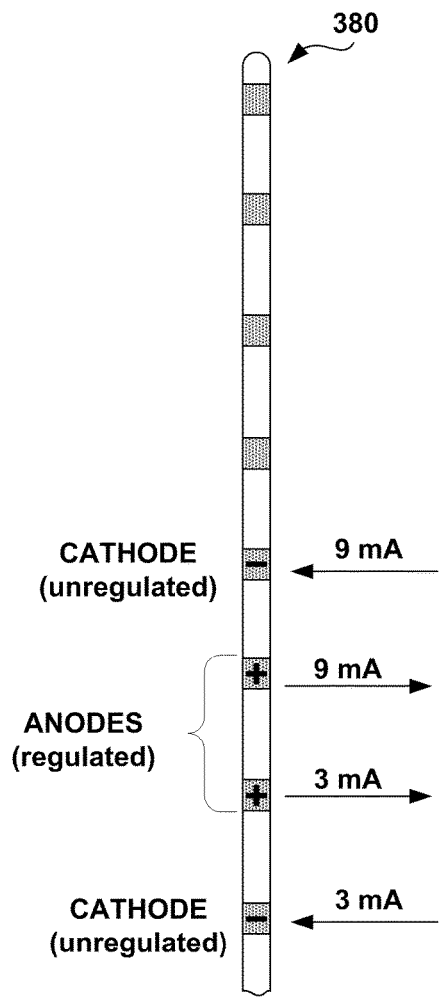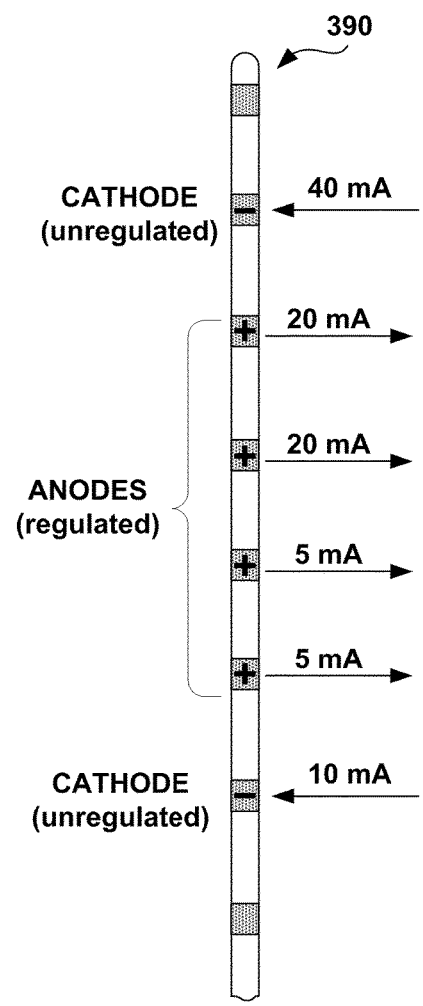
FIG. 19A      FIG. 19B
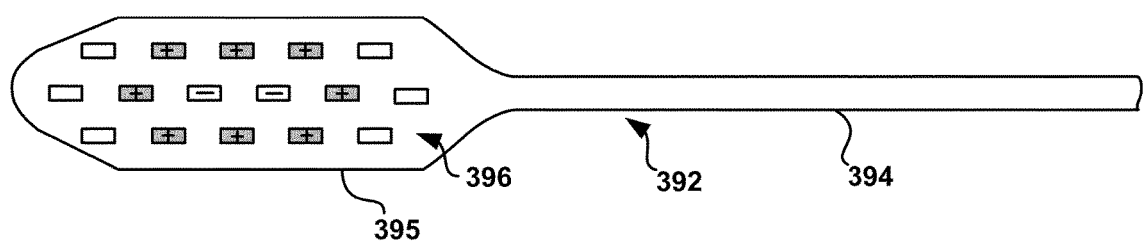
FIG. 19C

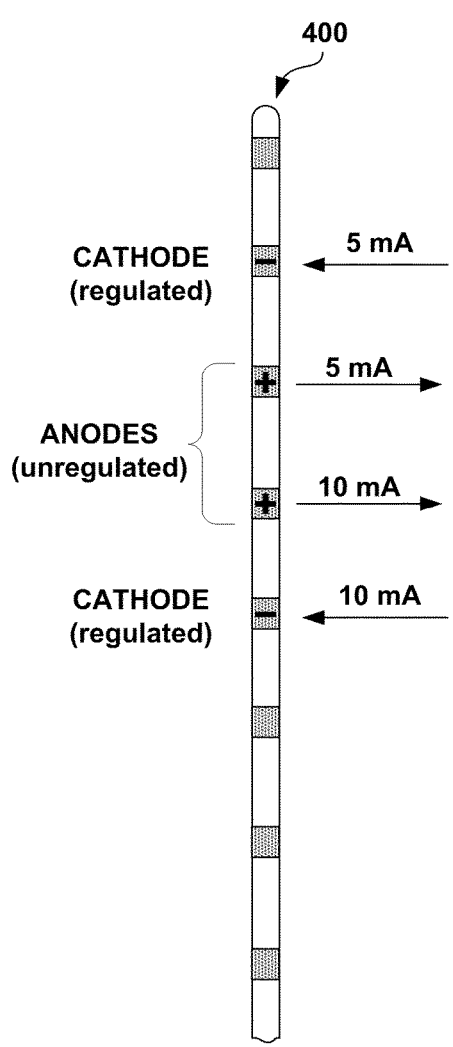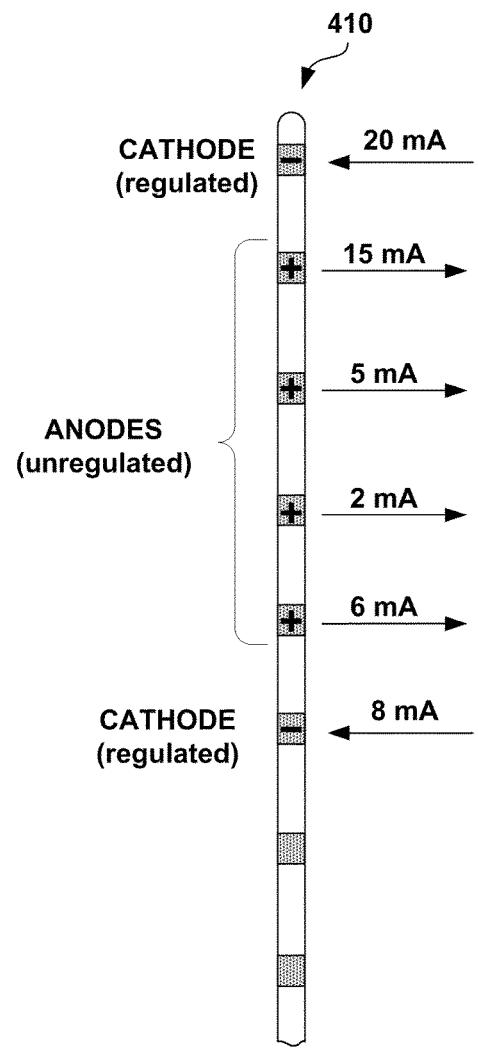
FIG. 20A   FIG. 20B
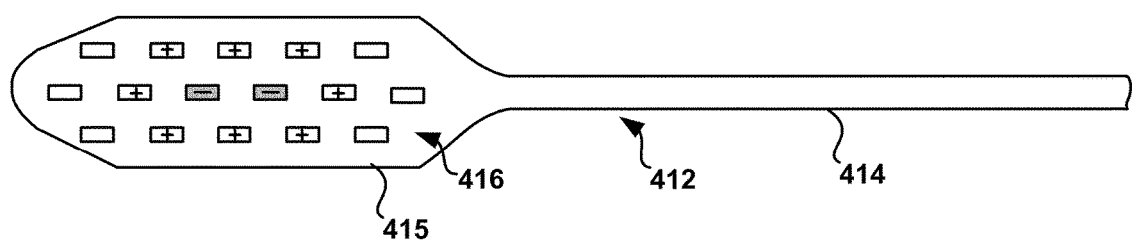
FIG. 20C

MEDICAL DEVICES AND METHODS FOR DELIVERY OF CURRENT-BASED ELECTRICAL STIMULATION THERAPY

This application claims the benefit of U.S. Provisional Application No. 61/109,032, entitled, "MEDICAL DEVICES AND METHODS FOR DELIVERY OF CURRENT-BASED ELECTRICAL STIMULATION THERAPY," and filed on Oct. 28, 2008, the entire contents of which being incorporated herein by reference.

TECHNICAL FIELD

The disclosure relates to medical devices and, more particularly, to medical devices that deliver electrical stimulation therapy.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

Medical electrical stimulators may be used to deliver electrical stimulation therapy to patients to relieve a variety of symptoms or conditions such as chronic pain, tremor, Parkinson's disease, depression, epilepsy, urinary or fecal incontinence, pelvic pain, sexual dysfunction, obesity, or gastroparesis. An electrical stimulator may be configured to deliver electrical stimulation therapy via leads that include electrodes implantable proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

A clinician selects values for a number of programmable stimulation parameters in order to define the electrical stimulation therapy to be delivered to a patient. For example, the clinician may select a current or voltage amplitude of the stimulation, and various characteristics of the stimulation waveform. In addition, the clinician may specify an electrode configuration used to deliver stimulation, including selected electrode combinations and electrode polarities. If the stimulation is delivered in the form of pulses, for example, the clinician may specify a pulse width and pulse rate. A set of parameter values may be referred to as a stimulation program. A program group may include multiple programs. Multiple programs in a program group may be delivered on a simultaneous, time-interleaved, or overlapping basis.

SUMMARY

In general, this disclosure describes techniques for delivery of electrical stimulation in the form of current-based waveforms via selected implantable electrodes associated within a medical electrical stimulation device. The techniques support selective control of stimulation via a combination of two or more electrodes coupled to regulated current paths and one or more electrodes coupled to unregulated current paths. An unregulated current path may serve to balance current that otherwise could be unbalanced between the regulated current paths. Regulated current sources or sinks can be programmed to be intentionally offset, with the difference in current being handled by the unregulated current path, either as a source or sink.

Regulated current sources may control the current that is sourced or sunk via respective regulated current paths. An unregulated current path may sink or source current to and from a voltage source that serves as a reference voltage. Electrodes that are coupled to source or sink stimulation current via regulated current paths may be referred to as regulated electrodes. Regulated electrodes may function as regulated anodes to source current or regulated cathodes to sink current. Electrodes that are coupled to source or sink stimulation current via unregulated current paths may be referred to as unregulated electrodes. Unregulated electrodes may function as unregulated anodes to source current from a reference voltage or unregulated cathodes to sink current to a reference voltage.

The amount of stimulation current sourced or sunk by the regulated electrodes may be programmed to be unbalanced. If two regulated electrodes are provided, for example, one regulated electrode may source more or less current than the other regulated electrode sinks. Alternatively, both electrodes could be configured as source electrodes (anodes) or as sink electrodes (cathodes). One or more unregulated electrodes may be selectively coupled to the reference voltage to source or sink, via the unregulated current path, approximately the sum of the regulated current produced by the regulated electrodes. An unregulated electrode may form a common anode or common cathode, for example, that sources or sinks, respectively, a sum of or difference between the currents produced by the regulated electrodes.

In some implementations, an electrode may be selectively configured to function as a regulated electrode or an unregulated electrode. For example, a current path coupled to an electrode may be adaptable to provide a regulated current path or an unregulated current path on a selective basis. In this case, an adaptable current regulator, such as an adaptable current source or sink, forms an adaptable current path that is adaptable to operate in a regulated or unregulated mode. In other implementations, a current regulator may be switchable to provide a regulated current path or an unregulated current path on a selective basis. In this case, a switch may couple an electrode to a regulated current path or an unregulated reference voltage on a selective basis to operate in a regulated or unregulated mode.

Using one or more unregulated electrodes, instead of regulated electrodes, may promote power efficiency, enhance current carrying capacity, simplify stimulation field configuration, and/or reduce complexity. Selective adaptation of a current source or sink to configure an electrode as a regulated electrode or unregulated electrode supports flexibility to provide precise current control or voltage compliance, as needed. In some implementations, an adaptable current source or sink may eliminate the need for a separate switch for unregulated operation, thereby avoiding increased size and complexity that may be associated with incorporation of such a switch.

In one example, the disclosure provides a method for delivering electrical stimulation therapy to a patient, the method comprising selectively coupling two or more of a plurality of electrodes implanted within the patient to respective regulated current paths to deliver electrical stimulation current to the patient, and selectively coupling at least another of the plurality of electrodes implanted within the patient to an unregulated current path to deliver the electrical stimulation current to the patient.

In another example, the disclosure provides a device for delivering electrical stimulation therapy to a patient, the device comprising a plurality of implantable electrodes, one or more regulated current paths, one or more unregulated current paths, a stimulation controller that selectively couples two or more of the electrodes to respective regulated current paths to deliver electrical stimulation current to the patient, and selectively couples at least another of the electrodes to one of the unregulated current paths to deliver the electrical stimulation electrical stimulation current to the patient.

In an additional example, the disclosure provides a device for programming a medical electrical stimulator to deliver electrical stimulation therapy to a patient, the device comprising a user interface configured to receive programming information from a user, a processor configured to define electrical stimulation programs based at least in part on the programming information, and a communication interface configured to communicate the programs to the medical electrical stimulator, wherein at least some of the electrical stimulation programs cause the medical electrical stimulator to generate electrical stimulation current for delivery to the patient via implantable electrodes, selectively couple two or more of the electrodes to respective regulated current paths, and selectively couple at least another of the electrodes to an unregulated current path to deliver the electrical stimulation current to the patient.

In another example, the disclosure is directed to a computer-readable storage medium comprising instructions that, when executed by a processor, cause the processor to selectively couple two or more of a plurality of electrodes implanted within the patient to respective regulated current paths to deliver electrical stimulation current to the patient, and selectively couple at least another of the plurality of electrodes implanted within the patient to an unregulated current path to deliver the electrical stimulation current to the patient.

In another example, the disclosure provides a method for delivering electrical stimulation therapy to a patient, the method comprising delivering electrical stimulation current via one of a plurality of implantable electrodes, and delivering electrical stimulation current via another of the plurality of implantable electrodes, wherein at least one of the electrodes delivering electrical stimulation current is coupled to an adaptable current regulator that operates as a regulated current path or an unregulated current path on a selective basis.

In a further example, the disclosure provides a device for delivering electrical stimulation therapy to a patient, the device comprising a plurality of implantable electrodes, and a plurality of adaptable current regulators that deliver electrical stimulation current via the electrodes, wherein each of the adaptable current regulators is configurable to operate as a regulated current path or an unregulated current path on a selective basis.

In another example, the disclosure provides a computer-readable storage medium comprising instructions that, when executed by a processor, cause the processor to deliver electrical stimulation current via one of a plurality of electrodes implanted within the patient and deliver electrical stimulation current via another of the plurality of electrodes implanted within the patient, wherein at least one of the electrodes delivering electrical stimulation current is coupled to an adaptable current regulator that operates as a regulated current path or an unregulated current path on a selective basis.

The details of one or more aspects of the disclosure are set forth in the accompanying drawings and the description below. Other features, objects, and advantages will be apparent from the description and drawings, and from the claims.

BRIEF DESCRIPTION OF DRAWINGS

FIGS. 7A-7D are block diagrams illustrating operation of example stimulation circuitry in producing different regulated and unregulated electrode configurations for use in the stimulation generator shown in FIGS. 5 and 6.

FIGS. 13A-13D are block diagrams illustrating operation of example stimulation circuitry in producing different regulated and unregulated electrode configurations for use in the stimulation generator of FIGS. 11 and 12.

FIGS. 17A-17C, 18A-18C, 19A-19C, and 20A-20C are conceptual diagrams illustrating example leads and electrode configurations that may be used for delivering electrical stimulation therapy as described in this disclosure.

DETAILED DESCRIPTION

Figure 1:
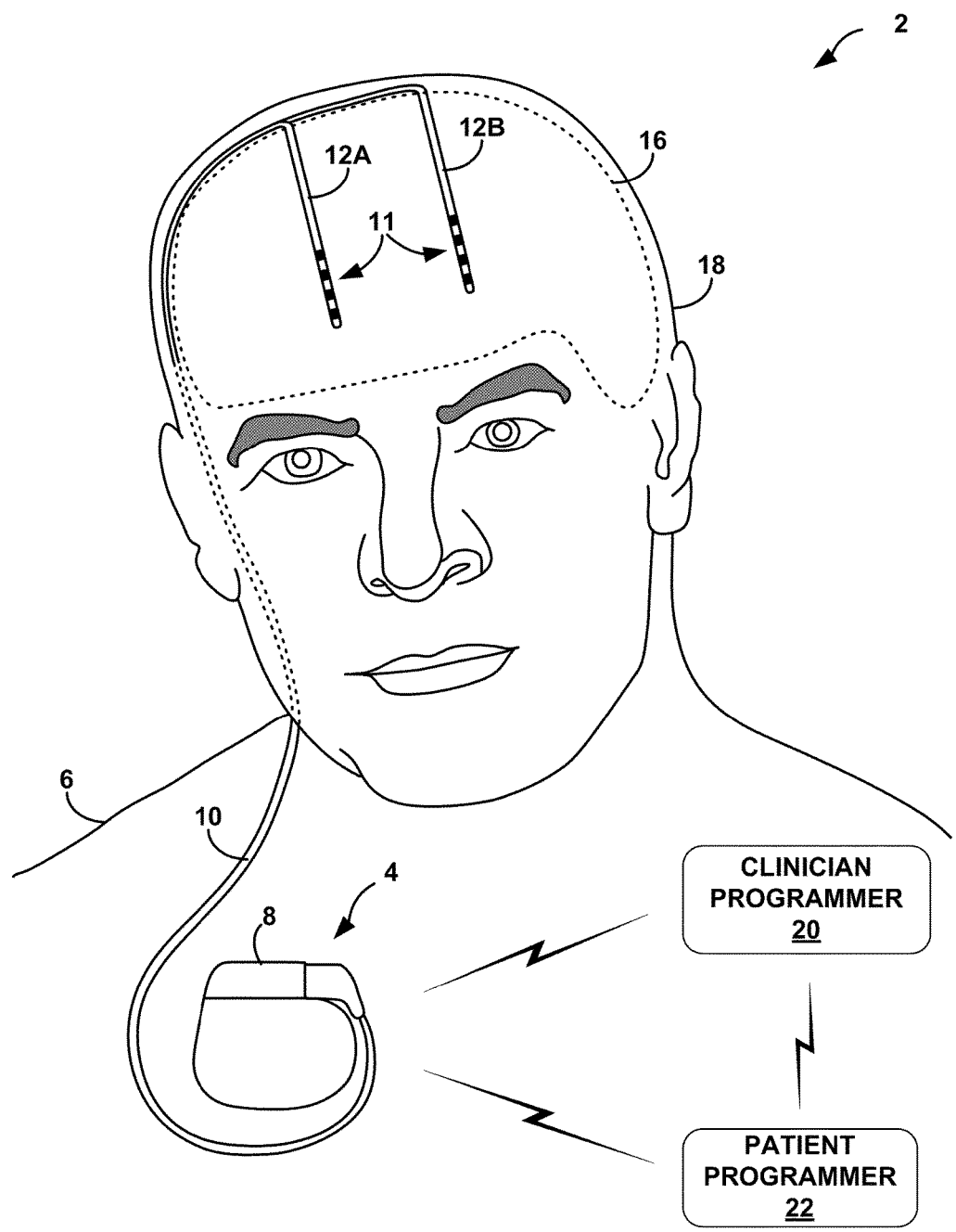
FIG. 1 is a conceptual diagram illustrating an example therapy system that includes an implantable stimulator coupled to a stimulation lead.

Balanced constant current may be delivered by a medical electrical stimulator using a combination of two or more regulated electrodes selectively coupled to regulated current paths and one or more unregulated electrodes selectively coupled to a reference voltage via unregulated current paths. Although the reference voltage may be regulated, the current delivered from the reference voltage may be unregulated. The regulated current paths may include bi-directional, regulated current sources that control the amounts of current delivered to or received from associated electrodes. The reference voltage, in various configurations, may be a high voltage supply rail, a low voltage supply rail, or a common ground.

A regulated current may generally refer to a current that is regulated or otherwise controlled to provide a substantially constant or controlled current level over a range of impedance load conditions. Hence, a current regulator may refer to a circuit that produces a regulated current, and a regulated current path may refer to a circuit path that includes or is coupled to a current regulator. An unregulated current may be an unregulated or uncontrolled current that may vary with different impedance load conditions. Hence, an unregulated current path may refer to a circuit path between a reference voltage source and a load that does not provide significant regulation of current sourced to or sunk from the load.

If the currents sourced and sunk by the regulated electrodes are balanced, the amount of charge received by an unregulated electrode may be small. If the regulated currents sourced and sunk by the regulated electrodes are programmed to be unbalanced, however, the unregulated electrode may source or sink the difference as unregulated current. Alternatively, the unregulated electrode may source or sink a sum of the regulated currents. The amount of current entering or leaving the unregulated, reference electrode is generally a function of the sum of or difference between the amounts of current source or sunk by the regulated current sources or sinks.

Hence, regulated current sources or sinks can be programmed to be intentionally offset, with the difference being handled by the unregulated current path. In other words, a regulated source and sink may be programmed such that the source current is greater than the sink current or vice versa. In either case, the unregulated current path handles the difference. In general, a source current may refer to a current that is driven out of an electrode, and a sink current may refer to a current that is received into an electrode. In some cases, a source current may be considered a positive current in the sense that it flows out of an electrode and a sink current may be considered a negative current in the sense that it flows into an electrode.

Regulated current stimulation, in the form of continuous waveforms or pulses, can be balanced by providing regulated current paths for each anode electrode and cathode electrode. However, regulated current paths may consume more power than unregulated current paths due to additional control and feedback circuitry typically associated with a regulated current sink or source. Hence, the use of regulated current paths for all electrodes may cause increased power consumption, which is generally undesirable in medical devices, such as implantable medical devices that are typically powered by limited battery resources.

The selective use of one or more unregulated electrodes as reference electrodes to source or sink current to and from the regulated electrodes may reduce power consumption. The unregulated electrodes source or sink an amount of stimulation current equal to approximately the sum of or difference between the stimulation current produced by the regulated electrodes. In this manner, the unregulated electrodes support delivery of balanced constant current stimulation waveforms. However, unregulated electrodes do not require operation of control and feedback circuitry associated with a regulated source or sink, and thereby support reduced power consumption.

In many cases, an unregulated reference electrode may be selected to be a cathode that sinks current to a reference voltage. Alternatively, in some cases, an unregulated reference electrode may be selected to be an anode that sources current from a reference voltage. Hence, the reference voltage may be a high voltage level or a low voltage level relative to output voltage levels used by regulated current sources or sinks. An electrode configuration defines a combination of selected electrodes and polarities for delivery of electrical stimulation. The electrode configuration may define combinations of one or more cathodes and one or more anodes.

In some implementations, if the unregulated electrode is a cathode and the electrode combination has more than one cathode, the unregulated electrode may be selected to be the cathode that sinks the greatest amount of current. In this manner, assuming similar electrode impedances, the reference voltage coupled to the unregulated cathode may be at the lowest potential relative to the potentials of other electrodes in the electrode combination. The regulated current sinks associated with the regulated electrodes then may use higher supply voltages that can be built up from the lower reference voltage associated with the unregulated cathode.

In other implementations, if the unregulated electrode is an anode and the electrode combination has more than one anode, the unregulated electrode may be selected to be the anode that sources the highest amount of current. In this manner, the regulated anode(s) can balance the current using voltage sources that are lower than the reference voltage to which the unregulated anode is selectively coupled. Whether the unregulated electrode is an anode or a cathode, the selective use of an unregulated reference voltage can reduce power consumption during operation of the electrical stimulator. In some examples, the unregulated anode that is selected to provide the unregulated current path need not source the highest amount of current. If the impedance of the unregulated anode is greater than the impedance of the regulated anode(s), for example, the unregulated anode may present a higher potential than the regulated anodes, even though a lower current may be applied via the unregulated anode. Hence, in order to gain efficiency, the unregulated anode may be selected as the anode that presents the highest potential, as a function of the anode impedance and the current level that will be sourced by the unregulated anode, in order to reduce the difference between the highest and lowest potentials needed to produce the desired current output.

All or some of the electrodes in an electrode array may be configured to function as either a regulated electrode or an unregulated electrode on a selective basis. For example, an adaptable current regulator selectively coupled to an electrode may provide an adaptable current source or sink that is adaptable to selectively provide either a regulated current path or an unregulated current path. If the electrode is selected to be an unregulated anode or cathode, for example, current source or sink circuitry associated with the electrode may be selectively configured to disable current regulation and thereby operate in an unregulated mode. This implementation may be referred to as an adaptable current source.

Alternatively, an electrode may be selectively switched between a regulated current source or sink and a low or high reference voltage, respectively. For example, a switch may selectively couple the electrode to the current source or sink to provide a regulated current path, or to a reference voltage to provide an unregulated current path. If the electrode is selected to be an unregulated anode or cathode, for example, the switch may, in effect, bypass the regulated current source or sink circuitry, and couple the electrode to the reference voltage. This implementation may be referred to as a switchable current source.

An adaptable or switchable current source may be configured, in some implementations, to incorporate an active cascode configuration to control an amount of electrical stimulation current coupled to the electrodes. Transistors arranged in an active cascode configuration may control output transistors associated with an adaptable or switchable current source. The active cascode configuration may promote stability throughout a wider operating range of an adaptable or switchable current source.

Using one or more unregulated electrodes, instead of regulated electrodes, on a selective basis may promote power efficiency, enhance current carrying capacity, simplify stimulation field configuration, and/or reduce complexity. Selective adaptation of a current source or sink to configure an electrode as a regulated electrode or unregulated electrode supports flexibility to provide precise current control or voltage compliance, as needed. In some implementations, an adaptable current source or sink may eliminate the need for a separate switch for unregulated operation, thereby avoiding increased size, complexity and cost that may be associated with incorporation of such a switch.

FIG. 1 is a conceptual diagram illustrating an example system 2 that may be used to deliver stimulation therapy to patient 6. Patient 14 ordinarily, but not necessarily, will be a human. Generally, therapy system 2 includes implantable stimulator 4 that delivers an electrical stimulation to patient 6 via one or more implantable electrodes (not shown). The implantable electrodes may be deployed on one or more implantable medical leads, such as implantable medical lead 10. The electrical stimulation may be in the form of constant current pulses or substantially continuous waveforms. Various parameters of the pulses or waveforms may be defined by a stimulation program. The pulses or waveforms may be delivered substantially continuously or in bursts, segments, or patterns, and may be delivered alone or in combination with pulses or waveforms defined by one or more other stimulation programs. Although FIG. 1 shows a fully implantable stimulator 4, techniques described in this disclosure may be applied to external stimulators having electrodes deployed via percutaneously implantable leads. One or more of the electrodes may be located on a housing, i.e., "can," of the implantable stimulator 4. In addition, in some cases, implantable electrodes may be deployed on a leadless stimulator.

In the example illustrated in FIG. 1, implantable stimulator 4 is implanted within a subcutaneous pocket in a clavicle region of patient 6. Stimulator 4 generates programmable electrical stimulation, e.g., a current waveform or current pulses, and delivers the stimulation via an implantable medical lead 10 carrying an array of implantable stimulation electrodes 11. In some cases, multiple implantable leads may be provided. In the example of FIG. 1, a distal end of lead 10 is bifurcated and includes two lead segments 12A and 12B (collectively "lead segments 12"). Lead segments 12A and 12B each include a set of electrodes forming part of the array of electrodes 11. In various examples, lead segments 12A and 12B may each carry four, eight, or sixteen electrodes. In FIG. 1, each lead segment 12A, 12B carries four electrodes, configured as ring electrodes at different axial positions near the distal ends of the lead segments.

In some examples, lead 10 may also carry one or more sense electrodes to permit implantable stimulator 4 to sense electrical signals from patient 6. Some of the stimulation electrodes may be coupled to function as stimulation electrodes and sense electrodes on a selective basis. In other examples, implantable stimulator may be coupled to one or more leads which may or may not be bifurcated. In such examples, the leads may be coupled to implantable stimulator 4 via a common lead extension or via separate lead extensions. In addition, implantable stimulator 4 may, in some examples, include one or more electrodes on the housing in addition to the electrodes on lead segments 12.

A proximal end of lead 10 may be both electrically and mechanically coupled to a header 8 on implantable stimulator 4 either directly or indirectly via a lead extension. Conductors in the lead body may electrically connect stimulation electrodes located on lead segments 12 to implantable stimulator 4. Lead 10 traverses from the implant site of implantable stimulator 4 along the neck of patient 6 to cranium 18 of patient 6 to access brain 16. Lead segments 12A and 12B are implanted within the right and left hemispheres, respectively, in order to deliver electrical stimulation to one more regions of brain 16, which may be selected based on the patient condition or disorder.

Implantable stimulator 4 may deliver, for example, deep brain stimulation (DBS) or cortical stimulation (CS) therapy to patient 6 via the electrodes carried by, i.e., located on, lead segments 12 to treat any of a variety of neurological disorders or diseases. Example neurological disorders may include depression, dementia, obsessive-compulsive disorder and movement disorders, such as Parkinson's disease, spasticity, epilepsy, and dystonia. DBS also may be useful for treating other patient conditions, such as migraines and obesity. However, the disclosure is not limited to the configuration of lead 10 shown in FIG. 1, or to the delivery of DBS or CS therapy.

Lead segments 12A, 12B may be implanted within a desired location of brain 16 through respective holes in cranium 18. Lead segments 12A, 12B may be placed at any location within brain 16 such that the electrodes located on lead segments 12A, 12B are capable of providing electrical stimulation to targeted tissue during treatment. Example locations for lead segments 12A, 12B within brain 26 may include the pedunculopontine nucleus (PPN), thalamus, basal ganglia structures (e.g., globus pallidus, substantia nigra, subthalmic nucleus), zona inserta, fiber tracts, lenticular fasciculus (and branches thereof), ansa lenticularis, and/or the Field of Forel (thalamic fasciculus). In the case of migraines, lead segments 12 may be implanted to provide stimulation to the visual cortex of brain 16 in order to reduce or eliminate migraine headaches afflicting patient 6. However, the target therapy delivery site may depend upon the patient condition or disorder being treated.

The electrodes of lead segments 12A, 12B are shown as ring electrodes. Ring electrodes are commonly used in DBS applications because they are simple to program and are capable of delivering an electrical field to any tissue adjacent to lead segments 12A, 12B. In other implementations, the electrodes of lead segments 12A, 12B may have different configurations. For examples, the electrodes of lead segments 12A, 12B may have a complex electrode array geometry that is capable of producing shaped electrical fields. The complex electrode array geometry may include multiple electrodes (e.g., partial ring or segmented electrodes) around the perimeter of each lead segments 12A, 12B, rather than one ring electrode. In this manner, electrical stimulation may be directed in a specific direction from lead segments 12 to enhance therapy efficacy and reduce possible adverse side effects from stimulating a large volume of tissue. In alternative examples, lead segments 12 may have shapes other than elongated cylinders as shown in FIG. 1. For example, lead segments 12 may be paddle leads, spherical leads, bendable leads, or any other type of shape effective in treating patient 6.

Therapy system 2 also may include a clinician programmer 20 and/or a patient programmer 22. Clinician programmer 20 may be a handheld computing device that permits a clinician to program stimulation therapy for patient 6 via a user interface, e.g., using input keys and a display. For example, using clinician programmer 20, the clinician may specify stimulation parameters, i.e., create programs, for use in delivery of stimulation therapy. Clinician programmer 20 may support telemetry (e.g., radio frequency (RF) telemetry) with implantable stimulator 4 to download programs and, optionally, upload operational or physiological data stored by implantable stimulator 4. In this manner, the clinician may periodically interrogate implantable stimulator 4 to evaluate efficacy and, if necessary, modify the programs or create new programs. In some examples, clinician programmer 20 transmits programs to patient programmer 22 in addition to or instead of implantable stimulator 4.

Like clinician programmer 20, patient programmer 22 may be a handheld computing device. Patient programmer 22 may also include a display and input keys to allow patient 6 to interact with patient programmer 22 and implantable stimulator 4. In this manner, patient programmer 22 provides patient 6 with a user interface for control of the stimulation therapy delivered by implantable stimulator 4. For example, patient 6 may use patient programmer 22 to start, stop or adjust electrical stimulation therapy. In particular, patient programmer 22 may permit patient 6 to adjust stimulation parameters of a program such as duration, current or voltage amplitude, pulse width and pulse rate. Patient 6 may also select a program, e.g., from among a plurality of stored programs, as the present program to control delivery of stimulation by implantable stimulator 4.

In some examples, implantable stimulator 4 delivers stimulation according to a group of programs at a given time. Each program of such a program group may include respective values for each of a plurality of therapy parameters, such as respective values for each of current amplitude, pulse width, pulse rate and electrode configuration. Implantable stimulator 4 may interleave pulses or other signals according to the different programs of a program group, e.g., cycle through the programs, to simultaneously treat different symptoms or different body regions, or provide a combined therapeutic effect. In such examples, clinician programmer 20 may be used to create programs, and assemble the programs into program groups. Patient programmer 22 may be used to adjust stimulation parameters of one or more programs of a program group, and select a program group, e.g., from among a plurality of stored program groups, as the current program group to control delivery of stimulation by implantable stimulator 4.

Implantable stimulator 4, clinician programmer 20, and patient programmer 22 may communicate via cables or a wireless communication, as shown in FIG. 1. Clinician programmer 20 and patient programmer 22 may, for example, communicate via wireless communication with implantable stimulator 4 using RF telemetry techniques known in the art. Clinician programmer 20 and patient programmer 22 also may communicate with each other using any of a variety of local wireless communication techniques, such as RF communication according to the 802.11 or Bluetooth specification sets, infrared communication, e.g., according to the IrDA standard, or other standard or proprietary telemetry protocols. Each of clinician programmer 20 and patient programmer 22 may include a transceiver to permit bi-directional communication with implantable stimulator 4.

Generally, system 2 delivers stimulation therapy to patient 6 in the form of constant current waveforms or constant current pulses. The shapes of the pulses may vary according to different design objectives. Implantable stimulator 4 regulates current that is sourced or sunk by one or more electrodes, referred to as regulated electrodes, and selectively couples one or more additional electrodes to an unregulated reference voltage, such as a high or low voltage supply rail or a common reference voltage. The one or more electrodes coupled to the unregulated reference voltage may be referred to as "common electrodes" or "reference electrodes." The reference electrode may be used to source or sink current so that charge is balanced across the regulated and unregulated electrodes.

Again, a source current may refer to a positive current that flows out of an electrode, e.g., from a regulated current source via a regulated current path to surrounding tissue, or from a reference voltage via an unregulated current path. A sink current may refer to a negative current that flows into an electrode, e.g. from surrounding tissue and is sunk by a regulated current sink via a regulated current path or by a reference voltage via an unregulated current path. Regulated source currents may sum to produce a greater overall source current. Regulated sink currents may sum to produce a greater overall sink current. Regulated source and regulated sink currents may partially or entirely cancel one another, producing a net difference in the form of a net source current or sink current. An unregulated current path can source or sink current approximately equal to this net difference.

As described in this disclosure, an unregulated, reference electrode may sink or source unregulated current to counterbalance any unbalanced current produced by the regulated electrodes, such as a sum of regulated source currents, a sum of regulated sink currents, or a difference between regulated source and sink currents. In particular, the unregulated, reference electrode may counter-balance the unbalanced current by sinking or sourcing counter-balancing current to or from the reference voltage via an unregulated current path. The unregulated current path may be a direct connection provided by a simple switch.

An unregulated, reference electrode that is selectively coupled to sink current to a low reference voltage may be referred to as an unregulated cathode. An unregulated, reference electrode that is selectively coupled to source current from a high reference voltage may be referred to as an unregulated anode. The high or low reference voltage may be voltage-regulated but not current-regulated. Consequently, the unregulated anode or cathode is coupled to the reference voltage via an unregulated current path. Typically, constant current stimulation therapies regulate current at each stimulation electrode so that there is a balance in charge between the stimulation electrodes. However, the use of regulated current paths for all electrodes may cause increased power consumption, which is generally undesirable in medical devices, such as implantable medical devices that are typically powered by limited battery resources.

Stimulator 4 may be configured to reduce power consumption by reducing the number of electrodes coupled to regulated current sources or sinks, and thereby reducing the amount of regulator overhead required to produce a stimulation waveform. In particular, by coupling an electrode to a reference voltage via an unregulated current path, stimulator 4 can reduce the power consumption overhead otherwise associated with control and feedback circuitry in a regulated current source or sink. Implantable stimulator 4 may be configured to provide selective control of electrodes so that each electrode may be programmed to provide a regulated current source, a regulated current sink, an unregulated current source, or an unregulated current sink.

For a given electrode configuration, stimulator 4 may be programmed such that one or more electrodes operate as either regulated current sources or regulated current sinks, while one or more other electrodes operate as either unregulated current sources or unregulated current sinks. In particular, regulated current sources and sinks may be programmed such that the regulated current is not balanced between the regulated current sources and regulated current sinks. For example, the amount of source current flowing from regulated electrodes may be different from the amount of sink current flowing to regulated electrodes. In this case, the current may be balanced by an unregulated, reference electrode. The unregulated, reference electrode is coupled to a reference voltage via an unregulated current path to either source or sink excess current to or from the unbalanced, regulated electrodes.

The unregulated reference electrode may be selected to be either a cathode that sinks current to a reference voltage, or an anode that sources current from a reference voltage, depending on the programming of the regulated electrodes. The regulated and unregulated electrodes form an electrode configuration. The electrode configuration may be programmed using a programmer, such as clinician programmer 20 or patient programmer 22. In programming the electrode configuration, the user, e.g., physician, technician, or patient, may specify a particular electrode configuration by, for example, selecting particular electrodes and assigning source and sink currents to the selected electrodes, as well as other parameters for a stimulation program. The system, however, operates on limited battery resources and, as such, has headroom restrictions that affect the practical operation of the system.

For this reason, in example electrode configurations having an unregulated cathode and a regulated cathode, the cathode that sinks the greatest amount of current in the specified electrode configuration may be selected as the unregulated cathode during the programming process. The unregulated cathode may then be coupled to a reference voltage having the lowest potential relative to the potentials of other electrodes in the electrode configuration. This allows the regulated cathode to use voltage built up from the low reference voltage. In some examples, the unregulated cathode that is selected to provide the unregulated current path need not sink the highest amount of current. If the impedance of the unregulated cathode is greater than the impedance of the regulated cathode(s), for example, the unregulated cathode may present a lower potential than the regulated cathodes, even though a lower current may be applied via the unregulated cathode. Hence, in order to gain efficiency, the unregulated cathode may be selected as the cathode that presents the lowest potential, as a function of the cathode impedance and the current level that will be sunk by the unregulated cathode, in order to reduce the difference between the highest and lowest potentials needed to produce the desired current output.

Similarly, in example electrode configurations having an unregulated anode and a regulated anode, the unregulated anode may be selected to be the anode that sources the least amount of current in the specified electrode configuration. The regulated anode(s) in the electrode configuration can balance the current using voltage sources that are lower than the reference voltage to which the unregulated anode is coupled. Throughout this description, the terms current sink and cathode may be used interchangeably. Similarly, the terms current source and anode may be used interchangeably. Additionally, it is generally assumed for the examples provided throughout this description that there is sufficient headroom to support the specified electrode configuration. That is, it is generally assumed that the voltage rails are sufficiently separated to support the specified current paths, and that the unregulated cathodes and/or anodes do not pull the common mode of the system too far to the top or bottom rail such that the regulated current paths cannot support the programmed current.

In an example configuration, an electrode configuration may be programmed to include two or more regulated current sources (regulated anodes) and an unregulated current sink (unregulated cathode). In another example, an electrode combination may be programmed to include one or more regulated current sources (regulated anode), one or more regulated current sinks (regulated cathodes), and an unregulated current sink (unregulated cathode).

In an additional example, an electrode combination may be programmed to include two or more regulated current sinks (regulated cathodes) and an unregulated current source (unregulated anode). In another example implementation, an electrode combination may be programmed to include one or more regulated current sources (regulated anodes), one or more regulated current sinks (regulated cathodes), and an unregulated current source (unregulated anode).

In a further example, an electrode combination may be programmed to include two or more regulated current sources (regulated anodes) and two or more unregulated current sinks (unregulated cathodes). The regulated current sources (regulated anodes), e.g., two to four regulated anodes, may be positioned substantially adjacent to each other and be surrounded by two or more electrodes programmed as unregulated current sinks (unregulated cathodes). This electrode configuration may be referred to as a common cathode ring configuration. In the common cathode ring configuration, the current sourced by each of the regulated anodes may be adjusted to steer the stimulation field, without the need to adjust the unregulated cathodes.

In another example, an electrode combination may be programmed to include two or more regulated current sinks (regulated cathodes) and two or more unregulated current sources (unregulated anodes). The regulated current sinks (regulated cathodes), e.g., two to four regulated cathodes, may be positioned substantially adjacent to each other and be surrounded by two or more electrodes programmed as unregulated current sources (unregulated anodes). This electrode configuration may be referred to as a common anode ring configuration. In the common cathode ring configuration, the current sunk by each of the regulated cathodes may be adjusted to steer the stimulation field, without the need to adjust the unregulated anodes.

In yet another example, an electrode combination may be programmed to include two or more unregulated current sources (unregulated anodes) and two or more regulated current sinks (regulated cathodes). The unregulated current sources (common anodes), e.g., two to four common anodes, may be positioned approximately adjacent to each other and be surrounded by the regulated cathodes. This electrode configuration may be referred to as a common anode pool configuration. In the common anode pool configuration, the stimulation area may be controlled by adjusting the regulated cathodes, without the need to adjust the unregulated anodes.

In another example, an electrode combination may be programmed to include two or more unregulated current sinks (unregulated cathodes) and two or more regulated current sources (regulated anodes). The unregulated current sinks (common cathodes), e.g., two to four common cathodes, may be positioned approximately adjacent to each other and be surrounded by the regulated anodes. This electrode configuration may be referred to as a common cathode pool configuration. In the common cathode pool configuration, the stimulation area may be controlled by adjusting the regulated anodes, without the need to adjust the unregulated cathodes.

Implantable stimulator 4 may provide one or more advantages. As an example, implantable stimulator 4 may increase battery life by reducing the number of electrodes that are required to be current regulated. Increased battery life may be achieved because current regulator circuitry can be turned OFF for electrodes operating as unregulated current sources or sinks. In this manner, the power consumption overhead associated with at least some of the regulated current sources or sinks can be reduced or eliminated.

In addition, the use of an unregulated, reference electrode may reduce the number of electrodes required for stimulation, and increase current carrying capacity. As an illustration, it is assumed that regulator circuitry may limit a regulated cathode or anode to source or sink approximately 35 mA of current. If there was a single cathode sinking 35 mA, two anodes would be restricted to 17.5 mA each. The use of an unregulated current source or sink may permit the sourcing or sinking of more than 35 mA of current in this illustration.

For example, two separate, regulated anodes could be selectively programmed to source 35 mA each, and an unregulated cathode selective coupled to a reference voltage via an unregulated current path could sink 70 mA of current from the anodes. Thus, an unregulated current source or sink may be used in place of two or more regulated current sources or current sinks, and thereby increase current carrying capacity without requiring activation of additional electrodes. In addition, with one or more unregulated electrodes, a reduced number of electrodes for a desired stimulation field may simplify programming of electrode configurations.

Implantable stimulator 4 may also simplify programming by allowing reprogramming of regulated stimulation electrodes without the need for reprogramming of unregulated, reference electrodes. For example, an electrode combination including two regulated current sources and an unregulated current sink may initially be programmed to source particular amounts of current via each regulated stimulation electrode. The amount of current sourced or sunk by each regulated electrode may be changed without requiring the unregulated, reference electrode to be reprogrammed. In particular, there is no need to specify a particular amount of current to be sunk by the unregulated, reference electrode.

Unlike a regulated electrode coupled to a regulated current path, the unregulated electrode is coupled to a reference voltage via an unregulated current path and, in general, will source or sink whatever amount of current is needed. In other words, for the unregulated electrode, there is no need to program a particular current level for a regulated current sink, as would be required for a regulated electrode. Instead, the unregulated electrode is passive and simply directs current to and from a reference voltage depending on whether a positive, source current or a negative, sink current is need to counterbalance the regulated current. In this manner, the unregulated, reference electrode may sink whatever amount of current is needed given the reprogramming of the regulated electrodes, thereby balancing the current distribution when the regulated electrodes are programmed to produce an unbalanced current distribution, e.g., when two regulated electrodes produce different amounts of sink and source current, when two regulated electrodes both produce sink current or both produce source current, or in other more complex scenarios in which three or more regulated electrodes produce imbalanced current distributions.

Similarly, if the unregulated electrode is operating as an anode in conjunction with two or more regulated cathodes, the cathodes can be reprogrammed to sink different amounts of current without the need to reprogram the unregulated anode. Instead, the unregulated anode will simply source, from the reference voltage via the unregulated current path, whatever current is required by the regulated cathodes. Accordingly, the use of one or more unregulated anodes or cathodes in an electrode configuration can contribute to reduction in programming complexity.

Notably, a given electrode need not be dedicated to operation as an unregulated, reference electrode. Rather, some or all of the electrodes in an electrode array may be used as an unregulated electrode on a selective basis. For example, an electrode may be selectively configured as an unregulated electrode by a switch that bypasses a regulated current source or sink otherwise associated with the electrode and couples the electrode to the reference voltage. Alternatively, a regulated current source or sink associated with an electrode may be adaptable to provide an adaptable current path that selectively couples the electrode to the reference voltage via an unregulated current path, e.g., like a switch.

In addition, the ability to have more than one common anode may allow the use of a common anode ring, common cathode ring, common anode pool, or common cathode pool configurations, as described above, or other electrode configurations. Again, such electrode configurations may be programmed to steer stimulation currents and shape stimulation fields by programming current levels for regulated electrodes without the need for programming of unregulated electrodes. In each case, the use of an unregulated electrode in combination with one or more regulated electrodes may reduce programming complexity, promote programming flexibility, enhance current carrying capacity, and/or reduce power consumption ordinarily caused by current regulator overhead.

In one example, implantable stimulator 4 includes an array of bidirectional current regulators and an array of switches. The bidirectional regulated current sources may be selectively configured to source or sink current, and may be coupled to respective, selected electrodes. In particular, each electrode may be selectively coupled to one of the bidirectional regulated current sources to sink or source current via a regulated current path, or to an unregulated reference voltage via an unregulated current path by a corresponding one of the switches. An implantable stimulator implemented in accordance with this example embodiment may be referred to as a switchable implantable stimulator. In particular, electrodes may be selectively switched to couple to regulated current sources that source or sink regulated current or to a reference voltage that sources or sinks unregulated current.

In another example, implantable stimulator 4 includes an array of adaptable stimulation circuits. Each of the adaptable stimulation circuits is coupled to one of the electrodes and may be operated as a regulated current source or sink, or as a switch that couples the corresponding electrode to an unregulated reference voltage. In this manner, each adaptable stimulation circuit provides an adaptable current path that is configurable to operate as either a regulated current path or an unregulated current path on a selective basis. An implantable stimulator implemented in accordance with this example embodiment may be referred to as an adaptable implantable stimulator. An adaptable implantable stimulator may be smaller in size than a switchable implantable stimulator. Because chip footprints may provide limited available real estate to accommodate additional circuitry, such as additional switches, it may be desirable to use an adaptable implantable stimulator that does not require a switch and instead makes use of an adaptable current source or sink.

In an additional example, implantable stimulator 4 may be implemented as a switchable or an adaptable implantable stimulator that uses an active cascode configuration for controlling the amount of current coupled to the electrodes. With respect to the switchable implantable stimulator, output transistors for the regulated current sources and regulated current sinks may be controlled by a plurality of transistors arranged in an active cascode configuration. With respect to the adaptable implantable stimulator, output transistors for the adaptable current sources and sinks may be controlled by a plurality of transistors arranged in an active cascode configuration. An active cascode configuration may promote stability throughout a wider operating range of an adaptable or switchable current source.

Figure 2:
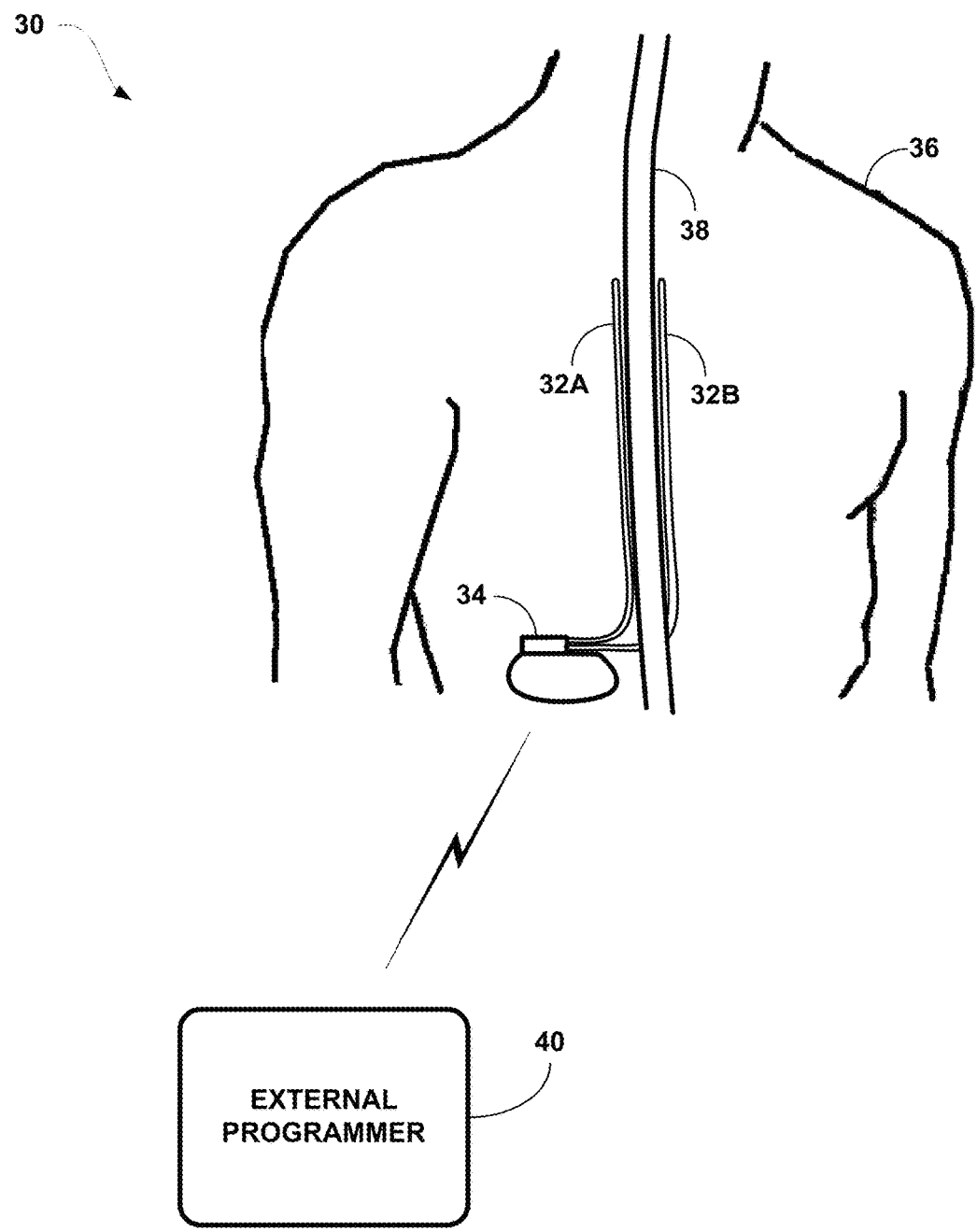
FIG. 2 is a conceptual diagram illustrating another example therapy system that includes an implantable stimulator coupled to a stimulation lead.

FIG. 2 is a conceptual diagram illustrating system 30 that delivers stimulation therapy to spinal cord 38 of patient 36. Hence, like FIG. 1, FIG. 2 represents another example of an electrical stimulation system that may support techniques described in this disclosure. Other electrical stimulation systems may be configured to deliver electrical stimulation to gastrointestinal organs, pelvic nerves or muscle, peripheral nerves, or other stimulation sites. In the example of FIG. 2, system 30 delivers stimulation therapy from implantable stimulator 34 to spinal cord 38 via one or more electrodes (not shown) carried by, i.e., located on, implantable medical leads 32A and 32B (collectively "leads 32"). System 30 and, more particularly, implantable stimulator 34 may operate in a manner similar to implantable stimulator 4 (FIG. 1). That is, implantable stimulator 34 delivers constant current stimulation pulses or waveforms to patient 36 via one or more regulated, stimulation electrodes and one or more unregulated, reference electrodes. In typical implementations, two or more regulated electrodes may be used in conjunction with one or more unregulated electrodes.

In the example of FIG. 2, the distal ends of leads 32 carry electrodes that are placed adjacent to the target tissue of spinal cord 38. The proximal ends of leads 32 may be both electrically and mechanically coupled to implantable stimulator 4 either directly or indirectly via a lead extension and header. Alternatively, in some examples, leads 32 may be implanted and coupled to an external stimulator, e.g., through a percutaneous port. In additional example implementations, stimulator 34 may be a leadless stimulator with one or more arrays of electrodes arranged on a housing of the stimulator rather than leads that extend from the housing. Application of certain techniques will be described herein with respect to implantable stimulator 34 and implantable leads 32 having ring electrodes for purposes of illustration. However, other types of electrodes may be used.

Stimulator 34 may be implanted in patient 36 at a location minimally noticeable to the patient. Alternatively, stimulator 34 may be external with percutaneously implanted leads. For SCS, stimulator 34 may be located in the lower abdomen, lower back, or other location to secure the stimulator. Leads 32 are tunneled from stimulator 34 through tissue to reach the target tissue adjacent to spinal cord 38 for stimulation delivery. At the distal ends of leads 32 are one or more electrodes (not shown) that transfer the stimulation pulses from the lead to the tissue. The electrodes may be electrode pads on a paddle lead, circular (i.e., ring) electrodes surrounding the body of leads 32, conformable electrodes, cuff electrodes, segmented electrodes, or any other type of electrodes capable of forming unipolar, bipolar or multi-polar electrode configurations.

Implantable stimulator 34 delivers stimulation to spinal cord 38 to reduce the amount of pain perceived by patient 36. As mentioned above, however, the stimulator may be used with a variety of different therapies, such as peripheral nerve stimulation (PNS), peripheral nerve field stimulation (PNFS), deep brain stimulation (DBS), cortical stimulation (CS), pelvic floor stimulation, peripheral nerve stimulation, gastric stimulation, and the like. The stimulation delivered by implantable stimulator 34 may take the form of stimulation pulses or continuous stimulation waveforms, and may be characterized by controlled current levels, as well as programmed pulse widths and pulse rates in the case of stimulation current pulses. Stimulation may be delivered via selected combinations of electrodes located on one or both of leads 32. Stimulation of spinal cord 38 may, for example, prevent pain signals from traveling through the spinal cord and to the brain of the patient. Patient 34 perceives the interruption of pain signals as a reduction in pain and, therefore, efficacious therapy.

With reference to FIG. 2, a user, such as a clinician or patient 36, may interact with a user interface of external programmer 40 to program stimulator 34. Programming of stimulator 34 may refer generally to the generation and transfer of commands, programs, or other information to control the operation of the stimulator. For example, programmer 40 may transmit programs, parameter adjustments, program selections, group selections, or other information to control the operation of stimulator 34, e.g., by wireless telemetry. As one example, programmer 40 may transmit parameter adjustments to support parameter-directed shifting of electrode combinations used to deliver stimulation according to a selected program.

In some cases, external programmer 40 may be characterized as a physician or clinician programmer, such as clinician programmer 20 (FIG. 1), if it is primarily intended for use by a physician or clinician. In other cases, external programmer 40 may be characterized as a patient programmer, such as patient programmer 22 (FIG. 1), if it is primarily intended for use by a patient. In general, a physician or clinician programmer may support selection and generation of programs by a clinician for use by stimulator 34, whereas a patient programmer may support adjustment and selection of such programs by a patient during ordinary use.

Whether programmer 40 is configured for clinician or patient use, programmer 40 may communicate to implantable stimulator 4 or any other computing device via wireless communication. Programmer 40, for example, may communicate via wireless communication with implantable stimulator 4 using radio frequency (RF) telemetry techniques known in the art. Programmer 40 may also communicate with another programmer or computing device via a wired or wireless connection using any of a variety of local wireless communication techniques, such as RF communication according to the 802.11 or Bluetooth specification sets, infrared communication according to the IRDA specification set, or other standard or proprietary telemetry protocols. Programmer 40 may also communicate with another programming or computing device via exchange of removable media, such as magnetic or optical disks, or memory cards or sticks. Further, programmer 40 may communicate with implantable stimulator 4 and other programming devices via remote telemetry techniques known in the art, communicating via a local area network (LAN), wide area network (WAN), public switched telephone network (PSTN), or cellular telephone network, for example.

Figure 3:
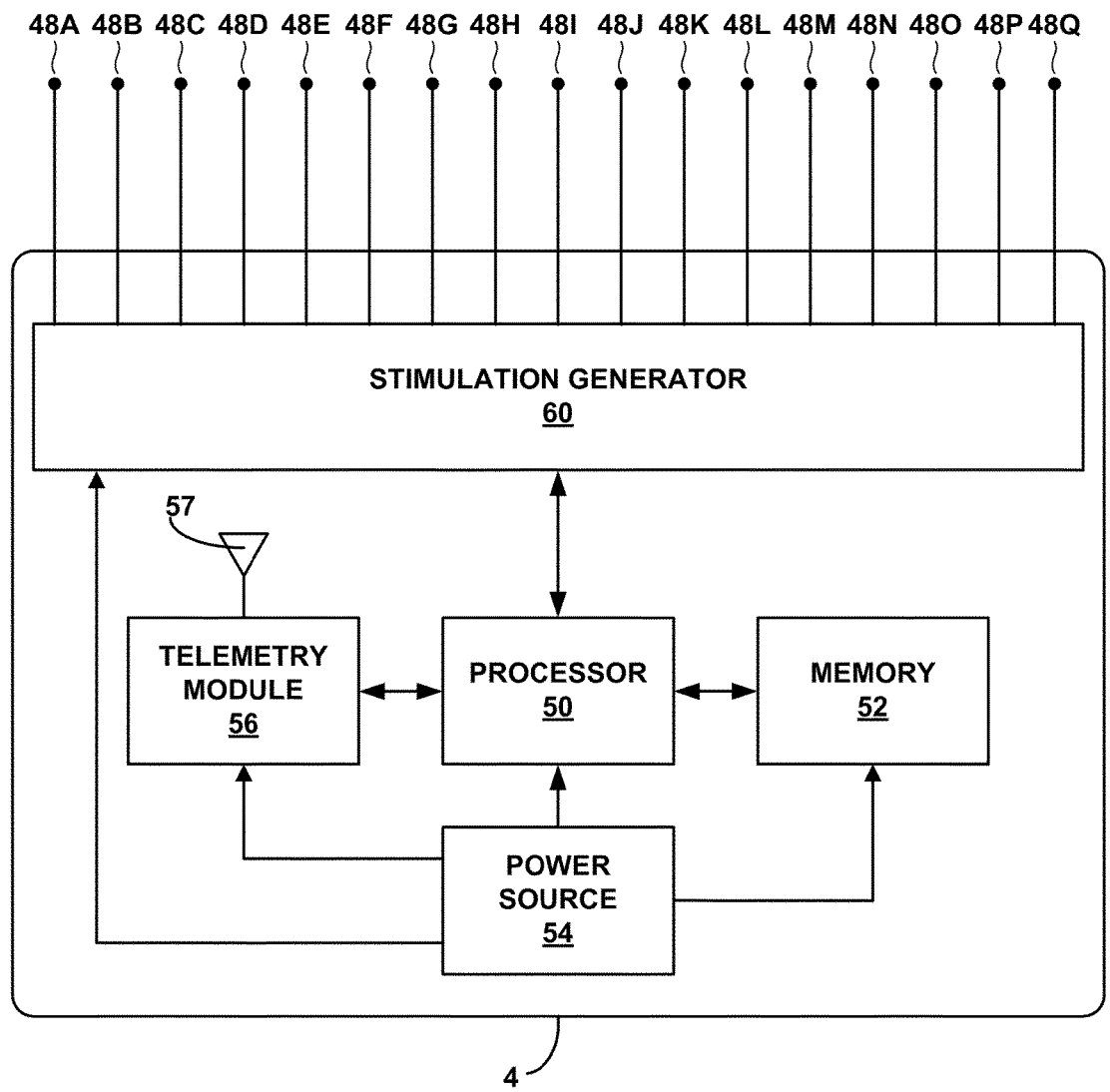
FIG. 3 is a block diagram illustrating various example components of an implantable electrical stimulator.

FIG. 3 is a block diagram illustrating various components of an example implantable stimulator 4. Although the components shown in FIG. 3 are described in reference to implantable stimulator 4, the components may also be included within implantable stimulator 34 shown in FIG. 2 and used within system 30. In the example of FIG. 3, implantable stimulator 4 includes processor 50, memory 52, power source 54, telemetry module 56, antenna 57, and a stimulation generator 60. Implantable stimulator 4 is also shown in FIG. 3 coupled to electrodes 48A-Q (collectively "electrodes 48"). Electrodes 48A-48P are implantable and may be deployed on one or more implantable leads. With respect to FIG. 1, lead segments 12A and 12B may carry electrodes 48A-H and electrodes 48I-P, respectively. In some cases, one or more additional electrodes may be located on or within the housing of implantable stimulator 4, e.g., to provide a common or ground electrode. With respect to FIG. 2, leads 32A and 32B may carry electrodes 48A-H and electrodes 48I-P, respectively. In the examples of FIGS. 1 and 2, a lead or lead segment carries eight electrodes to provide an 2×8 electrode configuration (two leads with 8 electrodes each), providing a total of sixteen different electrodes. The leads may be detachable from a housing associated with implantable stimulator 4, or be fixed to such a housing.

In other examples, different electrode configurations comprising a single lead, two leads, three leads, or more may be provided. In addition, electrode counts on leads may vary and may be the same or different from a lead to lead. Examples of other configurations include one lead with eight electrodes (1×8), two leads with four electrodes each (2×4), three leads with four electrodes each (3×4), three leads with eight electrodes each (3×8), three leads with four, eight, and four electrodes, respectively (4-8-4), or other configurations. Different electrodes are selected to form electrode combinations. Polarities are assigned to the selected electrodes to form electrode configurations.

Electrode 48Q represents one or more electrodes that may be carried on a housing, i.e., can, of implantable stimulator 4. Electrode 48Q may be configured as a regulated or unregulated electrode for use in an electrode configuration with selected regulated and/or unregulated electrodes among electrodes 48A-48Q, which may be located by one or more leads, as described above. As further alternatives, in some examples, electrodes 48A-48Q may be formed together on an integrated, leadless implantable stimulator 4. For example, electrodes 48A-48Q may be formed together on a housing that carries the electrodes and houses the components of implantable stimulator 4, such as stimulation generator 60, processor 50, memory 52, telemetry module 56, and power source 54.

The housing that carries electrodes 48A-48Q may be a unitary housing or a housing that combines submodules in a fixed or movable relationship with respect to one another. For example, stimulation generator housing submodule may be coupled to an electrode housing submodule. In each case, the electrodes 48A-48Q are provided on the housing or housing submodule instead of on an elongated lead or leads. Two or more regulated electrodes located on the housing may be combined with one or more unregulated electrodes located on the housing to form various electrode configurations as described in this disclosure.

Selected electrodes may be configured via switches or adaptable current regulators to provide regulated or unregulated current paths within the electrode configuration on a selection basis, consistent with this disclosure. The regulated or unregulated current paths may be source or sink paths. In this manner, regulated, bi-directional constant current sources can be used in conjunction with one or more reference electrodes. The current regulators control the amount of current being delivered or received via respective regulated electrodes. The unregulated, reference electrode can be used to balance any potential unbalanced charge that may be delivered between the regulated current sources and the regulated current sinks during delivery of a stimulation waveform or pulses.

Memory 52 may store instructions for execution by processor 50, stimulation therapy data, sensor data, and/or other information regarding therapy for patient 6. Processor 50 may control stimulation generator 60 to deliver stimulation according to a selected one or more of a plurality of programs or program groups stored in memory 52. Memory 52 may include any electronic data storage media, such as random access memory (RAM), read-only memory (ROM), electronically-erasable programmable ROM (EEPROM), flash memory, or the like. Memory 52 may store program instructions that, when executed by processor 50, cause the processor to perform various functions ascribed to processor 50 and implantable stimulator 4 in this disclosure.

Processor 50 may include one or more microprocessors, digital signal processors (DSPs), application-specific integrated circuits (ASICs), field-programmable gate arrays (FPGAs), or other digital logic circuitry. Processor 50 controls operation of implantable stimulator 4, e.g., controls stimulation generator 60 to deliver stimulation therapy according to a selected program or group of programs retrieved from memory 52. For example, processor 50 may control stimulation generator 60 to deliver electrical signals, e.g., as stimulation pulses or continuous waveforms, with current amplitudes, pulse widths (if applicable), and rates specified by one or more stimulation programs. Processor 50 may also control stimulation generator 60 to selectively deliver the stimulation via subsets of electrodes 58, also referred to as electrode combinations, and with polarities specified by one or more programs.

Upon selection of a particular program group, processor 50 may control stimulation generator 60 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate, if applicable. For a continuous waveform, parameters may include amplitude and frequency. In addition, each program may specify a particular electrode combination for delivery of stimulation, and an electrode configuration in terms of the polarities and regulated/unregulated status of the electrodes. Again, the electrode combination may specify particular electrodes in a single array or multiple arrays, and on a single lead or among multiple leads.

Stimulation generator 60 is electrically coupled to electrodes 48A-P via conductors of the respective lead, such as lead segments 12 in FIG. 1 or leads 32 in FIG. 2, in implementations in which electrodes 48A-P are carried by, located on, leads. If one or more housing ("can") electrodes 48Q are provided, stimulation generator 60 may be electrically coupled to such an electrode via an electrical conductor disposed within the housing of implantable stimulator 4 (FIG. 1) or implantable stimulator 34 (FIG. 2). A can electrode 48Q may be configured as a regulated or unregulated electrode to form an electrode configuration in conjunction with two or more of electrodes 48P-48Q, which may be located on leads or on the housing of stimulator 4.

Stimulation generator 60 may include stimulation generation circuitry to generate stimulation pulses or waveforms and circuitry for switching stimulation across different electrode combinations, e.g., in response to control by processor 50. Stimulation generator 60 produces an electrical stimulation signal in accordance with a program based on control signals from processor 50.

For example, stimulation generator 60 may include a charging circuit that selectively applies energy from power source 54 to a capacitor module for generation and delivery of a supply voltage for generation of stimulation signal. In addition to capacitors, the capacitor module may include switches. In this manner, the capacitor module may be configurable, e.g., based on signals from processor 50, to store a desired voltage for delivery of stimulation at a voltage or current amplitude specified by a program. For delivery of stimulation pulses, switches within the capacitor module may control the widths of the pulses based on signals from processor 50.

Stimulation generator 60 may be capable of delivering stimulation using two or more of electrodes 48A-Q as stimulation electrodes and a different one or more of electrodes 48A-Q as reference electrodes. Accordingly, stimulation generator 60 may include stimulation circuitry such as bi-directional, regulated current sources for each of electrodes 48A-Q. Again, a bi-directional current source may refer to a regulated current source or sink on an interchangeable basis. A regulated current source or sink may generate regulated currents using a supply voltage provided by a capacitor module as described above. In one embodiment, stimulation generator 60 includes an array of regulated bi-directional current sources and an array of switches. Electrodes may be selectively coupled to a reference voltage via the switches.

Figure 6:
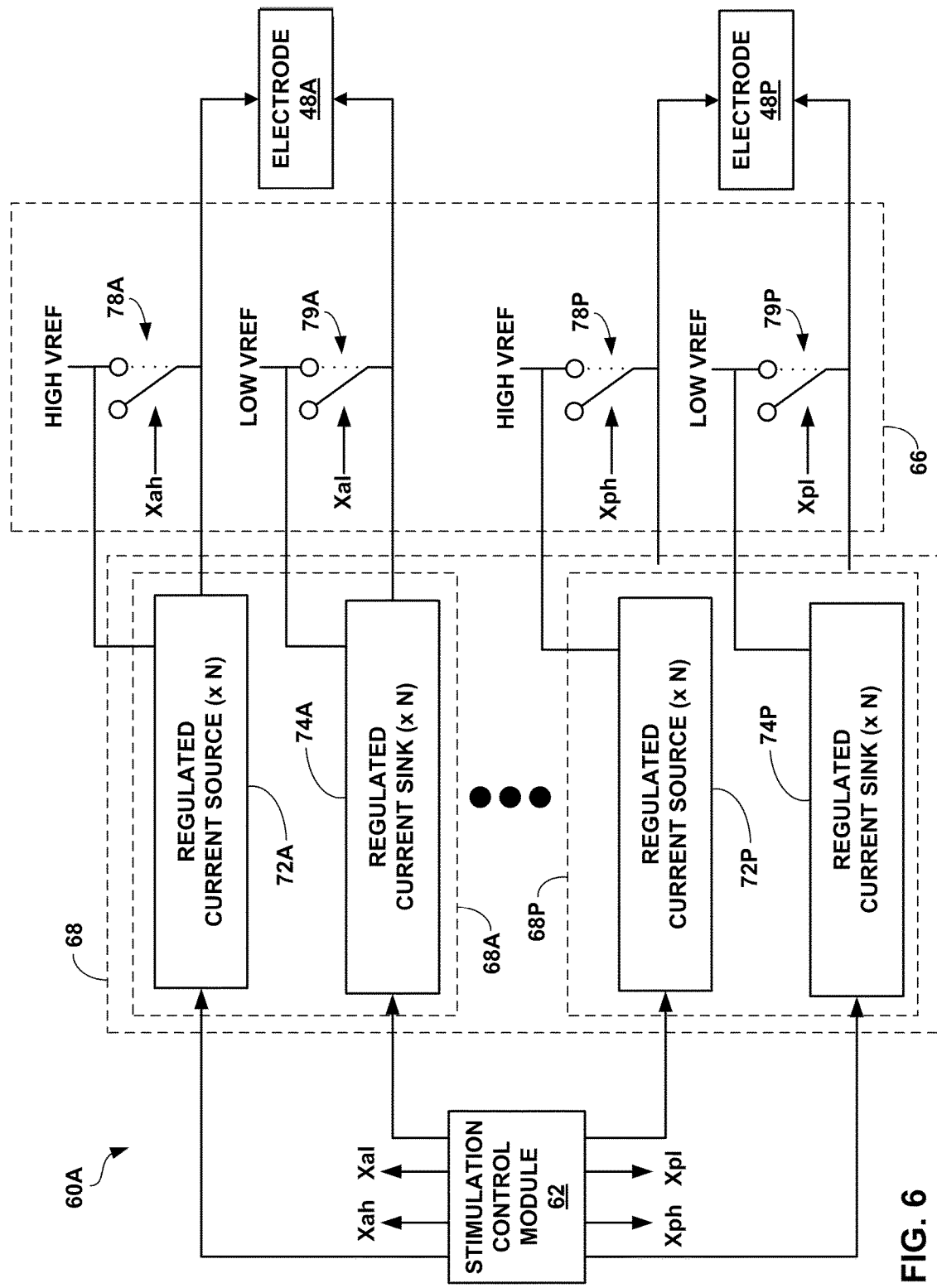
FIG. 6 is a block diagram illustrating the example stimulation generator of FIG. 5 in greater detail.

The reference voltage may be a high reference voltage for unregulated anodic operation or a low reference voltage for unregulated cathodic operation, each of which may be provided by a capacitor module as described above. Again, the capacitor module may be configurable, based on signals from processor 50, to store a desired voltage for use by a regulated current source or sink to deliver of current-based stimulation pulses as specified by a program. When an electrode is used as a regulated electrode, an associated regulated current source or sink may be activated. The current source or sink may be directly coupled to the electrode with or without an intervening switch. If the current source or sink is not turned ON, the electrode will not be active unless it is coupled by a switch to a high or low reference voltage for unregulated operation. An example configuration for this embodiment is shown in FIG. 6.

Figure 12:
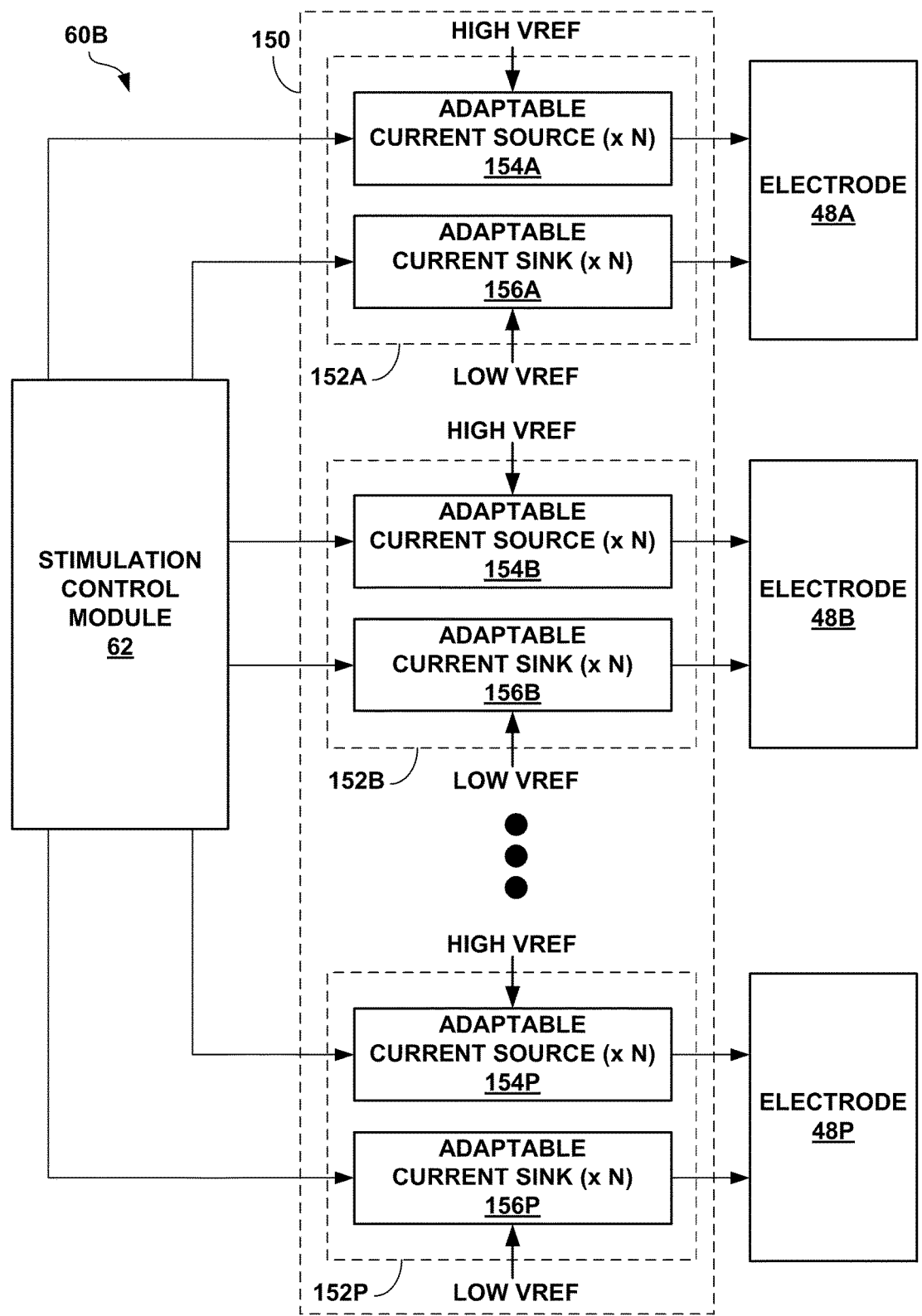
FIG. 12 is a block diagram illustrating various components of the stimulation generator shown in FIG. 11 in greater detail.

In another embodiment, stimulation generator 60 includes adaptable stimulation circuitry for each of electrodes 48 A-Q, in which case separate switches to form unregulated electrodes may be omitted in some implementations. The adaptable stimulation circuitry may include adaptable regulated current sources that, in effect, may operate as either a regulated current source or an unregulated switch that couples an electrode to a reference voltage. An example configuration for an embodiment including adaptable regulated current sources is shown in FIG. 12.

Telemetry module 56 may include a radio frequency (RF) transceiver to permit bi-directional communication between implantable stimulator 4 and each of clinician programmer 20 and patient programmer 22. Telemetry module 56 may include an antenna 57 that may take on a variety of forms. For example, antenna 57 may be formed by a conductive coil or wire embedded in a housing associated with medical device 4. Alternatively, antenna 57 may be mounted on a circuit board carrying other components of implantable stimulator 4 or take the form of a circuit trace on the circuit board. In this way, telemetry module 56 may permit communication with clinician programmer 20 and patient programmer 22 in FIG. 1 or external programmer 40 in FIG. 2, to receive, for example, new programs or program groups, or adjustments to programs or program groups.

Power source 54 may be a non-rechargeable primary cell battery or a rechargeable battery and may be coupled to power circuitry. However, the disclosure is not limited to embodiments in which the power source is a battery. In another embodiment, as an example, power source 5 may comprise a supercapacitor. In some embodiments, power source 54 may be rechargeable via induction or ultrasonic energy transmission, and include an appropriate circuit for recovering transcutaneously received energy. For example, power source 54 may be coupled to a secondary coil and a rectifier circuit for inductive energy transfer. In additional embodiments, power source 54 may include a small rechargeable circuit and a power generation circuit to produce the operating power. Recharging may be accomplished through proximal inductive interaction between an external charger and an inductive charging coil within stimulator 4. In some embodiments, power requirements may be small enough to allow stimulator 4 to utilize patient motion at least in part and implement a kinetic energy-scavenging device to trickle charge a rechargeable battery. A voltage regulator may generate one or more regulated voltages using the battery power.

Figure 4:
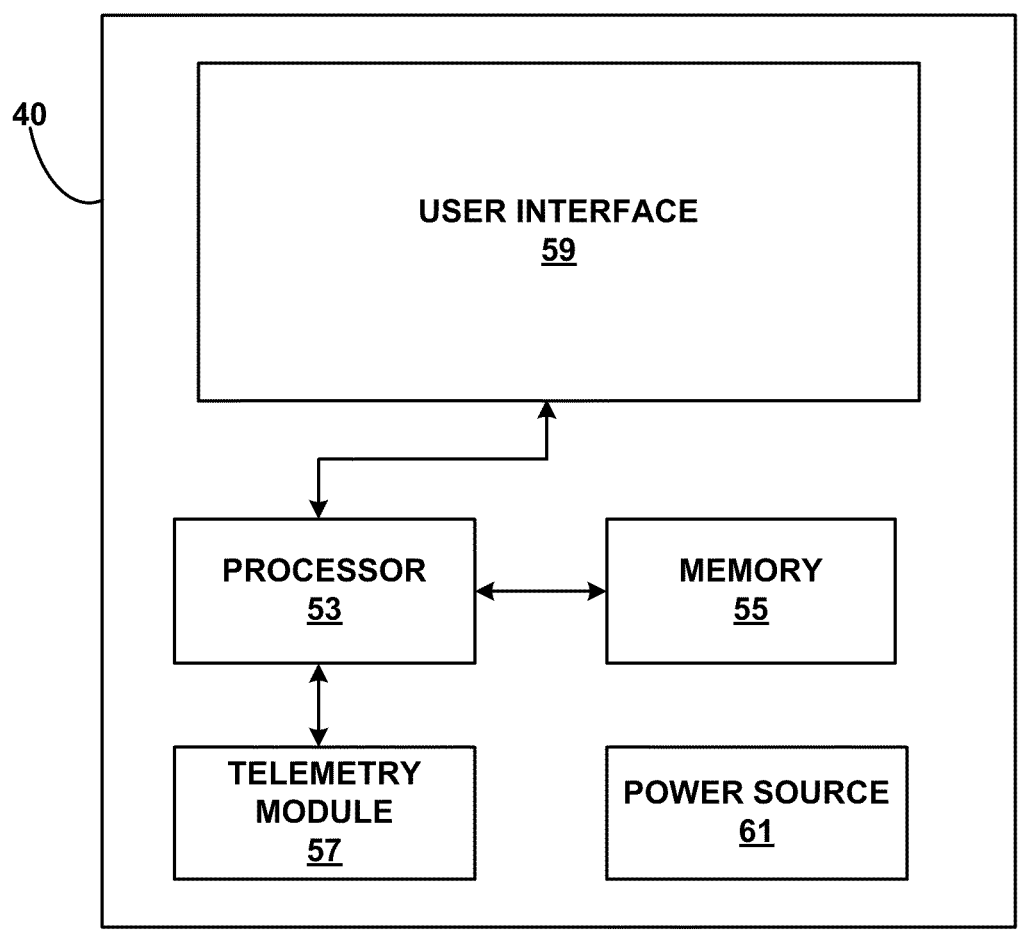
FIG. 4 is a block diagram illustrating various example components of an external programmer.

FIG. 4 is a functional block diagram illustrating various components of an external programmer 40 for an implantable stimulator 14. Although the components shown in FIG. 4 are described in reference to external programmer 40, the components may also be included within clinician programmer 20 or patient programmer 22 shown in FIG. 1. As shown in FIG. 4, external programmer 40 includes processor 53, memory 55, telemetry module 57, user interface 59, and power source 61. In general, processor 53 controls user interface 59, stores and retrieves data to and from memory 55, and controls transmission of data with implantable stimulator 34 through telemetry module 57. Processor 53 may take the form of one or more microprocessors, controllers, DSPs, ASICS, FPGAs, or equivalent discrete or integrated logic circuitry. The functions attributed to processor 53 herein may be embodied as software, firmware, hardware or any combination thereof.

Memory 55 may store instructions that cause processor 53 to provide various aspects of the functionality ascribed to external programmer 40 herein. Memory 55 may include any fixed or removable magnetic, optical, or electrical media, such as RAM, ROM, CD-ROM, magnetic disks, EEPROM, or the like. Memory 55 may also include a removable memory portion that may be used to provide memory updates or increases in memory capacities. A removable memory may also allow patient data to be easily transferred to another computing device, or to be removed before programmer 40 is used to program therapy for another patient. Memory 55 may also store information that controls operation of implantable stimulator 4, such as therapy delivery values.

A clinician or patient 36 interacts with user interface 59 in order to, for example, manually select, change or modify programs, adjust voltage or current amplitude, provide efficacy feedback, or view stimulation data. User interface 59 may include a screen and one or more input buttons that allow external programmer 40 to receive input from a user. The screen may be a liquid crystal display (LCD), plasma display, dot matrix display, or touch screen. The input buttons may include a touch pad, increase and decrease buttons, emergency shut off button, and other input media needed to control the stimulation therapy.

Telemetry module 57 allows the transfer of data to and from stimulator 34. Telemetry module 57 may communicate automatically with stimulator 34 at a scheduled time or when the telemetry module detects the proximity of the stimulator. Alternatively, telemetry module 57 may communicate with stimulator 34 when signaled by a user through user interface 59. To support RF communication, telemetry module 44 may include appropriate electronic components, such as amplifiers, filters, mixers, encoders, decoders, and the like.

Programmer 40 may communicate wirelessly with implantable stimulator 34 using, for example, RF communication or proximal inductive interaction. This wireless communication is possible through the use of telemetry module 44 which may be coupled to an internal antenna or an external antenna. Telemetry module 44 may be similar to telemetry module 57 of implantable stimulator 34.

Programmer 40 may also be configured to communicate with another computing device via wireless communication techniques, or direct communication through a wired, e.g., network, connection. Examples of local wireless communication techniques that may be employed to facilitate communication between programmer 24 and another computing device include RF communication based on the 802.11 or Bluetooth specification sets, infrared communication, e.g., based on the IrDA standard.

Power source 61 delivers operating power to the components of programmer 40. Power source 61 may be a rechargeable battery, such as a lithium ion or nickel metal hydride battery. Other rechargeable or conventional batteries may also be used. In some cases, external programmer 40 may be used when coupled to an alternating current (AC) outlet, i.e., AC line power, either directly or via an AC/DC adapter. Power source 61 may include circuitry to monitor power remaining within a battery. In this manner, user interface 59 may provide a current battery level indicator or low battery level indicator when the battery needs to be replaced or recharged. In some cases, power source 61 may be capable of estimating the remaining time of operation using the current battery.

Figure 5:
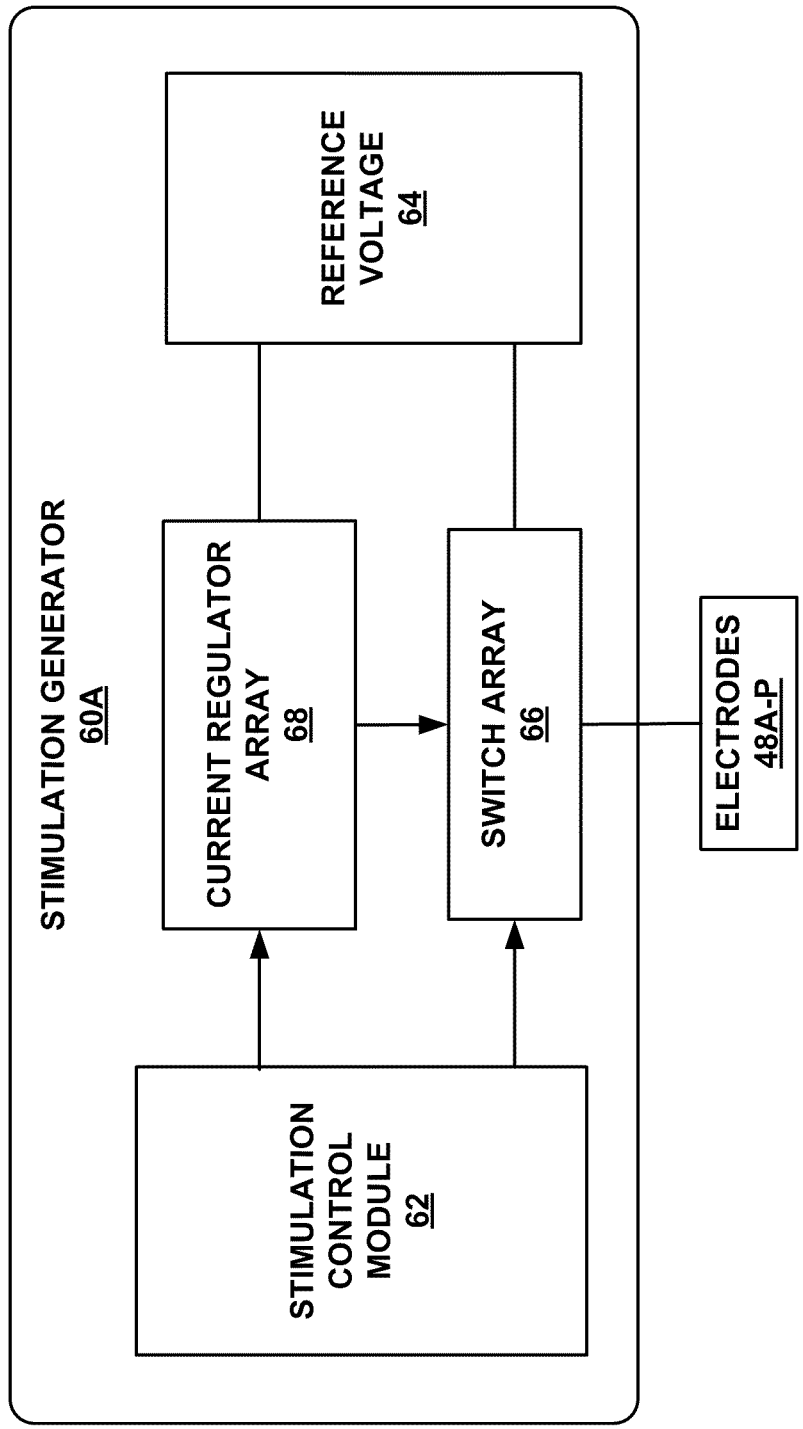
FIG. 5 is a block diagram illustrating various components of an example electrical stimulation generator for use in the implantable electrical stimulator of FIG. 3.

FIG. 5 is a block diagram illustrating various components of an example stimulation generator 60A. Stimulation generator 60A may be used with an implantable stimulator, e.g., to perform the functions of stimulation generator 60 as described with reference to FIGS. 1-3. Although described with respect to implantable stimulator 4, stimulation generator 60A may also be used for implantable stimulator 34, or other types of stimulators. In the example of FIG. 5, stimulation generator 60A is selectively, e.g., based on a signal from processor 50 (FIG. 3), configured to deliver constant current stimulation pulses to patient 6 via various electrode combinations. However, the disclosure is not limited to embodiments in which regulated current pulses are delivered. In other embodiments, stimulation generator 60A may provide continuous, regulated current waveforms, rather than regulated current pulses. In still other embodiments, stimulation generator 60A may deliver combinations or continuous waveforms and pulses, or selectively deliver either continuous waveforms or pulses.

In the example illustrated in FIG. 5, stimulation generator 60A includes stimulation control module 62, reference voltage source 64, switch array 66, and current regulator array 68. Reference voltage source 64 may provide operating power to current regulator array 68, and may include a regulated voltage that sets the level of the reference voltage. As shown in FIG. 5, reference voltage source 64 may be coupled to provide operating power for the current regulator array 68 and provide a reference voltage for connection to electrodes 48A-48Q for an unregulated mode of electrode operation. In other examples, however, the voltage level of the reference voltage and the operating voltage level provided to regulated current source array 68 may be different.

Stimulation control module 62 forms a stimulation controller that controls switch array 66 and current regulator array 68 to deliver stimulation via electrodes 48A-48Q. Stimulation control module 62 may include one or more microprocessors, microcontrollers, digital signal processors (DSPs), application-specific integrated circuits (ASICs), field-programmable gate arrays (FPGAs), or other integrated or discrete logic circuitry. In operation, stimulation control module 62 may control delivery of electrical stimulation according to one or more programs that may specify stimulation parameters such as electrode combination, electrode polarity, stimulation current amplitude, pulse rate, and/or pulse width. Programs may be defined by a user via an external controller and downloaded to an implantable stimulator 4 or 34 for use by stimulation control module 62.

Current regulator array 68 includes a plurality of regulated current sources or sinks Again, a current regulator may function as either a current source or sink, or be selectively configured to operate as either a source or a sink. For convenience, however, the term "current regulator" may be used in some instances to refer to either a source or sink. Hence, each of the current regulators in current regulator array 68 may operate as a regulated current source that delivers stimulation via a corresponding one of electrodes 48A-Q or a regulated current sink that receives current from a corresponding one of electrodes 48A-Q, where electrodes 48A-48Q may be provided on leads, on a stimulator housing, on a leadless stimulator, or in other arrangements. In general, electrodes 48A-48Q may be referred to below as electrodes 48 for conciseness.

In some embodiments, each current regulator may include generally parallel source and sink circuits that can be individually selected to source or sink regulated current, or a single configurable circuit that can be configured to source or sink regulated current. In either case, for this example, each current regulator in current regulator array 68 may be considered bi-directional in the sense that it may deliver (source) or receive (sink) regulated current. Thus, each current regulator of regulated current source array 68 may be referred to as a regulated bidirectional current regulator. The regulated bidirectional current sources of current regulator array 68 may be configured as current mirrors that receive an input voltage from regulated reference voltage 64 or another supply voltage and output a substantially constant current value in response to the input voltage. The output current value may be programmable and may be controlled by a stimulation controller such as stimulation control module 62.

Each switch of switch array 66 couples a corresponding one of electrodes 48 to either a corresponding bidirectional current regulator of current regulator array 68 or to reference voltage 64. Stimulation control module 62 selectively opens and closes switches in switch array 66 to configure two or more of electrodes 48 as regulated electrodes by connection to regulated current sources or sinks in current regulator array 68 and one or more of electrodes 48 as unregulated electrodes by connection to reference voltage 64. In addition, stimulation control module 62 may selectively control individual regulated current sources or sinks in current regulator array 68 to deliver stimulation current pulses to the selected electrodes.

Reference voltage 64 may be a high or low voltage supplied by a regulated power source, depending on whether an electrode is programmed to be an unregulated source (high voltage rail) or unregulated sink (low voltage rail). Hence, reference voltage 64 may produce high and low reference voltages for selective coupling to unregulated, reference electrodes as needed given the selected electrode configuration. A regulated power source may produce one or more regulated voltage levels for use as reference voltage 64 and for use as a power rail for current regulator array 68. Again, although the same reference voltage 64 is coupled to current regulator array 68 in FIG. 5, different voltage levels could be used for the reference voltage coupled to switch array 66 and the operating voltage level provided to the regulated current source array. A regulated power source may generate the regulated voltages from voltages provided by a power source 54 (FIG. 3), such as a battery.

In some cases, a regulated power source may be configured to generate multiple regulated voltage levels for use by different components within implantable stimulator 4, e.g., using a so-called voltage regulator stack. The voltage level delivered to current regulator array 68 by reference voltage 64 as a supply rail may be produced by a capacitor module that is charged for generation and delivery of a supply voltage for generation of a stimulation signal. The voltage level may be programmable and may be selected to provide sufficient headroom for operation of the regulated current sources. The voltage level provided by reference voltage 64 may be selected to provide an appropriate potential for generation of desired stimulation currents in conjunction with current regulator array 68. In general, the voltage levels produced by a regulated power source, including reference voltage 64, are not current regulated. Although the voltage levels produced by a regulated power source are constant, the current levels sourced or sunk with respect to such voltage levels may vary as a function of load. Hence, because reference voltage 64 is voltage-regulated but not current-regulated, switches in switch array 66 may selectively couple electrodes 48 to the reference voltage via unregulated current paths.

Stimulation control module 62 controls the operation of switch array 66 to produce electrode configurations defined by different stimulation programs. In some cases, the switches of switch array 66 may be metal-oxide-semiconductor field-effect-transistors (MOSFETs) or other circuit components used for switching electronic signals. The switches of switch array 66 may be designed to carry an amount of unregulated current that may be coupled to a corresponding electrode through an unregulated current path associated with reference voltage 64. As previously described, two or more regulated, stimulation electrodes 48 may be intentionally programmed to deliver different amounts of current such that the regulated electrodes produce an unbalanced current distribution.

One or more unregulated electrodes coupled to reference voltage 64 via respective switches in switch array 66 may balance the current distribution produced by the regulated electrodes via unregulated current paths. In some examples, each of the switches of switch array 66 may be capable of carrying a larger amount of current than a current regulator of current regulator array 68. To facilitate larger current carrying capacity, the sizes of the switches of switch array 66 may be larger than output transistors associated with the regulated current sources. The sizes of the switches may be selected according to desired current carrying capacity of a reference electrode.

To provide individual control of electrodes 48 as either regulated electrodes or as unregulated, reference electrodes, stimulation control module 62 controls operation of switch array 66, and current regulator array 68. When stimulation is delivered to patient 6, for the example of current pulses, stimulation control module 62 controls switch array 66 to couple selected stimulation electrodes for a desired electrode combination to respective current regulators of current regulator array 68 or to reference voltage 64, as needed. Stimulation control module 62 controls the regulated bidirectional current sources of current regulator array 68 coupled to regulated electrodes to source or sink specified amounts of current. For example, stimulation control module 62 may control selected current sources or sinks to on a pulse-by-pulse basis to deliver current pulses to corresponding electrodes.

Stimulation control module 62 also deactivates the regulated bidirectional current regulators of current regulator array 68 tied to inactive electrodes, i.e., electrodes that are not active as regulated electrodes in a given electrode configuration. Each regulated bidirectional current regulator of current regulator array 68 may include an internal enable switch controlled by stimulation control module 62 that disconnects regulated power source 64 from the current regulator or otherwise disables the current source when the corresponding electrode is not used as a regulated electrode to deliver stimulation. Hence, configuration of electrodes 48A-48P may involved coordinated control of current regulator array 68 and switch array 66 to selectively activate current sources that are coupled to selected, regulated electrodes, selectively deactivate current sources that are coupled to electrodes that are either not selected or selected to be unregulated electrodes, and selectively couple and uncouple regulated and unregulated electrodes, respectively, to regulated current sources and reference voltage 64 via switch array 66.

FIG. 6 is a block diagram illustrating an example of various components of stimulation generator 60A shown in FIG. 5 in greater detail. In particular, FIG. 6 shows current regulator array 68 and switch array 66 in greater detail. As shown in FIG. 6, current regulator array 68 includes regulated bidirectional current regulators 68A-P and switch array 66 includes switches 78A-P and 79A-P. Each of bidirectional current regulators 68A-P includes a corresponding one of regulated current sources 72A-P that delivers regulated stimulation current to the corresponding electrode and a corresponding one of regulated current sinks 74A-P that receives regulated stimulation current from the corresponding electrode. Note that the block diagram illustrated in FIG. 6 is intended as a conceptual diagram that shows how stimulation generator 60A can be configured to control the operation of electrodes 48 in different modes, i.e., an off mode, regulated modes, and unregulated, reference modes. Thus, for ease of illustration, not all power and control signals are shown in FIG. 6.

In the example of FIG. 6, switches 78A-P may be coupled at one end to a high voltage reference, which may correspond to a high reference voltage level of reference voltage 64, and to a corresponding one of electrodes 48 at the other end. Switches 79A-P may be coupled at one end to a low voltage reference, which may correspond to low reference voltage level of reference voltage 64, and to a corresponding one of electrodes 48 at the other end. High reference voltage (High Vref) and low reference voltage (Low Vref) represent high and low voltage levels of reference voltage 64 (FIG. 5) and may be supplied by power source 54. For example, the high reference voltage may correspond to a reference voltage level and the low reference voltage may correspond to a ground potential to which the reference voltage level is referenced.

As further shown in FIG. 6, each regulated current source 72A-72P may be coupled to the high reference voltage or another upper voltage rail, which supports regulator overhead and sources current that is regulated by the regulated current source. In addition, each regulated current sink 74A-74P may be coupled to the low reference voltage or another lower voltage rail or ground potential, which supports regulator overhead and sinks current that is regulated by the regulated current sink.

Stimulation control module 62 controls the operation of regulated current sources 72A-72P, sinks 74A-74P, switches 78A-78P, and switches 79A-79P to configure electrodes 48A-48P as either inactive (i.e., off), regulated cathodes, regulated anodes, unregulated cathodes or unregulated anodes. For example, stimulation control module 62 may generate control signals to individually control regulated current sources 72A-72P to deliver specified amounts of regulated current to electrodes 48A-48P, respectively, and thereby configure such electrodes as regulated anodes. A can electrode 48Q may also be provided and coupled to regulated or unregulated current paths.

Similarly, stimulation control module 62 may generate control signals to individually control regulated current sinks 74A-74P to receive specified amounts of regulated currents from electrodes 48A-48P, respectively, and thereby configure such electrodes as regulated cathodes. For example, stimulation control module 62 may enable the current sources or sinks and also specify control voltages or current to be applied to the source or sinks to control the amount of current that is sourced or sunk via the respective electrodes 48A-48P.

In addition, stimulation control module 62 may generate control signals to control switches 78A-78P and 79A-79P to selectively couple electrodes 48A-48P to the high reference voltage or the low reference voltage, respectively. For example, stimulation control module 62 may generate control signals Xah-Xph to close switches 78A-78P, respectively, and couple electrodes 48A-P to the high reference voltage. In this manner, electrodes 48A-P may be selectively configured as unregulated, reference anodes that source current from the high reference voltage. Similarly, stimulation control module 62 may generate control signals Xal-Xpl to close switches 79A-P, respectively, and couple electrodes 48A-P to the low reference voltage. In this manner, electrodes 48A-P may be selectively configured as unregulated, reference cathodes that sink current to the low reference voltage.

In general, an electrode 48A-48P may have one of five states: regulated cathode coupled to a regulated current sink 74A-74P, regulated anode coupled to a regulated current source 72A-72P, unregulated anode coupled to the high reference voltage, unregulated cathode coupled to the low reference voltage, or floating electrode not coupled to any circuit potential. Sources 72A-72P, sinks 74A-74P, switches 78A-78P, and switches 79A-79P are controlled by stimulation control module 62 such that only one of the above states is active for an electrode 48A-48P at a given time. For example, when electrode 48A operates as a regulated anode, regulated current source 72A is active, regulated current sink 74A is inactive, switch 78A is open and switch 79A is open. When a regulated source or sink is inactive, it may be in a high impedance state such that electrode 48A sees the source or sink as substantially an open circuit connection.

In an example implementation, each current regulator, in the form of either regulated current source 72A-72P or regulated current sink 74A-74P, may be implemented as a plurality of regulated current sources and sinks, respectively, operating in parallel to produce a combined, programmable current level sufficient for a desired stimulation therapy. A regulated current source 72A, for example, may be implemented by several parallel current sources (x N) having identical or similar structures. Similarly, a regulated current sink may be implemented by several parallel current sinks (x N) having identical or similar structures.

Hence, a regulated current source 72A may be implemented as N parallel, regulated current sources, each delivering a fraction of a total regulated current to be sourced by electrode 48A. Similarly, a regulated current sink 74A may be implemented as N parallel, regulated current sinks, each sinking a fraction of a total regulated to be sunk by electrode 48A. By activating a selected number of the parallel, regulated current sources forming a regulated current source 72A, stimulation control module 62 may control an amount of regulated source current delivered to a given electrode 48A coupled to the respective current source. Similarly, by activating a selected number of parallel, regulated current sink branches forming a regulated current sink 74A, stimulation control module 62 may control an amount of regulated sink current delivered from a given electrode 48A coupled to the respective current sink.

As an example, each current regulator, e.g., regulated source 72A-P or regulated sink 74A-P, may be implemented by N parallel current regulator branches. As an example, N may be equal to 64 in some implementations. In this type of implementation, stimulation control module 62 may specify a reference source current and a reference sink current, e.g., based on program data specified automatically or by a user via an external programmer. For each electrode, stimulation control module 62 may further specify a percentage of the reference source current or reference sink current to be delivered via the electrode, e.g., based on program data.

A control signal may be applied to each parallel current regulator branch such that the current levels produced by all N branches will add up to approximately the reference current level. Based on the percentage, which may be referred to as a gain ratio, stimulation control module 62 may selectively activate or deactivate a number of parallel current regulator branches for a given electrode sufficient to produce the specified percentage of the reference current. In this manner, stimulation control module 62 selectively scales up or scales down the number of active, parallel current regulator branches. If the reference current is 20 milliamps (mA), for example, the control signal is selected such that activation of all N parallel current regulator branches would produce 20 mA of source current or sink current, as applicable, for application via an electrode. In this case, the control signal may be selected such that each current regulator branch produces $1/N^{th}$ of the reference current.

If the percentage to be delivered by a given electrode is 50 percent, then stimulation control module 62 activates 50 percent of the N parallel current regulator branches or, conversely, deactivates 50 percent of the N parallel current regulator branches. In either case, N/2 parallel current regulator branches are activated, producing a combined current of 50%×20 mA=10 mA in this example. Hence, when activated, each current regulator may source or sink a finite amount of current, determined as a function of the control signal, such that the fractional currents flowing in the parallel regulator branches can be summed to produce an overall regulated current. If the reference current is changed, the applicable control signal applied by to each current regulator branch is changed.

By specifying percentages of source current and sink current for respective electrodes, stimulation control module 62 can control current regulators 72A-72P and 74A-74B to precisely and selectively control the current levels sourced or sunk by particular electrodes 48A-48P. In addition, stimulation control module 62 can support effective steering of stimulation current to create different electrical stimulation fields or patterns useful in electrical stimulation therapy.

Using regulated current source 72A and electrode 48A as an example, the outputs of the parallel current source branches forming the regulated current source are coupled to electrode 48A such that the electrode receives a sum of the regulated source currents produced by the multiple, parallel current source branches. A similar arrangement can be provided for current sinks 74A-74P. Hence, the description of a single source or sink and the representation of a single source or sink in FIG. 6 are provided for purposes of illustration, and may represent either a single source or sink or multiple, parallel sources or sinks configured as described in this disclosure. Likewise, each switch 78A-78P, 79A-79P may be implemented by a single switch, or by multiple, parallel switches operating to support a sum of the multiple, fractional currents sourced or sunk via each parallel switch.

When turned "ON," each parallel current source or sink branch may produce a known amount of current, defined by the reference current and corresponding control signal, as described above. In this manner, a source or sink may be considered either ON or OFF, and deliver the same fractional amount of current as other sources or sinks whenever it is ON. Alternatively, in some embodiments, each parallel current source or sink could be configured to provide different fractional amounts of current, or deliver variable amounts of current according to a bias signal. Although it is understood that each given source 72A-72P or sink 74A-74P may include multiple, parallel source branches or sink branches, and that a given switch 78A-78P or 79A-79P may include multiple, parallel switches, this disclosure will generally refer to each of sources 72A-72P, sinks 74A-74P, or switches 78A-78P, 79A-79P on a singular basis for ease of illustration.

FIGS. 7A-7D are block diagrams illustrating operation of example stimulation circuitry in producing different regulated and unregulated electrode configurations for use in the stimulation generator shown in FIGS. 5 and 6. The example of FIG. 7A represents an OFF or inactive state in which an electrode 48A does not form an active electrode in the present electrode configuration. In this case, regulated current source 72A and regulated current sink 74 are both OFF, as indicated by the hatching. In addition, switches 78A and 79A are open. Consequently, electrode 48A is not coupled to the high reference voltage or low reference voltage, or to any other circuit potential, and instead is in a floating state.

FIG. 7B represents a regulated anode state in which electrode 48A is coupled to an active, regulated current source 72A to source regulated current. In this example, regulated current sink 74A is inactive and switches 78A, 79A are open. FIG. 7C represents a regulated cathode state in which electrode 48A is coupled to an active, regulated current sink 74A to sink regulated current. In this example, regulated current source 72A is inactive and switches 78A, 79A are open.

FIG. 7D represents an unregulated anode state in which electrode 48A is coupled to the high reference voltage via closed switch 78A to source unregulated current from the regulated high reference voltage. In this example, regulated current source 72A is inactive, regulated current sink is inactive, and switch 79A is open. Although not shown in FIGS. 7A-7D, an unregulated cathode state is another possible configuration for electrode 48A. In this case, electrode 48A is coupled to the low reference voltage to sink unregulated current via closed switch 79A. For the unregulated cathode state, regulated current source 72A and regulated current sink 74A are both inactive and switch 78A is open.

Configuration of electrode 48A, as shown in FIGS. 7A-7D, in conjunction with configuration of other electrodes 48A-48P, may be used to define a variety of different electrode configurations. Such electrode configurations may include combinations of regulated electrodes that produce unbalanced current distributions, and one or more unregulated electrodes that source or sink unregulated current from and to a high or low reference voltage, respectively, to restore a charge balance among the electrodes, as needed. For example, regulated electrodes may source and sink different amounts of current, leaving a net difference or sum of current to be sourced or sunk by one or more unregulated electrodes in the electrode configuration.

Figure 8:
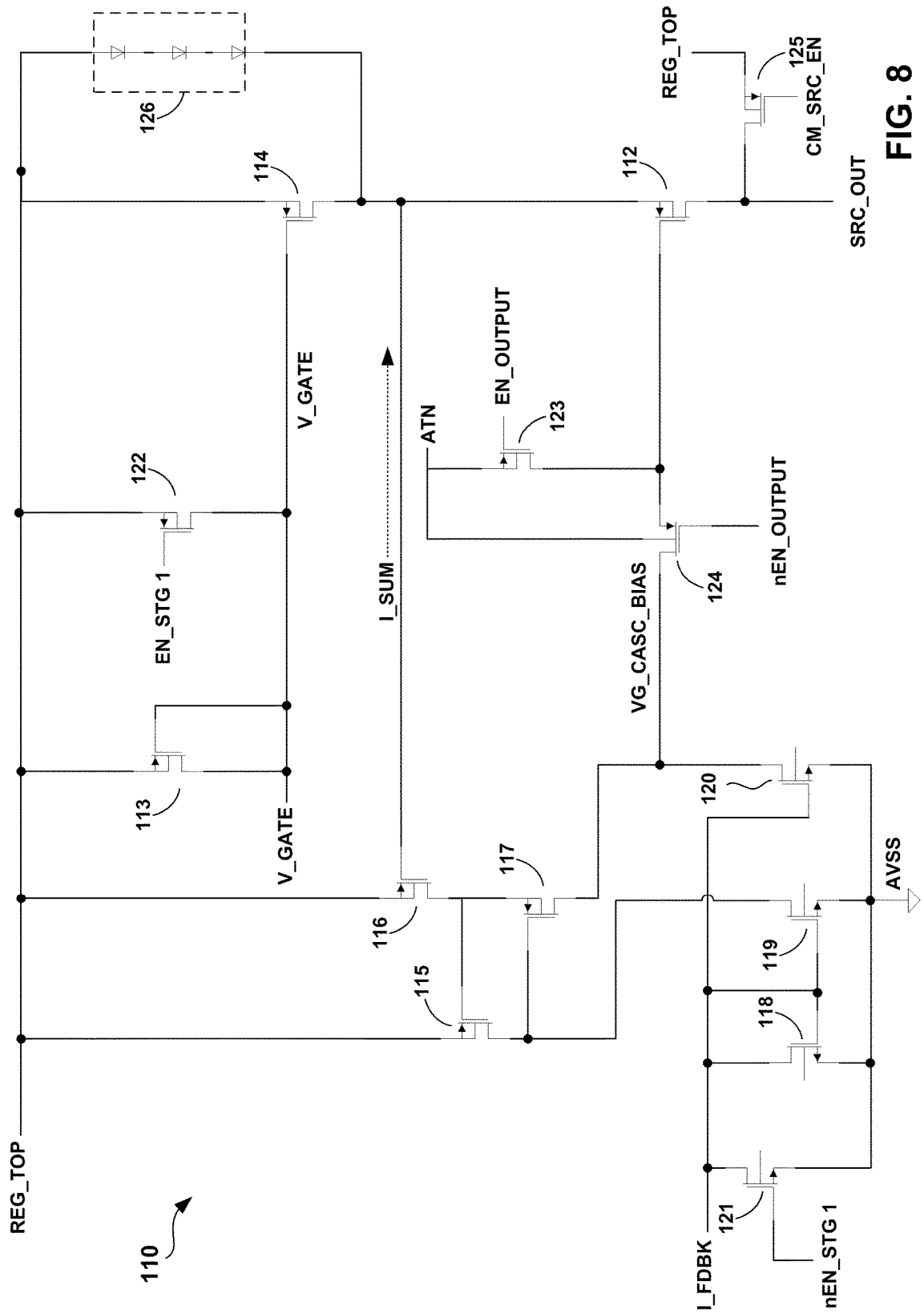
FIGS. 8 and 9 are circuit diagrams illustrating example circuitry for use in the stimulation generators shown in FIGS. 5 and 6.

FIG. 8 is a schematic circuit diagram illustrating an example circuit 110 that may be used to implement stimulation generator 60A shown in FIGS. 5 and 6. In the example of FIG. 8, transistors 112-124 are configured to operate as a regulated current source to output a regulated current to an electrode based on an input signal. For this reason, transistors 112-124 may collectively be referred to as a current regulator and, more specifically, a regulated current source. The regulated current source formed by transistors 112, 124 may generally correspond to a regulated current source 72A-72P of FIGS. 6 and 7A-7D. The circuit 110 of FIG. 8 may be one of several, e.g., 64, parallel circuits that together form a given regulated current source, as discussed above. Again, each of the parallel circuits may produce a fractional amount of current that can be summed with fractional amounts of current from other parallel circuits to scale up or down a desired overall level of regulated source current. However, the following description will generally focus on a single circuit 110, which may be used alone or in combination with multiple, parallel circuit branches.

In the example of FIG. 8, transistor 125 operates as a switch and is used to couple the output (SRC_UT) of example circuit 110 to an unregulated reference voltage. The output SRC_OUT may be coupled to a respective electrode in an array of electrodes carried by one or more implantable leads. In some cases, the output SRC_OUT may be coupled to a can electrode. Hence, transistor 125 may generally correspond to switch 72 of FIGS. 6 and 7A-7D, which selectively couples an electrode to a high reference voltage.

In this manner, switch 125 couples the electrode to source unregulated current from the high reference voltage via an unregulated current path and, in effect, bypasses the current regulator circuit.

Transistors 121-124 are used to turn transistors 112-120 OFF when switch 125 couples the electrode to the unregulated current path or when the electrode is inactive, and ON when the regulated current source is coupled to provide a regulated current source. In accordance with FIGS. 7A-7D, the regulated current source formed by transistors 112-124 and the switch provided by transistor 125 are switched ON and OFF on a selective basis so that an electrode coupled to the output of example circuit 110 may operate in an OFF mode, a regulated anode mode, or an unregulated anode mode.

As further shown in FIG. 8, the inputs to circuit 110 are REG_TOP, ATN, V_GATE, I_FDBK, EN_STG1, nEN_STG1, CMN_SRC_EN, EN_OUTPUT, nEN_OUTPUT, and AVSS. REG_TOP, ATN and AVSS are supply inputs. V_GATE and I_FDBK are control inputs that drive elements of circuit 110. EN_STG1, nEN_STG1, EN_OUTPUT, nEN_OUTPUT and CMN_SRC_EN are logic inputs that are used to control the state or mode of circuit 110 during operation, i.e., the off mode, regulated anode mode, or unregulated anode mode. The output of circuit 110 is a regulated current, SRC_OUT, which is applied to a corresponding electrode 48.

In this disclosure, signals with an "n" in front of the pertinent signal label, e.g., nEN_OUTPUT, nEN_STG1, or the like, generally indicate an inverse polarity to signals without the "n" in front of the signal label, e.g., EN_OUTPUT, EN_STG1, or the like. Hence, a signal with the "n" designation is the inverse of the corresponding signal without the "n" designation. For example, nEN_OUTPUT is the inverse of EN_OUTPUT. The state of EN_OUTPUT may be controlled to, in effect, turn circuit 110 ON and OFF, e.g., to deliver stimulation pulses.

REG_TOP is a regulated, positive voltage rail supplied by a regulated power source. As an example, the regulator power source may include a capacitor stack provided by a capacitor module that is charged on a pulse-by-pulse basis. REG_TOP may, for example, have a value of approximately 12 V to 20 V and may be available on a continuous basis or only during stimulation, e.g., upon charging a capacitor circuit to provide the voltage. The value of REG_TOP may vary during operation, e.g., drop to a reduced value from a high value during or after a stimulation pulse is delivered and then recharge to the high value for delivery of the next stimulation pulse. REG_TOP may be used as high reference voltage for sourcing of unregulated current via switch 125 or regulated current via the voltage regulator formed by transistors 112-124. ATN is a regulated high voltage supply rail. ATN may have a higher voltage level than REG_TOP and may remain at a substantially constant level.

The following description refers to example circuit 110 operating in the regulated anode mode. In this mode, transistors 112-124 operate as a regulated current source to output regulated current SRC_OUT. Diodes 126 operate to protect transistor 114 from high voltages in the event of leakage current from transistor 112. When example circuit 110 operates in this mode, transistors 121, 122 and 123 are turned OFF, transistor 124 is turned ON, and transistor 125 is turned OFF. With transistor 125 turned OFF, the current regulator is not bypassed by coupling the electrode to the high reference voltage REG_TOP. The operation of transistors 121-125 is described in greater detail below.

When operating in the regulated anode mode, stimulation control module 62 supplies V_GATE as an input signal. V_GATE may be generated by a digital-to-analog converter (DAC) as a function of a reference source current specified for a given stimulation program. V_GATE may be held constant for a given reference source current to produce a constant current or pulsed current waveform, or vary over time for a varying current waveform. The DAC may be a simple R-2R resistor ladder DAC. Optionally, one, two, or more gain stages may amplify the analog signal produced by the DAC to produce the V_GATE signal for application to transistors 113. Each of the parallel, regulated current source branches receive the same V_GATE signal. If all N parallel, regulated current source branches are ON, the combined current output will be approximately the N times the current through transistor 113. If a different reference current is specified by a program, then the control signal V_GATE changes as a function of the reference current.

Stimulation control module 62 activates a selected number of the multiple, parallel source branches forming a respective regulated current source to produce a specified level of current. The selected number of active branches is based on a percentage or gain ratio assigned to the pertinent electrode. Stimulation control module 62 may store the percentages for each of the regulated current sources 72A-72P in one or more digital control registers, which may form part of stimulation control module 62. The percentage may be individually controlled for each regulated current source and for each stimulation waveform delivered via the current source.

Again, the percentage for a given current source may specify the number of parallel, current source branches that should be activated to scale up (or down) a desired, overall current level for a given current source. The control register maintains programmed percentages for different current sources and sinks so that current can be steered to provide different field patterns and shapes. The DAC and gain stages may form part of stimulation control module 62. When circuit 110 is not operating in the regulated anode mode, stimulation control module 62 may not apply a V_GATE signal to example circuit 110.

Transistors 113 and 114 operate as a current mirror. In particular, transistor 113 controls the operation of transistor 114 by controlling the signal at the gate of transistor 114. The V_GATE signal applied to transistor 114 is a function of the level of the V_GATE signal applied to transistor 113. Accordingly, transistors 113 and 114 may be viewed as a master transistor and a slave transistor, respectively. V_GATE is used to turn transistor 114 ON and OFF to produce a stimulation current signal at a desired level set by V_GATE. In addition, the V_GATE signal may have other characteristics that control the current signal sourced from REG_TOP via transistor 114.

In some implementations, transistors 113 and 114 may be high voltage transistors. However, precisely matching transistors 113 and 114 may be difficult with high voltage transistors. In addition, the drain-to-source voltage $V_{DS}$ of transistor 114 may vary more greatly in a high voltage transistor, and may produce offset in the output current due to decreased output resistance. Accordingly, it may be desirable to use well-matched, lower voltage transistors for transistors 113 and 114, instead of high voltage transistors. In this case, transistor 112 may be provided to operate as a cascode device that protects transistor 114 from high voltages. Due to increased output resistance, there may be a need for additional headroom in the circuit.

An active cascode configuration may be provided to monitor the voltage between transistors 114 and 112, and ensure that it remains stable throughout the operating range of the regulated current source. In particular, the active cascode configuration may ensure that the $V_{is}$ of transistor 113 and the $V_{is}$ of transistor 114 remain substantially equal to one another. In turn, the active cascode configuration may mitigate the ON resistance $R_{on}$ of transistor 114 and improve its output characteristics.

In the example of FIG. 8, transistors 112 and 115-120 operate as an active cascode configuration. Together, transistors 115-120 monitor the voltage between transistor 112 and transistor 114, at the node receiving I_SUM. In operation, a predetermined voltage may be set at SRC_OUT. As the voltage level of a power source, such as a battery, decreases while delivering stimulation, the voltage level of REG_TOP will also decrease. As a result, the output voltage between REG_TOP and SRC_OUT, which is also the voltage drop across transistors 112 and 114, will decrease. When this output voltage decreases, the $V_{DS}$ of transistor 114 will also decrease, causing transistor 116 to begin to turn OFF slightly.

When transistor 116 begins to turn OFF, it causes the $V_{GS}$ of transistor 115 to increase slightly, causing transistor 115 to turn ON slightly more, thereby decreasing the $V_{GS}$ of transistor 117. Consequently, transistor 117 begins to turn OFF slightly, which causes the $V_{GS}$ of transistor 112 to increase, thereby decreasing the $R_{on}$ of transistor 112. In particular, because the $V_{GS}$ of transistor 112 turns ON more, its resistance decreases. The decreased resistance of transistor 112 serves to restore the $V_{DS}$ of transistor 114 at the I_SUM node. Hence, the active cascode configuration may serve to replace voltage on transistor 112, VG_CASC_BIAS, through transistor 117.

The mechanism that moves all of the gate voltages around are the currents produced in the legs coupled to the drain of transistor 115 and the drain of transistor 117. As the transistors in series with these currents begin to turn OFF, the voltages in series are pulled toward the current source (e.g., transistors 119 and 120 as described above). The inverse is also true. When transistors in series with the current source begin to turn ON more, those transistors pull the voltages in series with them toward that transistor's rail (e.g., transistor 115 as described above).

As an alternative, the active cascode configuration may be implemented with the use of only transistor 116, without transistors 115 and 117. However, this design would generally required that transistor 116 be a high voltage device, which would drive the $V_{DS}$ of transistors 113 and 114 further apart, and may generate additional offset current. With transistors 115, 116, and 117, transistor 116 ensures that ISUM (the $V_{DS}$ of transistor 114) is near, if not equal to, the $V_{DS}$ of transistor 113 to provide good matching and no built-in offsets.

Transistors 118-120 set the current for transistors 115-117 based on I_FDBK. I_FDBK is a reference current and may be generated by circuitry at the front end of example circuit 110. In particular, transistor 118 sets the $V_{GS}$ for transistors 119 and 120 which, in turn, sets the current for transistors 115 and 117. In this way, transistors 119 and 120 operate as current sources that control the gate voltages for transistors 115-117. That is, as transistors 116 and 117 that are in series with transistor 120 begin to turn OFF, the voltages in series are pulled toward transistor 120. Similarly, as transistor 115 begins to turn ON, transistor 115 pulls the voltage in series toward its rail, REG_TOP.

In FIG. 8, transistor 114 may represent multiple, e.g., N=sixty-four (64), transistors coupled in parallel with each other. Each parallel transistor 114 receives V_GATE on its respective gate. With respect to transistors 121-125, when circuit 110 is operating in the regulated anode mode, transistors 121, 122 and 123 are not enabled, transistor 124 is enabled, and transistor 125 is not enabled. Control signals EN_STG1, EN_OUTPUT, nEN_OUTPUT, and nEN_STG1 are applied to transistors 122, 123, 124, and 121, respectively, and may be supplied by stimulation control module 62. These control signals are applied to the gates of the corresponding transistors to turn the transistors OFF and ON. Control signal CMN_SRC_EN turns transistor 125 ON or OFF to selectively couple SRC_OUT to the reference voltage REG_TOP to provide an unregulated current path. Transistors 121-125 operate as closed switches when enabled and operate as open switches when not enabled. EN_OUTPUT and nEN_OUTPUT selectively alternate between respective high and low values to cause circuit 110 to deliver regulated current for stimulation pulses at a specified pulse rate, and with specified pulse widths, according to a selected program or programs delivered by stimulation control module 62.

In general, transistors 121 and 122 turn transistors 115-120 and transistor 113 ON and OFF, respectively, transistors 123 and 124 turn transistor 112 ON and OFF, and transistor 125 selectively couples the output SRC_OUT directly to REG_TOP to couple the pertinent electrode to an unregulated current path. When operating in the regulator mode, transistors 121, 122 and 123 are not enabled, transistor 124 is enabled, and transistor 125 is not enabled. In this case, the electrode is coupled to the regulated current path at the output of transistor 112.

When operating in the OFF mode, transistors 121-123 are enabled and transistors 124 and 125 are not enabled. When transistors 121-123 are enabled, i.e., operating as closed switches, the master transistors (transistor 113 and transistors 115-120) are shut off. That is, transistor 113 shuts off such that V_GATE is not applied to the gate of transistor 114 and transistors 118-120 shut off. This, in turn, shuts off transistors 115-117 such that no signal is applied to transistor 115. Transistor 123 is turned ON transistor 124 is turned OFF, thereby decoupling the gate of transistor 112 from VG_CASC_BIAS and coupling it to ATN, which is the highest voltage in the system. In this mode, transistor 125 is also turned OFF.

When operating in the unregulated anode mode, i.e., a reference mode, transistors 121-123 are turned ON (enabled) to turn OFF transistors 115-120 and 113, respectively, and transistor 124 is turned OFF. Thus, transistor 112 generates substantially no signal at the output. At the same time, transistor 125 is turned ON, coupling the high reference voltage REG_TOP to the output, SRC_OUT. Consequently, the output applies an unregulated positive reference voltage to the corresponding electrode to provide an unregulated current path for sourcing current via the electrode.

In the example of FIG. 8, transistors 112-125 may be implemented using N-type and P-type MOSFET transistors configured to operate in a depletion mode. It should be understood, however, that circuit 110 may be implemented using various types and configurations of transistors. The gate width and length sizes of transistor 112 and transistor 125 may be substantially the same in some examples because both transistors may be designed to handle the full output current value. The addition of transistor 125 may require additional chip real estate on existing footprints.

Figure 9:
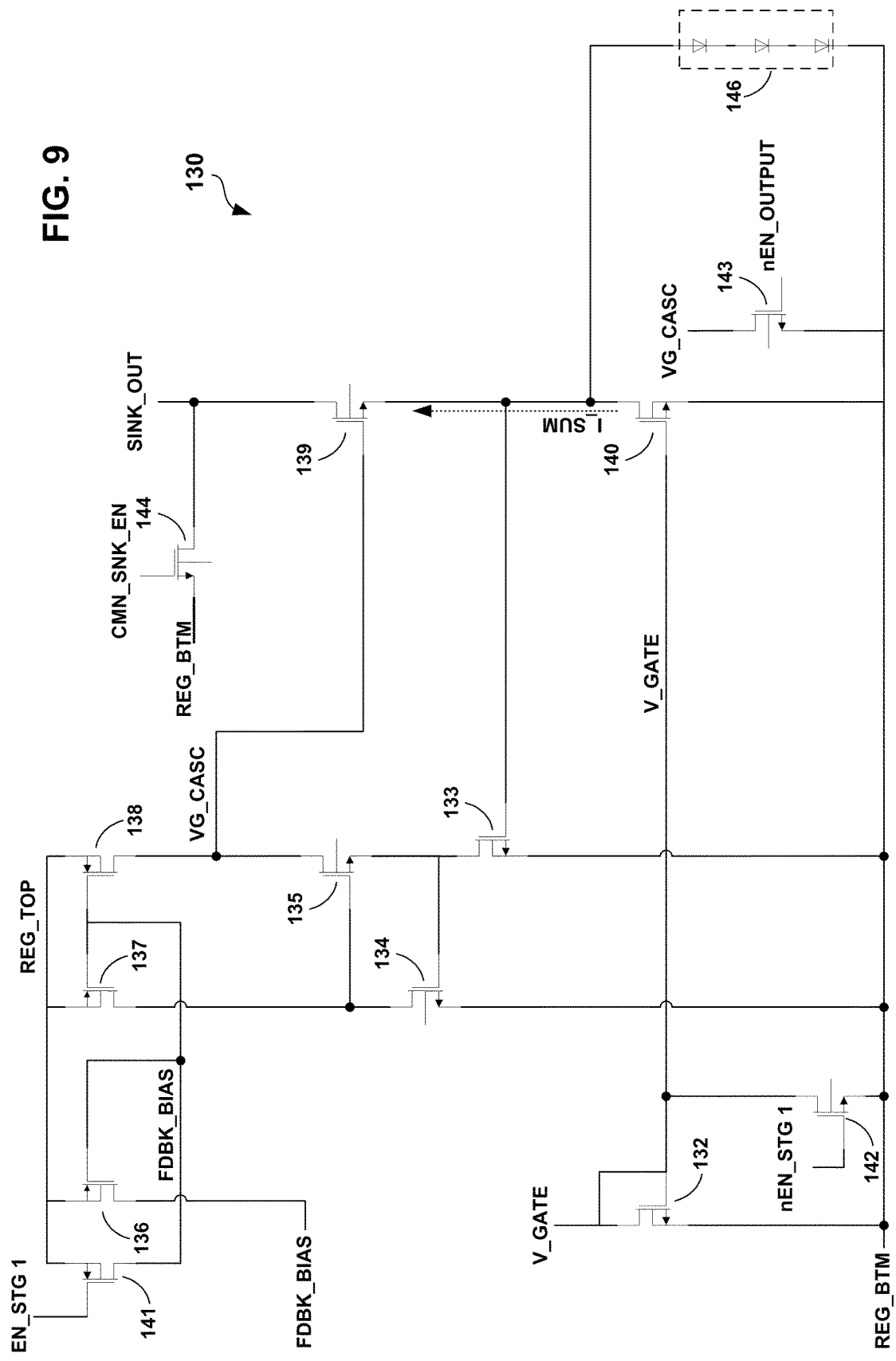

FIG. 9 is a schematic circuit diagram illustrating an example circuit 130 that may be used to implement regulated current sinks 74A-74P in FIGS. 6 and 7A-7D. In particular, transistors 132-143 are configured to operate as one of regulated current sinks 24A-P, receive a regulated current from the electrode coupled to the output based on a reference input current. Accordingly, transistors 132-143 may be referred to as a regulated current sink. Diodes 146 operates to protect transistor 140 from high voltages in the event of leakage current from transistor 139. Transistor 144 operates as a switch for coupling the output of example circuit 130 to a low reference voltage. Hence, when closed, transistor 144 also couples the electrode to the reference voltage REG_BTM. The regulated current sink and transistor 144 may be switched ON and OFF to configure example circuit 130 for operation in an OFF mode, a regulated cathode mode, and an unregulated cathode mode.

The inputs to circuit 130 in the example of FIG. 9 are REG_TOP, REG_BTM, V_GATE, FDBK_BIAS, V_GATE, EN_STG1, nEN_STG1, VG_CASC, nEN_OUTPUT, and CMN_SNK_EN. REG_TOP are REG_BTM are supply inputs. V_GATE and FDBK_BIAS are control inputs that drive the elements of circuit 130. As in the example of FIG. 8, EN_STG1, nEN_STG1, and CMN_SNK_EN are logic inputs that are used to control the state or mode of circuit 130 during operation. The output of circuit 130 is SINK_OUT, which is applied to a corresponding electrode.

REG_TOP and REG_BTM are positive and negative voltages supplied by a regulated power source. REG_TOP, as discussed with reference to FIG. 8 may be used as a high reference voltage level. REG_BTM may be used as a low reference voltage level. REG_TOP and REG_BTM may each, for example, have a value of approximately ±12 V or ±20 V, respectively, and may be generated continuously or only during stimulation by a voltage regulator. The value of REG_TOP and REG_BTM may vary during operation, e.g., drop from a nominal value after a stimulation pulse is delivered and then recover to the nominal value for delivery of the next pulse. In some examples, REG_BTM need not be a negative voltage and may instead by a ground or other reference voltage.

Example circuit 130 will first be described operating in the regulated cathode mode to output a regulated sink current SINK_OUT. In the regulated cathode mode, transistors 141 and 143 are turned OFF, and transistor 144 is turned OFF. In this configuration, transistors 132-140 sink a regulated current from the electrode coupled to the output current SNK_OUT.

FIG. 9 also utilizes a current mirror with an active cascode configuration and, in this sense, may operate in a manner similar to FIG. 8. Similar to FIG. 8, in circuit 130 of FIG. 9, stimulation control module 62 supplies input signal V_GATE to transistor 132. Stimulation control module 62 may not apply V_GATE to circuit 130 if circuit 130 is operating in the unregulated mode. V_GATE may be generated by a digital-to-analog converter (DAC) and be amplified by one or more gain stages, resulting in an analog signal that would be sufficient to cause the regulated current sink to sink a specified reference current level when the percentage, i.e., gain ratio, is 100 percent. Again, the V_GATE signal may be selected as a function of the reference current, and the regulated current sink may comprise multiple, regulated current sink branches.

A single V_GATE signal may be specified for sources and sinks, or separate V_GATE signals may be used for sources and sinks. As described with reference to circuit 110 of FIG. 8, for circuit 130 of FIG. 9, the regulated current sink may represent a number of parallel, regulated current sink branches that may be selectively activated to scale up or down to a desired current level as a percentage of the reference current. For example, each regulated current sink 74A-74P may include 64 parallel current sink branches, each providing $1/64^{th}$ of the reference current level.

Transistors 132 and 140 are configured to operate as a current mirror in which transistor 132 controls the output of transistor 140. In FIG. 9, V_GATE is used to turn transistor 140 ON and OFF to sink current based on V_GATE. Because transistor 132 controls the operation of transistor 140, transistors 132 and 140 may be viewed as master and slave transistors, respectively. Again, transistors 132 and 140 may be selected to be well matched to each other since cascode transistor 139 is provided to protect transistors 132 and 140 from high voltages at SNK_OUT.

In general, transistors 133-139 form an active cascode configuration for controlling the current that sinks through transistor 139, i.e., I_SUM, so that the $V_{DS}$ for transistors 140 and 132 is substantially the same. As previously described with respect to FIG. 10, the active cascode is required because the voltage drop between transistors 139 and 140 decreases proportionately as REG_BTM decreases when stimulation is delivered. When this happens, the $V_{DS}$ of transistor 139 decreases causing transistor 133 to begin to turn OFF.

Consequently, the $V_{GS}$ of transistor 134 increases causing transistor 134 to turn ON, thereby decreasing the $V_{GS}$ of transistor 135. This begins to turn transistor 135 OFF, which causes the $V_{GS}$ of transistor 139 to increase. Because transistor 139 turns ON more, its resistive value decreases and restores voltage at I_SUM, replacing voltage VG_CASC on transistor 140.

Transistors 136-138 set up the current applied to transistors 133-135 based on the reference input current FDBK_BIAS. FDBK_BIAS may be generated using circuitry at the front end of example circuit 130. In particular, transistors 136 and 137 set the current for transistor 134 and transistor 138 sets the current for transistors 133 and 135.

Circuit 130 may be implemented using other configurations, such as the alternative configurations previously discussed with respect to FIG. 8. For example, circuit 130 may be configured to include a current mirror with high voltage transistors. As another example, circuit 130 may be configured to include two well matched transistors to operate as a current mirror and a cascode device that protects the current mirror from high voltages including a transistor connected in series with the output transistor and a high voltage transistor.

When operating in a regulated cathode mode, transistors 141 and 143 are turned OFF, and transistor 144 is turned OFF. With transistors 141 and 142 turned OFF and transistor 143 turned ON, transistor 132 controls the operation of transistor 140 and transistors 133-138 form an active cascode for controlling transistor 139. Because transistor 144 is also turned OFF, SINK_OUT sinks current through transistor 139. The signal nEN_OUTPUT selectively alternates between a high and low value to cause circuit 130 to deliver regulated current for stimulation pulses at a specified pulse rate, and with specified pulse widths, according to a selected program or programs delivered by stimulation control module 62.

However, when operating in an OFF mode, transistor 141 is turned ON, and transistor 144 is turned OFF. V_GATE is shorted to REG_BTM and FDBK_BIAS is shorted to REG_TOP when transistors 141 and 142 are turned ON. In addition, the gate of transistor 139 is decoupled from transistors 135 and 138 and the output SINK_OUT is not coupled to REG_BTM. Consequently, in the OFF mode, SINK_OUT does not sink substantial current from the corresponding electrode.

Example circuit 130 operates in an unregulated cathode mode when transistor 144 is turned ON, transistors 141-143 are turned ON. Because SINK_OUT is coupled to the low reference voltage REG_BTM through transistor 144 in this case, REG_BTM provides an unregulated current path to sink current from the corresponding electrode.

Control signals EN_STG1, EN_OUTPUT, and nEN_STG1 are applied to transistors 141, 143, and 142, respectively, and may be supplied by stimulation control module 62. These control signals are applied to the gates of the corresponding transistors to turn the transistors OFF and ON. Control signal CMN_SNK_EN turns transistor 144 ON or OFF to selectively couple SINK_OUT to the lower reference voltage REG_BTM to provide an unregulated current path.

Similar to FIG. 8, transistors 132-144 in FIG. 9 may be implemented using N-type and P-type MOSFET transistors configured to operate in a depletion mode, although circuit 130 may be implemented using various types and configurations of transistors. The size of transistor 139 and transistor 144 may be substantially the same because both transistors may be designed to handle the full output current value. The size of transistor 144 may present additional chip real estate for existing footprints.

Figure 10A:
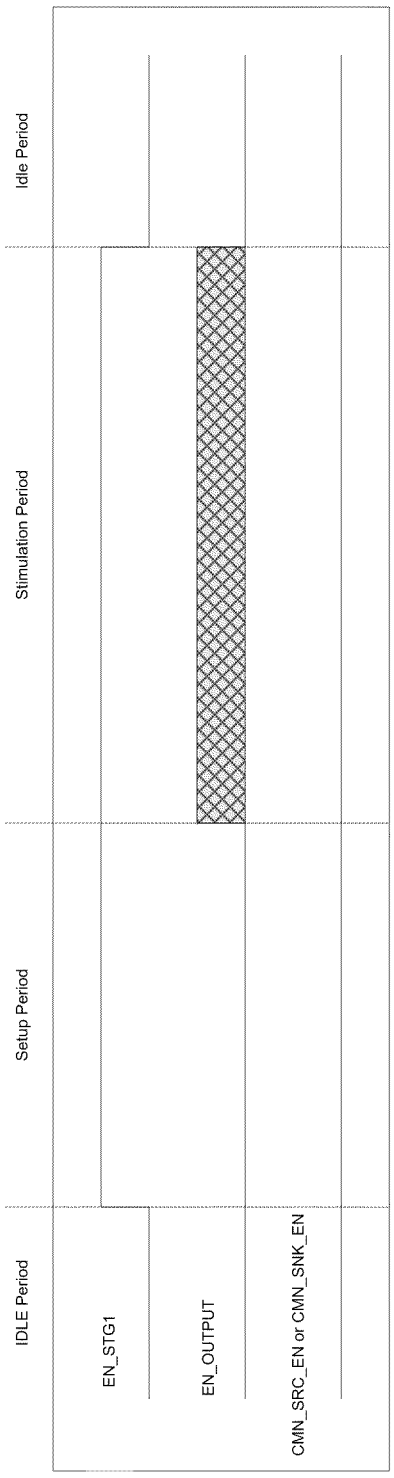
FIGS. 10A and 10B are timing waveforms for the example circuitry shown in FIGS. 8 and 9.
Figure 10B:
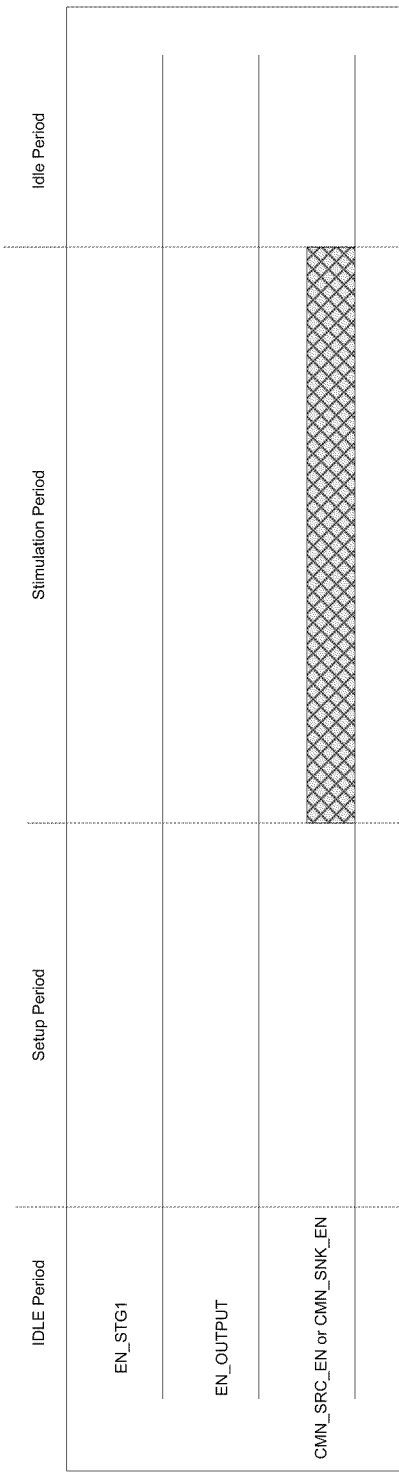

FIGS. 10A and 10B illustrate timing waveforms for example circuit 110 (FIG. 8) and example circuit 130 (FIG. 9) operating, respectively, in a regulated electrode mode and an unregulated reference mode while delivering stimulation. The timing waveforms shown in FIGS. 10A and 10B include EN_STG1, EN_OUTPUT, and CMN_SRC_EN (circuit 110) or CMN_SNK_EN (circuit 130), as generated by stimulation control module 62. The timing waveforms for these signals are shown over a time period including an initial idle period, a setup period, a stimulation period, and a final idle period.

In particular, FIG. 10A illustrates timing waveforms for example circuits 110 and 130 delivering stimulation while operating in a regulated electrode mode. In the case of source circuit 110, FIG. 10A illustrates operation in a regulated anode mode. For sink circuit 130, FIG. 10B illustrates operation in a regulated cathode mode. During an initial idle period, all of the control signals are low and no signal is provided to the input or the output of example circuits 110 and 130.

EN_STG1 goes high over the setup period, turning ON the master transistors and active cascode transistors in example circuits 110 and 130. During the stimulation period, EN_STG1 stays high and EN_OUTPUT goes high over the stimulation period, according to a selected program or programs delivered by stimulation control module 62.

When EN_OUTPUT goes high, the active cascode transistors are coupled to the gate of the output transistor, i.e., transistors 115-120 are coupled to the gate of transistor 112 in circuit 110 (FIG. 8) and transistors 133-138 are coupled to the gate of transistor 139 in circuit 130 (FIG. 9). Thus, EN_OUTPUT turns ON the output transistor so that circuits 110 and 130 may source and sink current, respectively. Because EN_STG1 was high during the prior setup period, the signal controlling the output transistors may effectively turn the output transistor full ON at the beginning of the stimulation period. EN_STG1 and EN_OUTPUT return to a low value during the final idle period, effectively turning OFF current source circuit 110 or current sink circuit 130, as applicable.

FIG. 10B illustrates timing waveforms for example circuits 110 and 130 for delivering stimulation therapy while operating in an unregulated, reference mode. During the initial idle period and the setup period, EN_STG1, EN_OUTPUT, and CMN_SRC_EN (for source circuit 110) or CMN_SNK_EN (for sink circuit 130) remain low. Over the stimulation period, CMN_SRC_EN (for source circuit 110) or CMN_SNK_EN (for sink circuit 130) go to an active state to couple circuits 110 and 130 to an unregulated high reference value (REG_TOP) for source circuit 110 and an unregulated low reference value (REG_BTM) for sink circuit 130, respectively, during a stimulation period. CMN_SNK_EN and CMN_SRC_EN cause circuits 130, 110, respectively, to deliver unregulated current for a specified stimulation period, according to a selected program or programs delivered by stimulation control module 62. The level of CMN_SRC_EN or CMN_SNK_EN returns to a low value during the final idle period to return to operation in an off mode.

Figure 11:
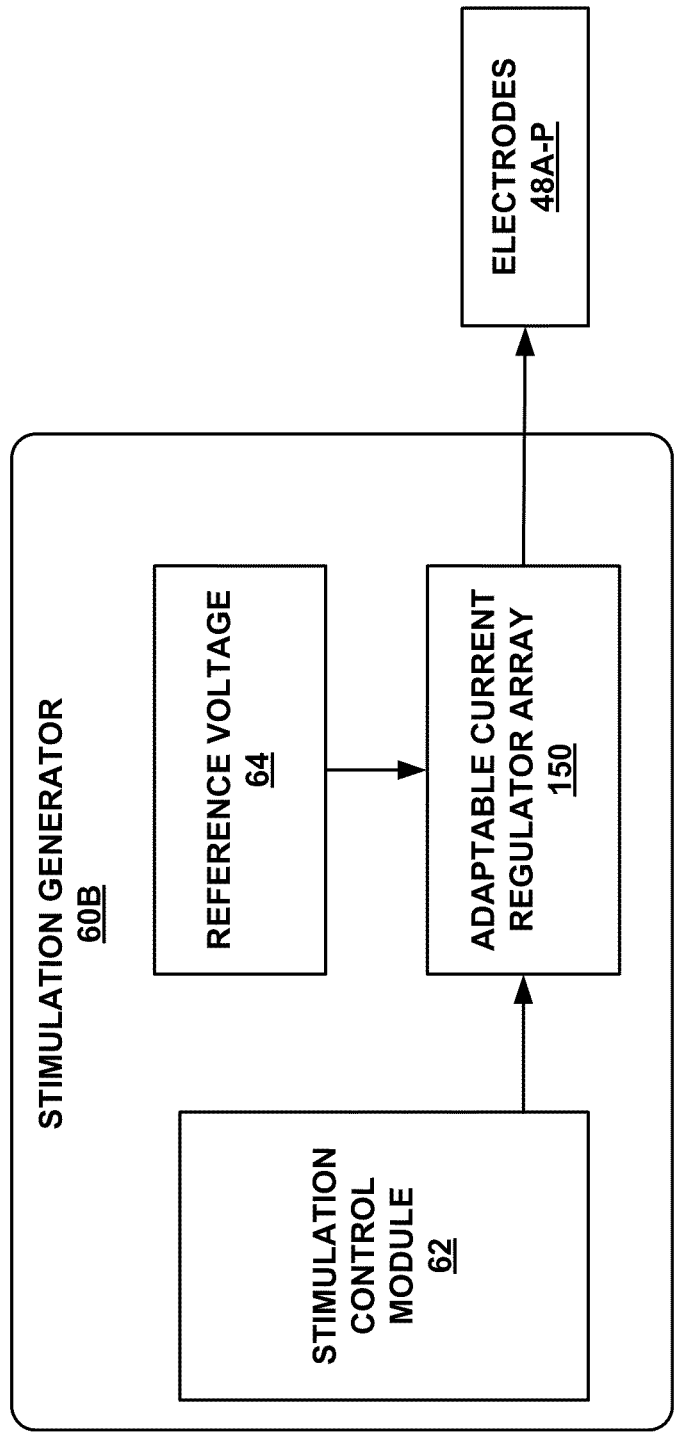
FIG. 11 is a block diagram illustrating various components of another example stimulation generator for use in the implantable electrical stimulator of FIG. 3.

FIG. 11 is a block diagram illustrating various components of an alternative stimulation generator 60B according to another example embodiment of the disclosure. Stimulation generator 60B may be used with an implantable stimulator, e.g., to perform the functions of stimulation generator 60 as described with reference to FIGS. 1-3. Although stimulation generator 60B in FIG. 11 is described with respect to implantable stimulator 4, stimulation generator 60B may also be used for implantable stimulator 34, or with other types of stimulators. In general, stimulation generator 60B provides an alternative implementation in which a regulated current source is adaptable to source or sink regulated current via a regulated current path, or to couple an electrode to a high or low reference voltage via an unregulated current path.

Stimulation generator 60B shown in FIG. 11 may support sourcing and sinking of regulated current in a manner similar to stimulation generator 60A as described with respect to FIG. 5. That is, stimulation generator 60B shown in FIG. 11 may provide individual control of electrodes 48A-49P, so that individual electrodes can be selectively used as a regulated current source, a regulated current sink, an unregulated reference electrode (i.e., unregulated anode or cathode) for balancing charge produced by regulated electrodes during stimulation, or as an inactive electrode when not in use. However, stimulation generator 60B in FIG. 11 includes, in addition to stimulation control module 62, an adaptable current regulator array 150 instead of regulated current regulator array 68 and switch array 66. Stimulation control module 62 may selectively control individual regulated current sources or sinks in array 150 to delivery stimulation via selected electrodes, e.g., as stimulation current pulses.

Adaptable current regulator array 150 includes a plurality of adaptable current sources, each of which is coupled to a corresponding one of electrodes 48A-48P. Each adaptable current regulator may operate as a regulated current source or regulated current sink, or as a switch that couples the corresponding electrode 48A-48P to a reference voltage via an unregulated current path. Thus, adaptable current sources in array 150 may operate in an off mode, a current regulated mode, or an unregulated mode on a selective basis.

Stimulation control module 62 controls adaptable current regulator array 150 to selectively operate in a current regulated or current unregulated mode. In particular, stimulation control module 62 controls adaptable current regulator array 150 to deliver stimulation via electrodes 48A-48P in accordance with one or more selected programs received from processor 50. Any given program specifies an electrode combination, i.e., electrodes selected to deliver stimulation and their polarities, as well as the rate, pulse width, and amplitude of the stimulation. Thus, stimulation control module 62 configures each adaptable current regulator of array 150 to operate in either a regulated mode, an unregulated, reference mode, or an off mode in accordance with the selected program. As previously described, reference voltage 64 may be provided by a regulated power source having a voltage regulator that outputs a substantially constant voltage. An adaptable current regulator of array 150 may use the reference voltage 64 to generate a substantially constant current when operating in a regulator mode.

For example, a selected program may specify one of electrodes 48 as an unregulated, reference electrode and two or more other electrodes 48 as regulated anode or cathode electrodes. In this example, stimulation control module 62 configures the appropriate adaptable current regulator of array 150 to operate in a reference mode and a regulator mode, respectively. Stimulation control module 62 configures the remaining adaptable current regulators of array 150, i.e., the adaptable current regulators associated with electrodes 48 not specified by the selected programs, to operate in an off mode.

As mentioned previously, in example electrode configurations having an unregulated cathode and a regulated cathode, the cathode that sinks the greatest amount of current in the specified electrode configuration may be selected as the unregulated cathode during the programming process. The unregulated cathode may then be coupled to a reference voltage having the lowest potential relative to the potentials of other electrodes in the electrode configuration. This allows the regulated cathode to use voltage built up from the low reference voltage. In some examples, the unregulated cathode that is selected to provide the unregulated current path need not sink the highest amount of current. If the impedance of the unregulated cathode is greater than the impedance of the regulated cathode(s), for example, the unregulated cathode may present a lower potential than the regulated cathodes, even though a lower current may be applied via the unregulated cathode. Hence, in order to gain efficiency, the unregulated cathode may be selected as the cathode that presents the lowest potential, as a function of the cathode impedance and the current level that will be sunk by the unregulated cathode, in order to reduce the difference between the highest and lowest potentials needed to produce the desired current output. As an illustration, if a regulated cathode sinks 6 mA at an impedance of 500 ohms, the regulated cathode presents a potential of −3 V. The unregulated cathode may be selected such that it sinks 4 mA at an impedance of 1000 ohms, thereby presenting a potential of −4 V. Thus, the unregulated cathode presents a lower potential than the regulated cathode.

In example configurations in which the unregulated electrode is an anode and the electrode combination has more than one anode, the unregulated electrode may be selected to be the anode that sources the highest amount of current. In this manner, the regulated anode(s) can balance the current using voltage sources that are lower than the reference voltage to which the unregulated anode is selectively coupled. Whether the unregulated electrode is an anode or a cathode, the selective use of an unregulated reference voltage can reduce power consumption during operation of the electrical stimulator. In some examples, the unregulated anode that is selected to provide the unregulated current path need not source the highest amount of current. If the impedance of the unregulated anode is greater than the impedance of the regulated anode(s), for example, the unregulated anode may present a higher potential than the regulated anodes, even though a lower current may be applied via the unregulated anode. Hence, in order to gain efficiency, the unregulated anode may be selected as the anode that presents the highest potential, as a function of the anode impedance and the current level that will be sourced by the unregulated anode, in order to reduce the difference between the highest and lowest potentials needed to produce the desired current output. As an illustration, if a regulated anode sources 6 mA at an impedance of 500 ohms, the regulated anode presents a potential of 3 V. The unregulated anode may be selected such that it sources 4 mA at an impedance of 1000 ohms, thereby presenting a potential of 4 V. Thus, the unregulated anode presents a higher potential than the regulated anode.

FIG. 12 is a block diagram illustrating various example components of stimulation generator 60B shown in FIG. 13 in greater detail. In particular, FIG. 12 shows adaptable current source array 150 in greater detail. It should be understood that FIG. 12 is intended as a conceptual diagram for the purpose of illustrating the functionality of stimulation generator 60B. Thus, for ease of illustration, not all power and logic signals and/or connections are shown in FIG. 12.

As shown in FIG. 12, adaptable current source array 150 includes adaptable current regulators 152A-P (collectively "adaptable current sources 152") each of which is coupled to a respective one of electrodes 48A-P. Adaptable current regulators 152 may also be referred to as adaptable bidirectional current regulators 152 because each of adaptable current regulators 152 may be configured as a regulated current sink or a regulated current source. Accordingly, each of adaptable current regulators 152 (adaptable bidirectional current regulators 152) includes a corresponding one of adaptable current sources 154A-P (collectively "adaptable current sources 154") and adaptable current sinks 156A-P (collectively "adaptable current sinks 156").

Each of adaptable current sources 154 and adaptable current sinks 156 may be configured to operate as a regulator that sources or sinks regulated current or, in effect, as a switch that couples the corresponding one of electrodes 48 to a high or low reference voltage via an unregulated current path. In operation, stimulation control module 62 configures each of adaptable current sources 154 and adaptable current sinks 156 as needed according to a program or programs received from processor 50. If a program specifies that a given electrode 48A is to function as a regulated cathode, for example, then stimulation control module 62 controls adaptable current sink 156A to sink current from electrode 48A to the low reference voltage.

If a program specifies that a given electrode 48A is to function as an unregulated cathode, then stimulation control module 62 controls adaptable current sink 156A to couple electrode 48A to the low reference voltage without providing current regulation. Generally, at any given time, each bidirectional adaptable current regulator 152A-152P may be configured to operate as a regulated current source, a regulated current sink, an unregulated current source, or an unregulated current sink. In this way, stimulation control module 62 may provide individual control of operation of electrodes 48 for delivering stimulation according to various embodiments of the disclosure.

Although the configuration of stimulation generator 60B shown in FIGS. 11 and 12 operates in a manner similar to the configuration of stimulation generator 60A shown in FIGS. 5 and 6, the stimulation generator 60B shown in FIGS. 11 and 12 may have particular advantages. For example, adaptable current sources 154 and adaptable current sinks 156 may be implemented on a smaller area of a chip than the combination of regulated current sources 73 (FIG. 6), regulated current sinks 75 (FIG. 6), and switches 78 and 79 (FIG. 6). This is because adaptable current sources 154 and adaptable current sinks 156 use the same output transistor to carry the output current, whether operating in a regulated mode or unregulated mode.

Hence, the additional switches 78, 79 used in the stimulation generator 60A can be eliminated in stimulation generator 60B. Stimulation generator 60B makes use of adaptable current sources 154 and sinks 156 that perform functions of both a regulated and unregulated current path. There is no need for a separate unregulated current path in stimulation generator 60B, as would otherwise be provided in the example of stimulation generator 60A. Rather, in stimulation generator 60B, the same output transistor or transistors can be used to carry the output current when operating as a current regulator and when operating, in effect, as a switch that couples the corresponding electrode to an unregulated reference voltage.

In contrast, circuits 110 and 130 use one output transistor to carry the output current when operating in a regulator mode (transistors 112 and 130 in FIGS. 8 and 9, respectively), and a different output transistor to carry the output current when operating in an unregulated, reference mode (transistors 125 and 139 in FIGS. 8 and 9, respectively). The smaller size of adaptable current sources 154 and adaptable current sinks 156 achieved by eliminating additional switches for unregulated operation may be desirable when implementing sources 154 and sinks 156 on chip footprints with little available real estate. Hence, in some embodiments, stimulation generator 60B may permit regulated and unregulated operation of selected electrodes without substantially increasing chip size.

Individual pairs of regulated current sources 154A-154P and sinks 156A-156P may together form bidirectional current sources for respective, individual electrodes 48A-48P. As in the example of FIG. 6, in some cases, each adaptable current regulator 152, in the form of regulated current source 154A-154P or regulated current sink 156A-156P of FIG. 12, may be implemented as a plurality of adaptable, regulated current sources and sinks (x N), respectively, operating in parallel to produce a combined, programmable current level sufficient for a desired stimulation therapy. An adaptable, regulated current source 154A may be implemented by several parallel, adaptable current sources (x N) having identical or similar structures. Similarly, an adaptable, regulated current sink 156A may be implemented by several parallel, adaptable current sinks (x N) having identical or similar structures.

By activating a selected number of the parallel, adaptable regulated current sources forming a regulated current source 154A, stimulation control module 62 may control an amount of regulated source current delivered to a given electrode 48A coupled to the respective current source. Similarly, by activating a selected number of parallel, regulated current sinks forming a regulated current sink 156A, stimulation control module 62 may control an amount of regulated sink current delivered from a given electrode 48A coupled to the respective current sink. As one example, a regulated current source 154A may be implemented as sixty-four (64) parallel, regulated current sources, each delivering a fraction of the total regulated current to be sourced by electrode 48A for a given reference current.

Hence, a regulated current source 154A may be implemented as N parallel, regulated current sources, each delivering a fraction of a total regulated current to be sourced by electrode 48A. Similarly, a regulated current sink 156A may be implemented as N parallel, regulated current sinks, each sinking a fraction of a total regulated current to be sunk by electrode 48A. The outputs of the parallel, adaptable current sources are coupled to electrode 48A such that the electrode receives a sum of the regulated currents produced by the multiple, parallel current sources. In the unregulated mode, multiple, parallel current sources may be adapted to provide multiple, parallel, unregulated paths between the high reference voltage and electrode 48A. A similar arrangement can be provided for current sinks 156A-156P. Hence, the representation of a single, adaptable source or sink in FIG. 12 is provided for purposes of illustration, and may represent implementation with either a single source or sink or multiple, parallel sources or sinks.

Figure 13B:
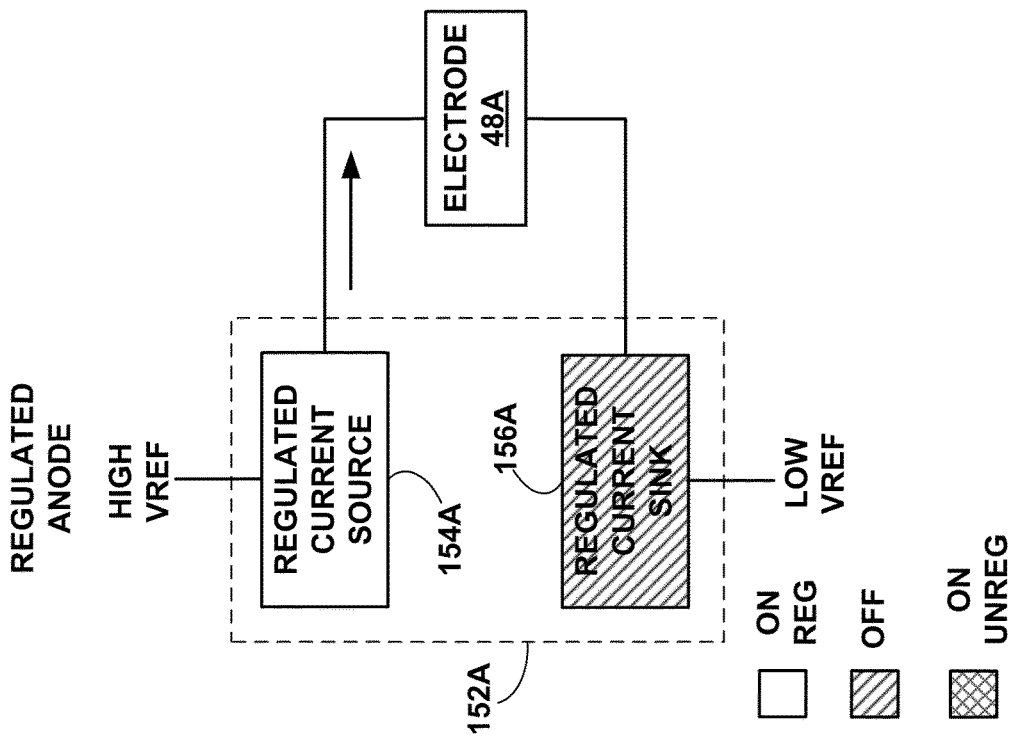
Figure 13A:
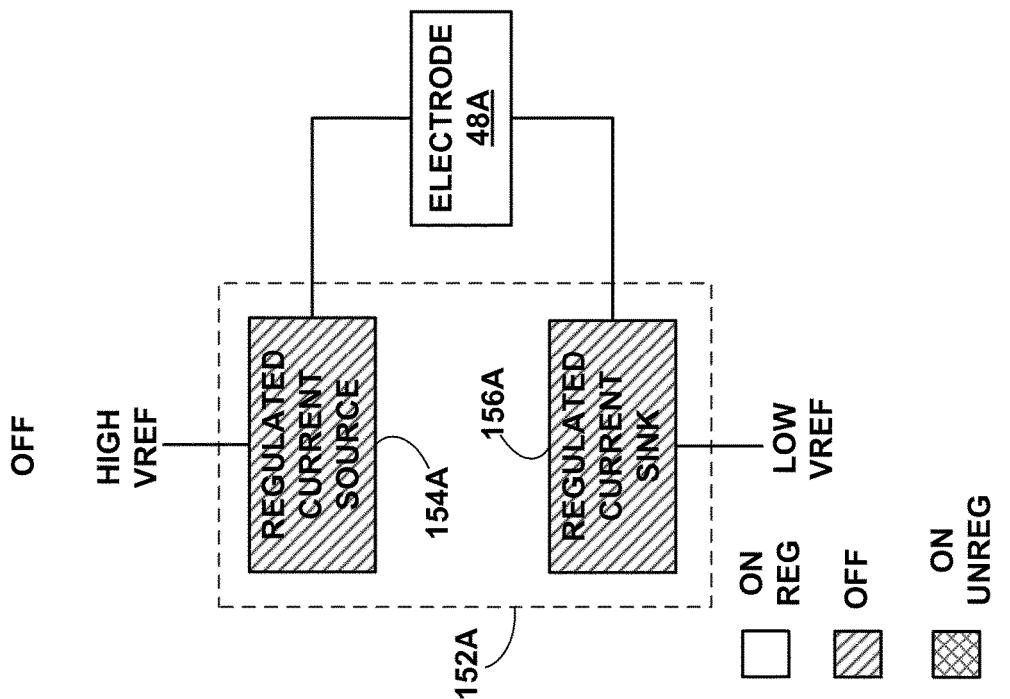

FIGS. 13A-13D are block diagrams illustrating operation of a stimulation generator 60B shown in FIGS. 11 and 12 in producing different regulated and unregulated electrode configurations. The example of FIG. 13A represents an off or inactive state in which an electrode 48A does not form an active electrode in the present electrode configuration. In this case, adaptable, regulated current source 154A and adaptable, regulated current sink 156A are both OFF, as indicated by the hatching. Consequently, electrode 48A is not coupled to the high reference voltage or low reference voltage, or to any other circuit potential, and instead is in a floating state.

FIG. 13B represents a regulated anode state in which electrode 48A is coupled to adaptable, regulated current source 154A, operating in an active, regulator mode, to source regulated current. In this example, adaptable, regulated current sink 156A is inactive. FIG. 13C represents a regulated cathode state in which electrode 48A is coupled to adaptable, regulated current sink 156A, operating in an active, regulator mode, to sink regulated current. In this example, regulated current source 154A is inactive.

FIG. 13D represents an unregulated anode state in which electrode 48A is coupled to the high reference voltage via adaptable, regulated current source 154A, operating as an unregulated current path, to source unregulated current from the high reference voltage. When operating as an unregulated current path between electrode 48A and the high reference voltage, current source 154A may be configured to function like a switch. The unregulated, switch mode of current source 154A is indicated in FIG. 13D by crosshatching. In this example, regulated current sink 156A is inactive. Although not shown in FIGS. 13A-13D, an unregulated cathode state is another possible configuration for electrode 48A. In this case, electrode 48A is coupled to the low reference voltage to sink unregulated current via an unregulated current path provided by current sink 156 when adapted to operate as a switch.

Configuration of electrode 48A, as shown in FIGS. 13A-13D, in conjunction with configuration of other electrodes 48A-48P, may be used to define a variety of different electrode configurations without the need for additional switches. Instead, each regulated current source or sink may be adaptable to operate as either a regulated current path or an unregulated current path. Again, such electrode configurations may include combinations of regulated electrodes that produce unbalanced current distributions, and one or more unregulated electrodes that source or sink unregulated current from and to a high or low reference voltage, respectively, to restore a charge balance among the electrodes, as needed.

When operating in a regulated mode, a current source or sink provides a specified amount of current, e.g., as specified by a V_GATE control input applied by a DAC to the source or sink. When operating in an unregulated mode, the current source or sink operates like a simple switch to couple an electrode to a high or low reference voltage, as applicable, without significant, active current regulation. In some embodiments, all of electrodes 48A-48P may be coupled to adaptable current sources and sinks. In other embodiments, some of the electrodes 48A-48P may be coupled to adaptable current sources and sinks, while other electrodes are coupled to non-adaptable current source and sinks, or to reference voltages.

Figure 14:
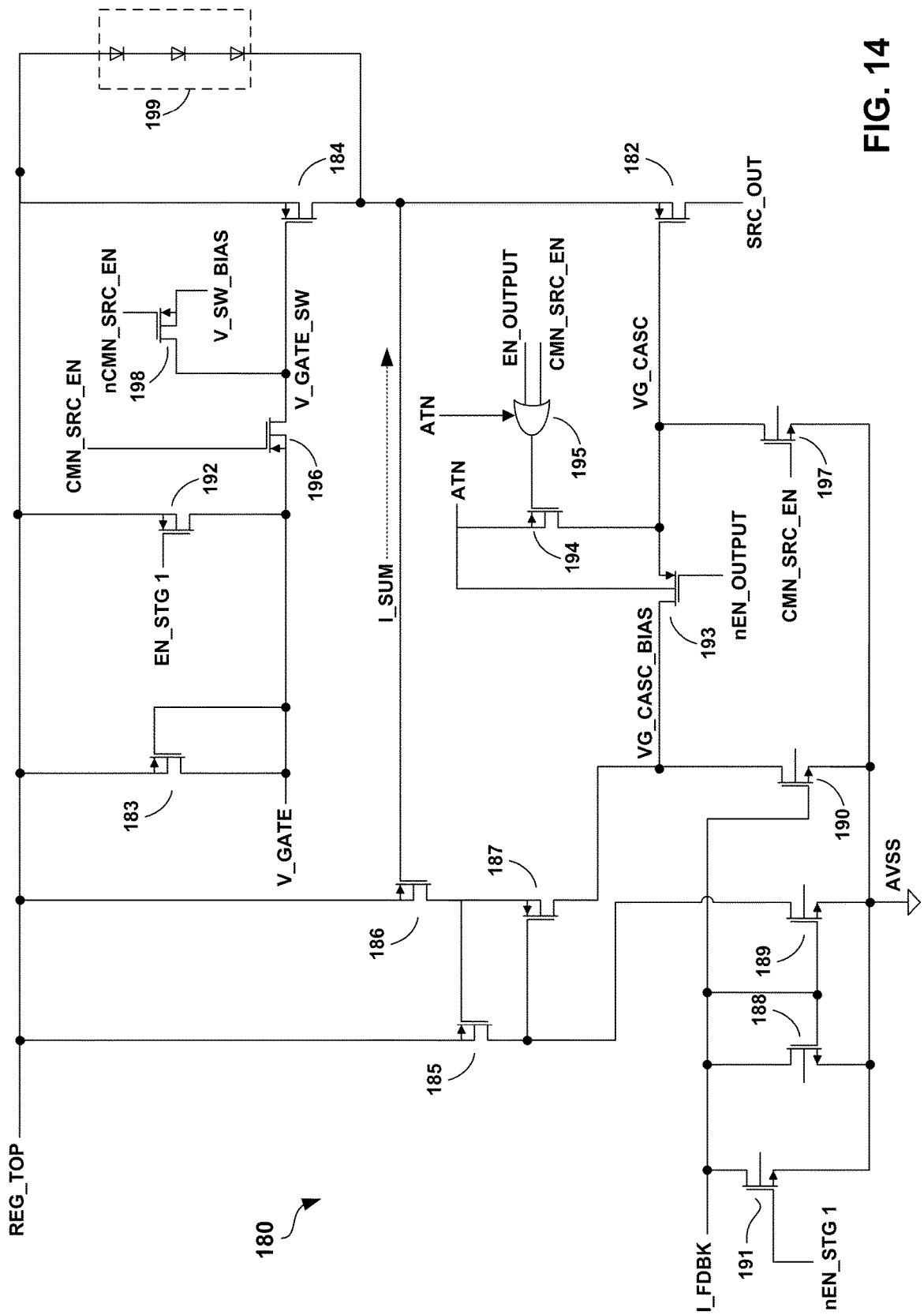
FIGS. 14 and 15 are circuit diagrams illustrating example circuitry for use in the stimulator generator shown in FIGS. 11 and 12.

FIG. 14 is a circuit diagram illustrating an example circuit 180 that may be used to implement stimulation generator 60B as shown in FIGS. 12 and 13A-13D. In the example of FIG. 14, transistors 182-198 are configured and arranged to operate as one of adaptable current sources 154 shown in FIG. 12. Diodes 199 operate to protect transistor 184 from high voltages in the event of leakage current from transistor 182. As described with reference to circuit 110 of FIG. 8, for circuit 180 of FIG. 14, the adaptable current source may represent a number of parallel, adaptable current sink branches that are selectively activated to scale up or down to a desired current level as a percentage of a reference current. Circuit 180 shows one of these branches. Each regulated current source may include 64 parallel current sink branches, each providing $1/64^{th}$ of the reference current level.

The inputs to the example circuit 180 are REG_TOP, ATN, V_GATE, I_FDBK, EN_STG1, V_SW_BIAS, nEN_STG1, EN_OUTPUT, CMN_SRC_EN, nCMN_SRC_EN, as well as AVSS, and nEN_OUTPUT. REG_TOP, ATN, and AVSS are supply inputs that drive the elements of circuit 180. V_GATE and I_FDBK are control inputs that drive various components of circuit 180. EN_STG1, nEN_STG1, EN_OUTPUT, nEN_OUTPUT, CMN_SRC_EN, and nCMN_SRC_EN are logic inputs that are used to control the operation of circuit 180 as a regulator or as a switch that couples a corresponding electrode to unregulated high reference voltage, e.g., REG_TOP.

Some of these inputs are used to turn circuit 180 off when the corresponding electrode is not in use. Accordingly, transistors 191-198 are used as switches for controlling the mode of operation of circuit 180. Transistors 191 and 192 may function as enable switches used to turn master transistors 188, 183, respectively, OFF and ON. Transistors 193 and 196 may function as isolation switches to isolate transistors 182, 184 from a front end of the circuit. Transistors 197 and 198 may function as reference switches that bias transistors 182, 184, respectively, during unregulated operation. The isolation and reference transistors may be operated in a coordinated manner to selectively operate the adaptable current source as a regulated current source or as a switch that couples the corresponding electrode to a reference voltage via an unregulated current path. In particular, isolation transistors 193, 196 and reference transistors 197, 198 may function to selectively tie transistors 182, 184 into the current mirror and activate cascode circuitry for regulated current delivery, or separate transistors 182, 184 from such circuitry for unregulated current delivery from REG_TOP. The output of circuit 180 is SRC_OUT and is applied to a corresponding electrode.

Similar to FIG. 8, REG_TOP in FIG. 14 is a higher reference voltage supplied by a regulated power source that may vary during operation. AVSS may be a controlled low voltage supply that remains substantially constant and may be provided by a regulated power source. ATN may be a high voltage supply rail that remains substantially constant and may provide a higher voltage potential than REG_TOP or AVSS. V_GATE is an analog input signal supplied by stimulation control module 62 when circuit 180 is operating as a current regulator. As in the examples of FIGS. 8 and 9, the V_GATE signal may be generated as a function of a reference current specified for each regulated current source.

If all N parallel branches are operating, the V_GATE signal will cause the voltage regulator to produce a combined current level that is approximately equal to the reference current level. Again, a percentage assigned to each active electrode may be used to scale up or scale down the number of active parallel, adaptable regulator branches in a given current regulator to produce a desired fractional current level. Stimulation control module 62 may not supply V_GATE to circuit 180 when circuit 180 is operating as a switch or is not used for delivering stimulation.

The following description refers to the operation of circuit 180 in an adaptable manner as either a current regulator or a switch. The timing waveforms for the control signals for the regulated and unregulated modes of an adaptable, regulated source or sink, respectively, are provided in FIGS. 16A and 16B.

Control signals EN_STG1, CMN_SRC_EN, nCMN_SRC_EN, nEN_STG1, and nEN_OUTPUT control transistors 192, 196 and 197, 198, 191, and 193, respectively. Or gate 195 applies a control signal to transistor 194 based on the levels of EN_OUTPUT and CMN_SRC_EN. These control signals are applied to the gates of the corresponding transistors to turn the transistors OFF and ON as described.

When operating as a current regulator, transistors 191, 192, 197, and 198 do not conduct, i.e., are not enabled. Transistor 183 acts as a master that controls the operation of slave transistor 184 by controlling V_GATE_SW. Thus, transistors 183 and 184 may be viewed as a master transistor and a slave transistor, respectively, in a current mirror arrangement. V_GATE_SW turns transistor 184 ON and OFF to produce a regulated current output signal with a desired current level controlled by the level of the V_GATE signal.

The general operation of example circuit 180 as a current regulator is similar to the operation of example circuit 110 of FIG. 8. That is, example circuits 110 and 180 use a similar configuration incorporating a current mirror and active cascode. Example circuit 180 differs from example circuit 110 by using a different configuration for switching between operational modes. Rather than a bypass switch, circuit 180 employs an adaptable circuit that operates, in effect, as either a regulator or a switch on a selective basis. Transistors 183 and 184 form a current mirror, as mentioned above, and may be selected to be well matched to each other. Transistors 182 and 185-190 form an active cascode configuration that that protects transistor 184 from high voltages at SRC_OUT and monitors I_SUM so that the $V_{DS}$ of transistors 183 and 184 are approximately equal over the operational range of circuit 180.

In operation, REG_TOP decreases when delivering stimulation, thereby causing the voltage drop over transistors 182 and 184 to decrease proportionately. Because of this decrease, the $V_{DS}$ of transistor 182 decreases, causing transistor 186 to begin to turn OFF. This, in turn, causes the $V_{GS}$ of transistor 185 to increase and turn transistor 185 ON more, thereby decreasing the $V_{GS}$ of transistor 187. Consequently, transistor 187 begins to turn OFF, which causes the $V_{GS}$ of transistor 182 to increase. That is, transistor 187 replaces voltage on transistor 182, VG_CASC, causing its resistive value to decrease, thereby restoring voltage on drain-to-source voltage ($V_{DS}$) of transistor 184 so that it more closely matches the $V_{DS}$ of transistor 183.

Transistors 188-190 set the current for transistors 185-187 based on I_FDBK. I_FDBK is a reference current and may be generated by circuitry at a front end of example circuit 180. In particular, transistors 188 and 189 set the current for transistor 185 and transistor 190 sets the current for transistor 187. Also, similar to example circuits 110 and 130 in FIGS. 8 and 9, respectively, it is also contemplated that example circuit 180 may be implemented using other configurations, such as the configurations previously discussed with respect to FIGS. 10 and 11.

Again, in FIG. 14, transistor 182 may represent multiple, e.g., sixty-four (64), transistors coupled in parallel with each other that each receive VG_CASC on their respective gates. As an example, the output of transistor 182 may be approximately 100 μA, but the overall source current may be many times that value, as a result of summation of multiple, parallel regulated current branches. In addition, transistor 182 also may prevent high voltages from being applied to the output.

When circuit 180 switches from operating as a current regulator to a switch, transistors 191 and 192 are turned ON, and transistors 193 and 196 are turned OFF. Transistors 197 and 198 remain turned OFF. After transistors 193 and 196 are turned OFF for a period of time, transistors 197 and 198 are turned ON. This creates a non-overlapping clock generator which prevents the supply voltage from shorting through transistors 191, 193, and 197. Gate 195 controls transistor 194 to be off during regulated or unregulated modes. When either of the inputs (EN_OUTPUT or CMN_SRC_EN)_to gate 195 is high, the output of gate 195 is high, which turns off transistor 194, allowing the input to transistor 182 to be either driven low to ground via transistor 197 (causing transistor 182 to be driving as a switch in the unregulated mode) or to VG_CASC_BIAS via transistor 193 (as in the regulated mode). In some implementations, the signals EN_OUTPUT applied to gate 195 and nEN_OUTPUT applied to transistor 193 may be skewed in time slightly to implement a non-overlapping clock generator. In general, the signal nEN_OUTPUT is essentially the inverse of EN_OUTPUT except for the slight timing skew in some implementations.

In the unregulated mode, transistors 197 and 198 are turned ON to drive transistors 182 and 184, respectively, into saturation. Accordingly, SRC_OUT is coupled to the high reference voltage REG_TOP through transistors 182 and 184 and circuit 180 sources current based on the amount of current required to be delivered by the stimulation electrode given load conditions and current distribution at the stimulated tissue site adjacent the electrode. In this manner, circuit 180 can be configured to operate as either an unregulated current path or a regulated current path.

Circuit 180 is turned OFF when the corresponding electrode is inactive, i.e., not used in an electrode configuration for delivering stimulation therapy. Transistors 191, 192, 193, 194, and 196 are turned ON and transistors 197 and 198 are turned OFF when circuit 180 is turned OFF. When transistors 191 and 192 are turned ON, the active cascode (transistors 185-190) and transistor 183 are turned OFF.

Transistors 182-198 may be implemented as N-type and P-type MOSFET transistors configured to operate in a depletion mode. It should be understood, however, that circuit 180 may be implemented using various types and configurations of transistors. Because transistors 196, 197, and 198 in circuit 180 FIG. 14 are small in size compared to output transistor 182, circuit 180 may be made smaller in size than circuit 110 of FIG. 8 by eliminating additional switches and, therefore, may be more easily implemented with a smaller chip size.

Figure 15:
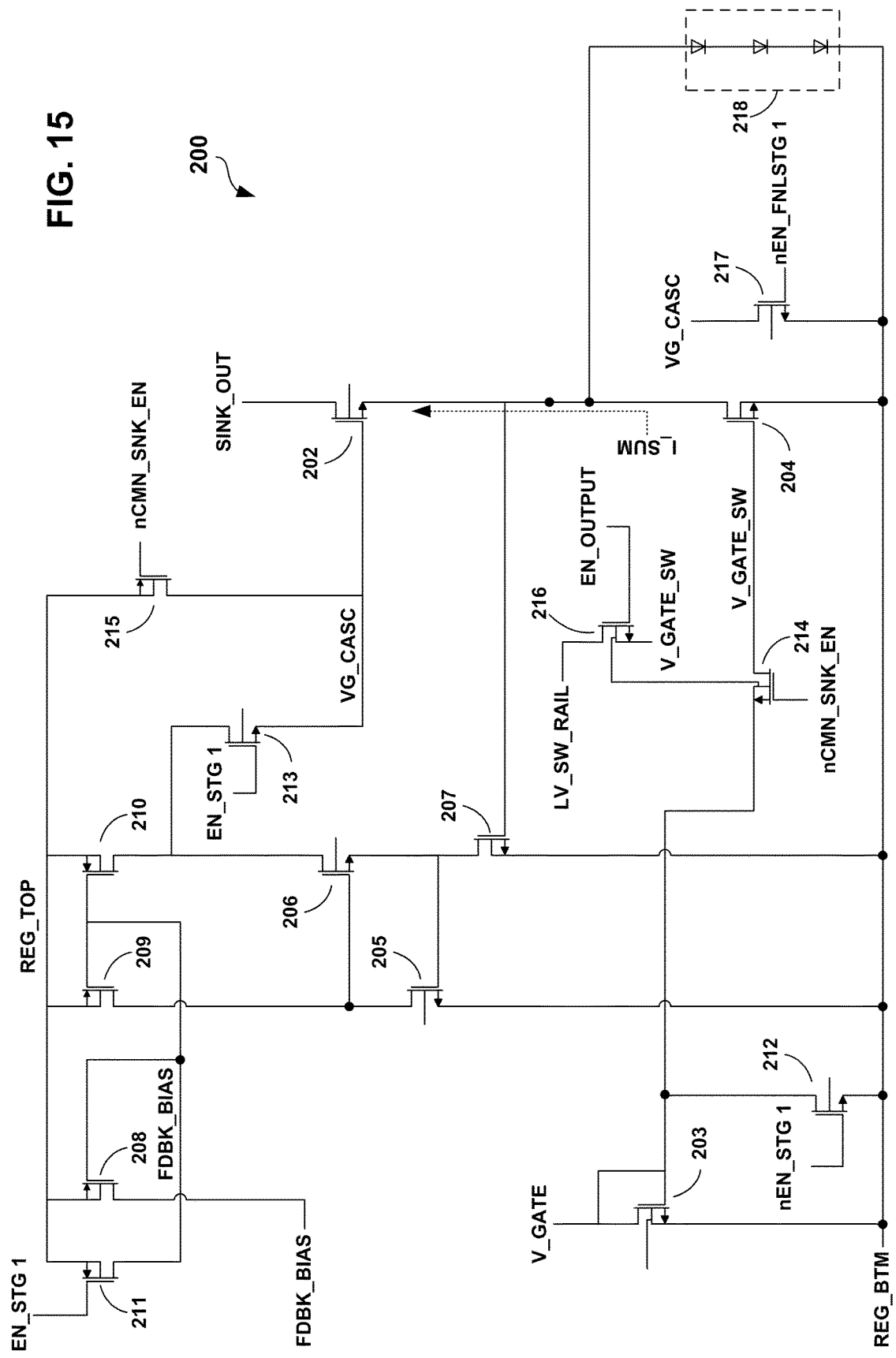

FIG. 15 is a circuit diagram illustrating an example circuit 200 that may be used to implement one of adaptable, regulated current sinks 156 shown in FIG. 12. Inputs to circuit 200 are REG_TOP, REG_BTM, V_GATE, FDBK_BIAS, EN_STG1, nEN_STG1, and CMN_SNK_EN, and VG_CASC, as well as BPLUS, nCMN_SNK_EN, and nEN_OUTPUT. REG_TOP, REG_BTM, V_GATE, FDBK_BIAS, and LV_SW_RAIL are supply inputs that drive elements of circuit 200. EN_STG1, nEN_STG1, CMN_SNK_EN, nCMN_SNK_EN, and nEN_ OUTPUT are logic inputs that are used to control the operation of circuit 200 as a current regulator or as a switch that couples a corresponding electrode to an unregulated low reference voltage, e.g., REG_BTM. As described with reference to circuit 110 of FIG. 8, for circuit 200 of FIG. 15, the adaptable current sink may represent a number of parallel, adaptable current sink branches that may be selectively activated to scale up or down to a desired current level as a percentage of a reference current. For example, each regulated current source may include 64 parallel current sink transistors (each like transistor 204), each providing $\frac{1}{64}^{th}$ of the reference current level. Circuit 200 shows one of these current sink transistors.

The logic inputs are also used to turn circuit 200 OFF when the corresponding electrode is not in use. Accordingly, transistors 211 and 212 may function as enable switches used to turn master transistors 208, 203, respectively, OFF and ON. Transistors 213 and 214 may function like isolation switches to selectively isolate transistors 202, 204 from the front end of the sink circuit. Transistors 215 and 216 may function as reference switches that bias transistors 202, 204 during unregulated mode. The isolation transistors 213, 214 and reference transistors 215, 216 may be operated in a coordinated manner to selectively operate the adaptable current sink as a regulated current sink or as a switch that couples the corresponding electrode to a reference voltage via an unregulated current path. In particular, isolation transistors 213, 214 and reference transistors 215, 216 may function to selectively tie transistors 202, 204 into the current mirror and activate cascode circuitry for regulated current delivery, or separate transistors 203, 204 from such circuitry for unregulated current delivery from REG_BTM. The output of circuit 200 is SNK_OUT and is applied to a corresponding electrode.

REG_TOP and REG_BTM are positive and negative voltages supplied as reference voltages. V_GATE is an analog input signal with desired stimulation parameters supplied by stimulation control module 62 when circuit 200 operates as a current regulator. Stimulation control module 62 may not supply V_GATE to circuit 200 when circuit 200 is operating as a switch or is not in use.

The following provides a description of the operation of circuit 200 as a current regulator and as a switch. The timing waveforms for the control signals are provided in FIGS. 16A and 16B. When operating as a current regulator and, more specifically, as a regulated current sink, transistors 211, 212, 215, and 216 are turned OFF and transistors 213 and 214 are turned ON. In this configuration, transistor 203 controls the operation of transistor 204 by controlling the gate voltage of transistor 204, V_GATE_SW. This turns transistor 2040N and OFF to produce a regulated current output signal with the desired signal parameters set by input signal V_GATE. Consequently, transistors 203 and 204 may be viewed as a master transistor and a slave transistor, respectively.

Example circuit 200 generally operates in a manner similar to circuit 130 in FIG. 9 with respect to operation as a regulated current sink. In particular, example circuit 200 also uses the previously described configuration that includes a current mirror with well matched transistors and a plurality of transistors operating as an active cascode configuration. Example circuit 200, however, is configured differently than example circuit 130 in FIG. 9 with respect to the additional transistors that are used for operating circuit 200 as a switch in an unregulated mode. Accordingly, transistors 203 and 204 may be configured to operate as a current mirror and selected to be well matched to each other, and transistors 202 and 205-210 may operate as an active cascode circuit that protects transistor 204 from high voltages at SINK_OUT and monitors I_SUM so that the $V_{DS}$ of transistor 203 and the $V_{DS}$ of 204 are approximately equal over the operational range of circuit 200.

In operation, REG_TOP decreases when delivering stimulation thereby causing the voltage drop over transistors 202 and 204 to decrease proportionately due to the decreased headroom of the bilateral circuit. Because of this decrease, the $V_{DS}$ of transistor 202 decreases causing transistor 207 to begin to turn OFF. This, in turn, causes the $V_{GS}$ of transistor 205 to increase and turn transistor 2050N more, thereby decreasing the $V_{GS}$ of transistor 206. Consequently, transistor 206 begins to turn OFF, which causes the $V_{GS}$ of transistor 202 to increase. That is, transistor 206 replaces voltage on transistor 202, VG_CASC, causing its resistive value to decrease, thereby restoring voltage on $V_{DS}$ of transistor 204.

Transistors 208-210 set the current for transistors 205-207 based on I_FDBK. I_FDBK is a reference current and may be generated by circuitry at the front end of example circuit 200. In particular, transistor 208 generates a $V_{GS}$ which is then applied to transistors 209 and 210. This then sets the current for transistor 205 and transistor 206, respectively, therapy causing transistors 209 and 210 to operate as current sources.

Similar to example circuits 110, 130, and 180 in FIGS. 8, 9, and 14, respectively, it is also contemplated that example circuit 200 may be implemented using other configurations, such as the configurations previously discussed with respect to FIGS. 8, 9, and 14.

When circuit 200 operates as a switch, transistors 211 and 212 are turned ON and transistors 213 and 214 are turned OFF. Transistors 214 and 216 may remain OFF for a period of time before being turned ON to prevent the supply voltage from shorting through transistors 216, 214 and 212. In this configuration, transistors 215 and 215 drive transistors 202 and 204 into saturation. This results in SNK_OUT being coupled to the low reference voltage REG_BTM through transistors 202 and 204 and circuit 200 sinks an amount of current based on the amount of current required to be sunk by the stimulation electrode given load conditions and current distribution at the stimulated tissue site adjacent the electrode. In this manner, circuit 200 can be configured to operate as either an unregulated current path or a regulated current path.

Circuit 200 may be turned OFF by turning ON transistors 211, 212, 214 and 217 and turning OFF transistors 213, 215 and 216. Turning ON transistors 211 and 212 turns OFF the active cascode transistors and the master transistor, i.e., transistors 205-210, and transistor 203, respectively. Transistor 217 serves to turn transistor 202 OFF when it is need to be in a high impedance state. Transistor 217 ties the gate (VG_CASC) of transistor 202 to ground, effectively turning transistor 202 OFF.

Transistors 202-217 may be implemented as N-type and P-type MOSFET transistors configured to operate in a depletion mode. It should be understood, however, that circuit 200 may be implemented using various types and configurations of transistors. Because transistors 213-217 are small in size compared to output transistor 202, circuit 200 may be smaller in size than a circuit 130 (FIG. 9) that includes additional switches and, therefore, more easily implemented with a reduced chip size.

Figure 16A:
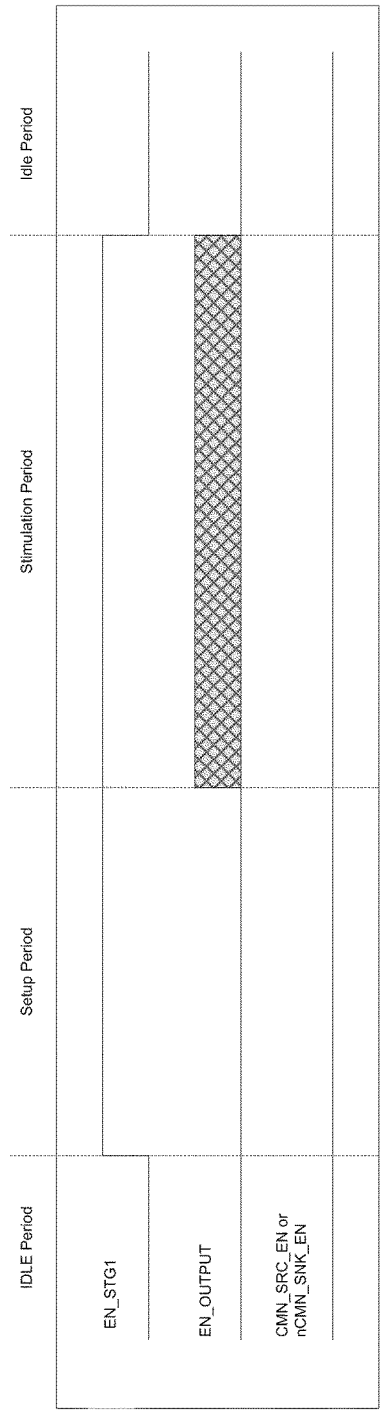
FIGS. 16A and 16B are timing waveforms for the example circuitry shown in FIGS. 14 and 15.
Figure 16B:
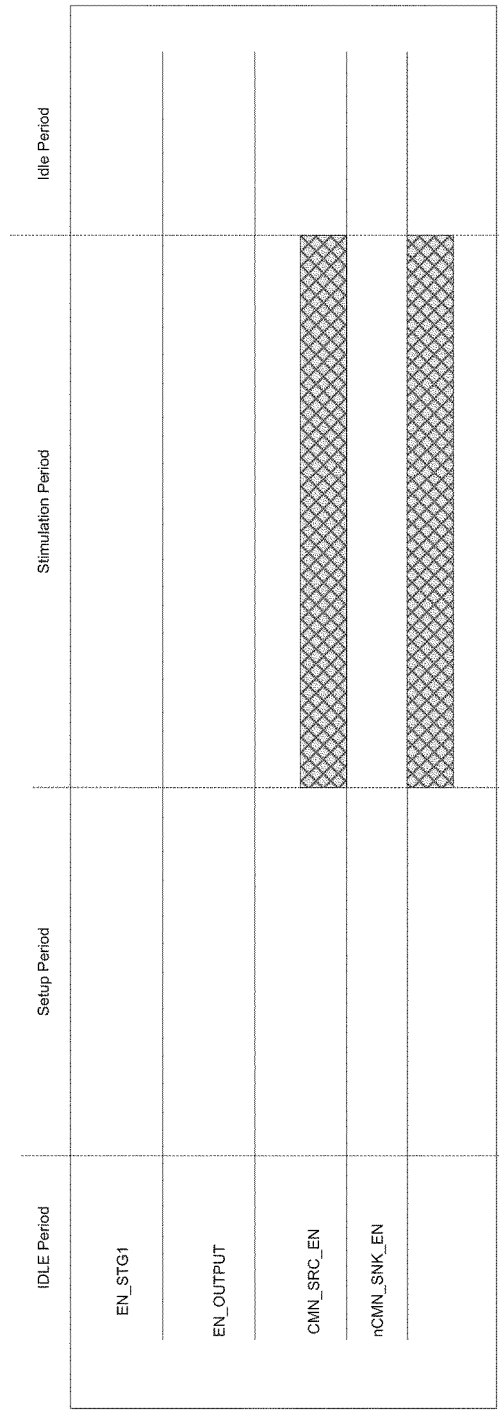

FIGS. 16A and 16B illustrate timing waveforms for example circuit 180 (FIG. 14) and example circuit 200 (FIG. 14) operating, respectively, in a regulated electrode mode and an unregulated electrode mode while delivering stimulation. The timing waveforms shown in FIGS. 10A and 10B include EN_STG1, EN_OUTPUT, and CMN_SRC_EN (circuit 180) or CMN_SNK_EN (circuit 200), as generated by stimulation control module 62. The timing waveforms for these signals are shown over a time period including an initial idle period, a setup period, a stimulation period, and a final idle period.

In particular, FIG. 16A illustrates timing waveforms for example circuits 180 and 200 delivering stimulation while operating in a regulated electrode mode. In the case of source circuit 180, FIG. 16A illustrates operation in a regulated anode mode. For sink circuit 200, FIG. 16B illustrates operation in a regulated cathode mode. During an initial idle period, all of the control signals are low and no signal is provided to the input or the output of example circuits 180 and 200.

EN_STG1 goes high over the setup period, turning ON the master transistors and active cascode transistors in example circuits 180 and 200. During the stimulation period, EN_STG1 stays high and EN_OUTPUT goes high over the stimulation period, according to a selected program or programs delivered by stimulation control module 62.

When EN_OUTPUT goes high, the active cascode transistors are coupled to the gate of the output transistor, i.e., transistors 185-190 are coupled to the gate of transistor 112 in circuit 182 (FIG. 14) and transistors 205-210 are coupled to the gate of transistor 202 in circuit 200 (FIG. 15). Thus, EN_OUTPUT turns ON the output transistor so that circuits 180 and 200 may source and sink current, respectively. Because EN_STG1 was high during the prior setup period, the signal controlling the output transistors may effectively turn the output transistor full ON at the beginning of the stimulation period. EN_STG1 and EN_OUTPUT return to a low value during the final idle period, effectively turning OFF current source circuit 180 or current sink circuit 200, as applicable.

FIG. 16B illustrates timing waveforms for example circuit 180 and 200 when operating in unregulated modes. FIG. 16B illustrates timing waveforms for example circuits 180 and 200 for delivering stimulation therapy while operating in an unregulated, reference mode. During the initial idle period and the setup period, EN_STG1, EN_OUTPUT, and CMN_SRC_EN (for source circuit 110) remain low, whereas nCMN_SNK_EN (for sink circuit 200) remains low. Again, the nCMN_SNK_EN label designates the inverse of CMN_SNK_EN. Over the stimulation period, CMN_SRC_EN (for source circuit 180) or nCMN_SNK_EN (for sink circuit 200) go to an active state to cause circuits 180 and 200 to deliver unregulated current from an unregulated high reference value (REG_TOP) for source circuit 180 and or to an unregulated low reference value (REG_BTM) for sink circuit 200, respectively, during a stimulation period.

For example, CMN_SRC_EN goes high during a stimulation period, while nCMN_SNK_EN goes low during a stimulation period. The CMN_SRC_EN and nCMN_SNK_EN signals cause circuits 130, 110, respectively, to deliver unregulated current for a specified stimulation period, according to a selected program or programs delivered by stimulation control module 62. The levels of CMN_SRC_EN or nCMN_SNK_EN returns to a low value or high value, respectively, during the final idle period to return to operation in an OFF mode.

FIGS. 17A-17C, 18A-18C, 19A, 19B, 20A, and 20B are conceptual diagrams illustrating example leads and electrode configurations that may be used for delivering electrical stimulation therapy in accordance with various examples described in this disclosure. It should be understood that the example leads and electrode configurations are merely illustrative and should not be considered limiting of the techniques broadly embodied and described in this disclosure. Rather, FIGS. 17A-17C, 18A-18C, 19A, 19B, 20A, and 20B illustrate a few examples of the many different electrode configurations that may be defined using regulated electrodes in combination with one or more unregulated reference electrodes.

In general, an implantable medical electrical lead may include one or more electrodes. Common lead configurations include leads with four, eight or sixteen electrodes, implanted alone or in combination with other leads. In some cases, one or more electrodes formed on housing of an implantable electrical stimulator may add to the number of electrodes that can be used to form electrode configurations.

Figure 17A:
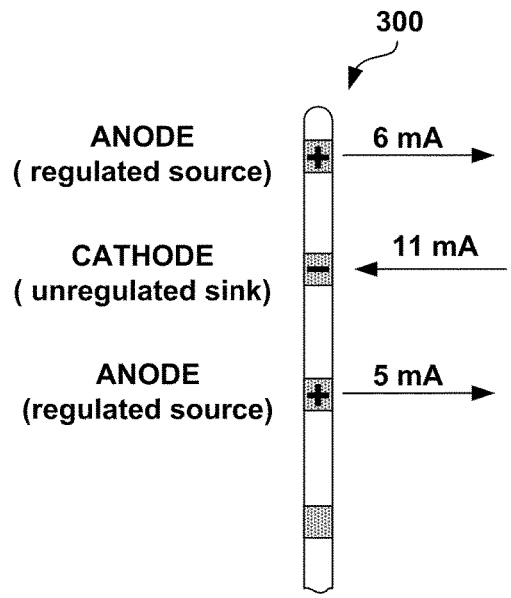
Figure 17B:
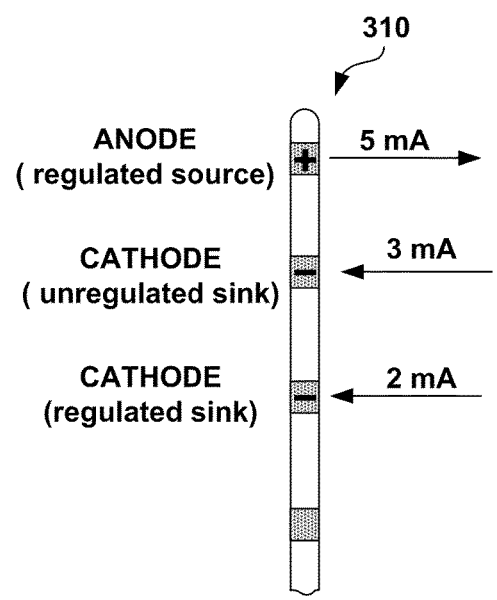
Figure 17C:
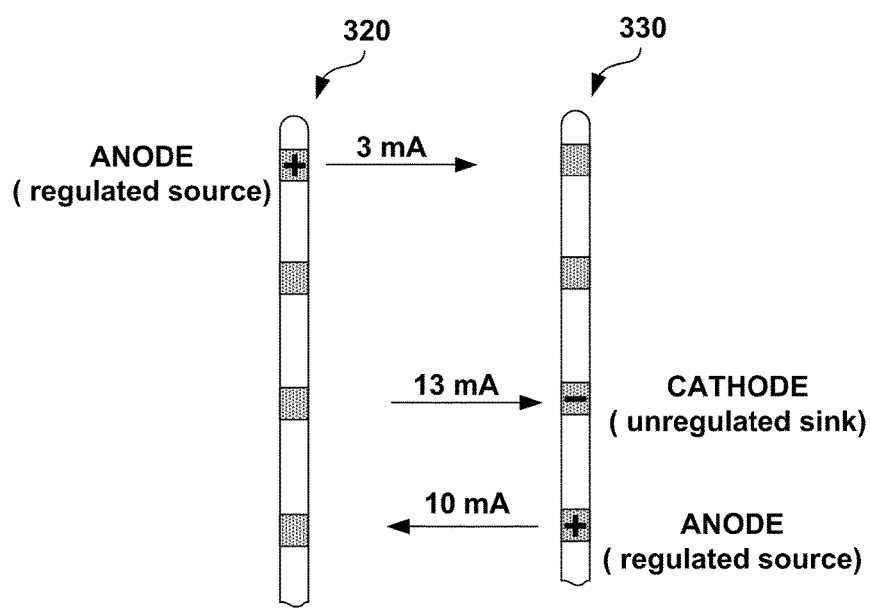

FIGS. 17A-C are conceptual diagrams that illustrate example leads that may be used for delivering constant current stimulation therapy using two or more regulated electrodes and an unregulated, reference electrode operating as an unregulated cathode to sink current to a reference voltage via an unregulated current path. The unregulated current sink in each of FIGS. 17A-C sinks approximately the sum of the stimulation current sourced and/or sunk by two regulated electrodes.

In the example of FIG. 17A, example lead 300 delivers stimulation using two regulated anodes, i.e., two regulated current sources, and an unregulated anode, i.e., an unregulated current sink. The terms anode and current source may be used interchangeably throughout the description. Similarly, the terms cathode and current sink may also be used interchangeably throughout the description.

A first regulated anode sources 6 milliamps (mA) of regulated current. A second regulated anode sources 5 mA of regulated current in the example of FIG. 17A. An unregulated cathode positioned between the regulated anodes along the length of the lead 300 sinks an amount of current approximately equal to the sum of the amounts of regulated current sourced by the regulated anodes, i.e., 11 mA. As shown in FIG. 17A, however, the 11 mA produced by the regulated anodes are sunk by the unregulated cathode to a reference voltage via an unregulated current path.

In the example of FIG. 17B, lead 310 delivers stimulation using a regulated cathode, a regulated anode, and an unregulated cathode. The unregulated cathode sinks approximately the difference between the stimulation current sourced by the regulated anode and sunk by the regulated cathode. In some examples, the regulated anode and cathode may source and sink substantially the same amount of current. In such examples, the unregulated cathode may sink a minimal amount of current or substantially none at all.

In general, it may be desirable to select the unregulated cathode to be the cathode, among all cathodes in the pertinent electrode configuration, that is assigned the highest current sink value. In the example of FIG. 17B, a regulated anode sources 5 mA of current, a regulated cathode sinks 2 mA of current, and an unregulated cathode sinks the difference, i.e., 3 mA of current, to a low reference voltage via an unregulated current path.

In the example of FIG. 17C, electrodes are provided on two leads 320 and 330 that may be implanted adjacent one another and configured to deliver stimulation. An electrical stimulation is programmed to source current via a regulated anode on lead 320, source current via a regulated anode on lead 330, and sink current via an unregulated cathode on lead 330. As shown in FIG. 17C, the regulated anode on lead 320 sources 3 mA of current, the regulated anode on lead 330 sources 10 mA of current, and the unregulated cathode on lead 330 sinks the sum of those currents, i.e., 13 mA.

FIGS. 18A-18C are conceptual diagrams illustrating additional example leads that may be used for delivering constant current stimulation therapy using two or more stimulation electrodes and a reference electrode operating as an unregulated current source (unregulated anode). The unregulated anode in each of FIGS. 18A-18C sources approximately the sum (or difference) of current produced by the regulated electrodes.

In the example of FIG. 18A, example lead 340 delivers stimulation using two regulated cathodes and an unregulated anode. More particularly, an electrical stimulator is programmed to deliver stimulation via selected electrodes in the manner described with reference to FIG. 18A. A first regulated cathode sinks 4 mA via a regulated current path, a second regulated cathode sinks 10 mA via a regulated current path, and a regulated anode sources the sum of those currents, i.e., 14 mA, via an unregulated current path from a reference voltage.

In the example of FIG. 18B, example lead 350 delivers stimulation using a regulated anode, a regulated cathode, and an unregulated anode. In the configuration of FIG. 18B, the unregulated anode may be selected as the anode with the lowest current source value among the other anodes forming the electrode configuration. In FIG. 18B, the unregulated anode sources approximately 3 mA from a reference voltage via an unregulated current path. The 3 mA sourced by the unregulated anode is the difference between the 4 mA sourced by the regulated anode and the 8 mA sunk by the regulated cathode in the configuration of FIG. 18B.

In the example of FIG. 18C, example lead 360 carries an unregulated anode and example lead 370 carries a regulated cathode and a regulated anode. Again, the unregulated cathode may be selected as the anodes that sources the least amount of current compared to other anodes in the specified electrode configuration. The unregulated anode on lead 360 sources 9 mA of current, which is equal to the difference between the 22 mA sunk by the regulated cathode and the 13 mA sourced by the regulated anode on lead 370.

FIGS. 19A and 19B are conceptual diagrams illustrating example leads that may be used for delivering constant current stimulation using a common cathode ring configuration, where the unregulated cathodes form a ring that surrounds the regulated anodes. In FIGS. 19A and 19B, leads 380 and 390 each include eight electrodes. In the example of FIG. 19A, two of the electrodes are programmed as regulated anodes (indicated by plus signs) and two of the electrodes are programmed as unregulated cathodes (indicated by minus signs). Inactive electrodes are not indicated by plus or minus signs. The regulated anodes (+) are positioned between the unregulated cathodes (−) and are located substantially adjacent to each other. The unregulated cathodes are positioned on opposite sides of the regulated anodes.

The common cathode ring configuration of FIG. 19A may be used to steer the stimulation field by adjusting the current values for each of the regulated anodes. The regulated anodes source 9 mA and 3 mA of current, respectively. Each of the unregulated cathodes sinks part of the amount of current sourced by the common anodes. The unregulated cathode adjacent the upper regulated anode sinks 9 mA, while the unregulated cathode adjacent the lower regulated anode sinks 3 mA.

Although the unregulated cathodes are shown in FIG. 19A as sinking specific amounts of current, 9 mA and 3 mA, for purposes of illustration, it should be understood that the amount of current that is sunk by each of unregulated cathodes may vary because the anodes are unregulated current sinks. The amount of current received by each of the unregulated anodes may depend on various factors, such as the resistive properties of tissue surrounding the leads, proximity of the respective anodes and cathodes, and other factors. In any case, the unregulated cathodes together may sink approximately the amount of current sourced by the regulated anodes positioned between them.

In the example of FIG. 19B, example lead 390 includes four electrodes programmed as regulated anodes (+) and two electrodes programmed as unregulated cathodes (−). The regulated anodes are positioned between the unregulated cathodes. Again, the regulated anodes may be programmed to steer the stimulation field. Because the cathodes are unregulated, adjusting the stimulation field only requires reprogramming the amounts of current delivered by the regulated anodes since the unregulated cathodes may automatically sink approximately the amount of current sourced by the regulated cathodes.

In FIG. 19B, regulated anodes are clustered together among the third through sixth electrodes from the bottom of the lead, and source 5 mA, 5 mA, 20 mA and 20 mA, respectively. For purposes of example only, the upper unregulated cathode is shown as sinking 40 mA, while the lower unregulated cathode is shown as sinking 10 mA. Other unregulated sink amounts are possible. Notably, programming can be simplified with unregulated cathodic sinks as the unregulated sinks do not require reprogramming when the regulated anodic currents need to be reprogrammed. Instead, the unregulated cathodes simply sink whatever unbalanced charge is produced in the circuit defined by the electrode configuration.

FIG. 19C is a conceptual diagram illustrating an example paddle lead 392 that may be used for delivering constant current stimulation using a common anode ring configuration, where the unregulated anodes form a ring that surrounds the regulated cathodes. In the example of FIG. 19C, lead 392 includes a lead body 394 and a lead paddle section 395 carrying an array of electrodes 396 arranged in three rows having five, six and five electrodes, respectively. Electrodes indicated by plus (+) signs are unregulated anodes, electrodes indicated by minus (−) signs are regulated cathodes, and electrodes without signs are inactive electrodes.

The unregulated anodes are shaded in FIG. 19C to highlight a ring formed by the unregulated anodes around the regulated cathodes. Although two regulated cathodes surrounded by a ring of eight unregulated anodes are shown in FIG. 19C, other numbers of anodes and cathodes may be used in various implementations and electrode configurations. In addition, paddle lead 392 may be configured to include lesser or greater numbers of electrodes. In some implementations, paddle lead 392 may be similar to the Specify™ 5-6-5 paddle lead commercially available from Medtronic, Inc. of Minneapolis, Minn.

FIGS. 20A and 20B are conceptual diagrams illustrating example leads that may be used for delivering constant current stimulation using a common anode pool configuration. In the example of FIG. 20A, example lead 400 includes eight electrodes. Two of the electrodes are programmed as unregulated anodes (+) and two of the electrodes are programmed as regulated cathodes (−). As in FIGS. 19A-19C, electrodes that do not include plus (+) or minus (−) signs are inactive electrodes. The unregulated anodes (+) are positioned between the regulated cathodes and are located substantially adjacent to each other. Each regulated cathode (−) is positioned generally adjacent one of the unregulated anodes.

The common anode pool configuration of FIG. 20A may be used to steer the stimulation field by adjusting the current values for each of the two or more regulated cathodes. However, there is no need to adjust any current values for the anodes, as they are unregulated, and respond to source whatever current is required to be sunk by the regulated cathodes. Each of the unregulated anodes sources part of the amount of current that the regulated cathodes sink. As shown in FIG. 20A, for example, one regulated cathode sinks 5 mA and the other regulated cathodes sinks 10 mA. In this case, the unregulated anodes source approximately a sum of the current sunk by the regulated cathodes, e.g., 15 mA. For example, an upper anode may source 5 mA and the lower anode may source 10 mA, each from a reference voltage via a respective, unregulated current path.

In the example of FIG. 20B, example lead 410 includes four electrodes programmed as unregulated anodes (+) and two electrodes programmed as regulated cathodes (−). Similar to FIG. 20A, in FIG. 20B, the unregulated anodes are positioned between the regulated cathodes. Again, the unregulated anodes and regulated cathodes may be programmed to steer the stimulation field. The current amounts illustrated in FIGS. 20A and 20B are merely exemplary and should not be considered limiting. Rather, the depicted amounts of current merely illustrate how a stimulation field may be steered by programming the regulated cathodes.

In the example of FIG. 20B, the upper regulated cathode sinks 20 mA and the lower regulated cathode sinks 8 mA. The unregulated anodes (+) source approximately a sum of the sink currents, i.e., 28 mA. More particularly, in this example, the unregulated anodes source 15 mA, 5 mA, 2 mA, and 6 mA of current. The stimulation field or pattern created by the current delivered via the electrode configuration may be steered, shifted or shaped by simply adjusting the regulated cathode currents, and without the need to provide any reprogramming of the unregulated anodes.

FIG. 20C is a conceptual diagram illustrating an example paddle lead 412 that may be used for delivering constant current stimulation using a common cathode pool configuration, where regulated anodes (+) form a ring that surrounds the unregulated cathodes (−). In the example of FIG. 19C, lead 412 includes a lead body 414 and a lead paddle section 416 carrying an array of electrodes 416 arranged in three rows having five, six and five electrodes, respectively. Electrodes indicated by plus (+) signs are regulated anodes, electrodes indicated by minus (−) signs are unregulated cathodes, and electrodes without signs are inactive electrodes.

The unregulated cathodes are shaded in FIG. 20C to highlight a pool formed by the unregulated cathodes within the ring of regulated anodes. Although two unregulated cathodes surrounded by a ring of eight regulated anodes are shown in FIG. 20C, other numbers of anodes and cathodes may be used in various implementations and electrode configurations. In addition, paddle lead 412 may be configured to include lesser or greater numbers of electrodes. In some implementations, paddle lead 412 may be similar to the Specify™ 5-6-5 paddle lead commercially available from Medtronic, Inc. of Minneapolis, Minn.

Figure 21:
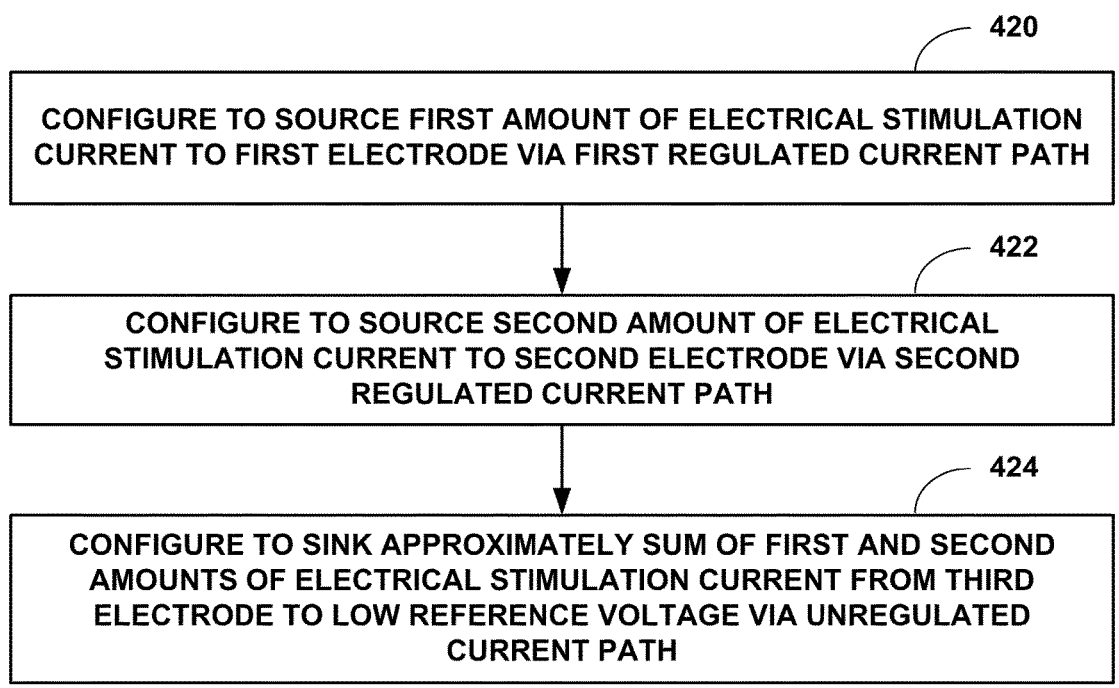
FIGS. 21-23 are flow diagrams illustrating methods that may be performed by an implantable stimulator, as described in this disclosure.
Figure 22:
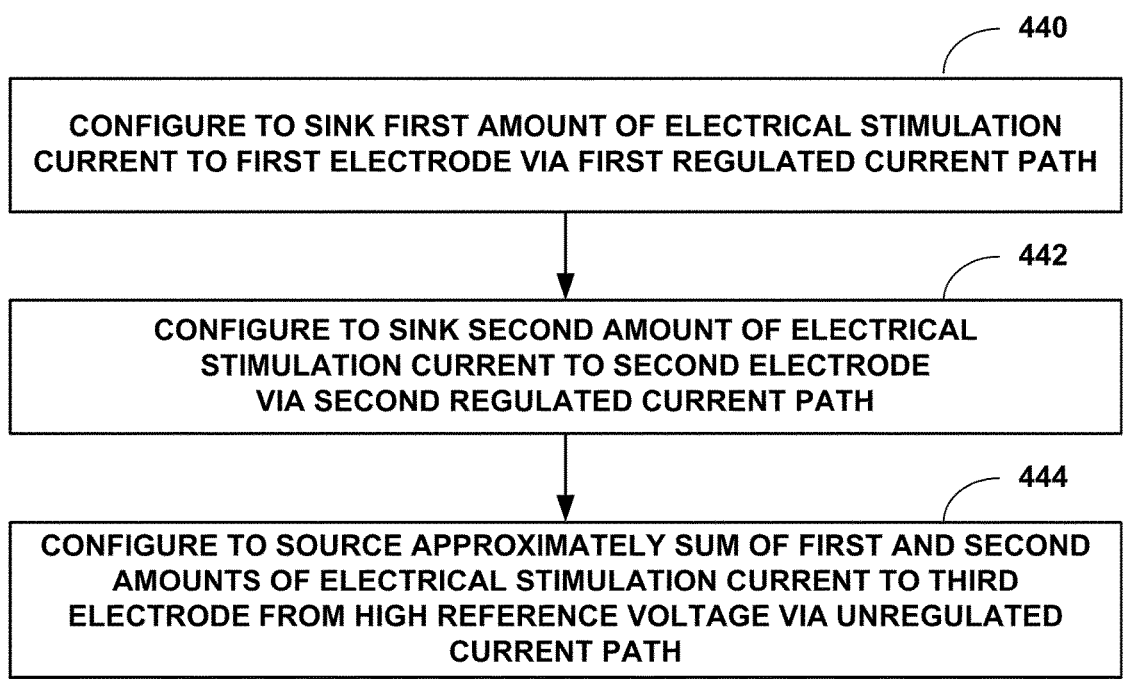
Figure 23:
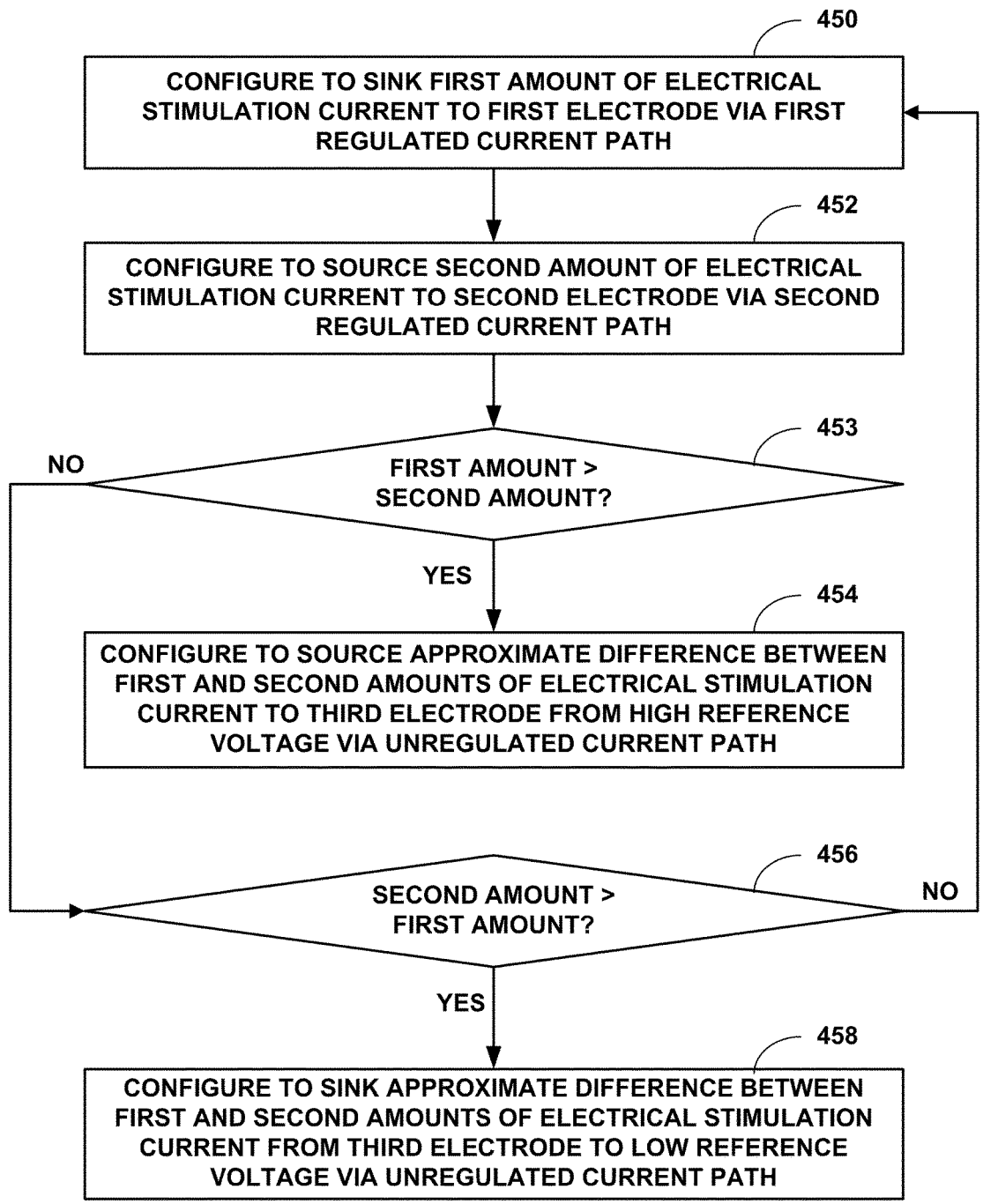

FIGS. 21-23 are flow diagrams illustrating methods that may be performed by an implantable stimulator, such as implantable stimulator 4 or implantable stimulator 34, for delivering constant current stimulation to the patient using electrode configurations comprising one or more regulated electrodes and one or more unregulated electrodes. At least some of the operations shown in FIGS. 21-23 are presented as operations that may be performed simultaneously. Accordingly, the order in which the operations are presented in FIGS. 21-23 does not necessarily indicate a temporal order in which the operations are performed. Instead, FIGS. 21-23 generally present the functions that may be performed by an implantable stimulator simultaneously to configure the stimulator to use different combinations of regulated and unregulated electrodes for delivery of stimulation current. Implantable stimulators 4 and 34 have been described as being configured with a stimulation generator 60A or 60B. An implantable stimulator configured with stimulator generator 60A may be referred to as a switchable implantable stimulator. An implantable stimulator configured with stimulation generator 60B may be referred to as an adaptable stimulation generator. The methods illustrated in FIGS. 26-29 may be performed by a switchable implantable stimulator or an adaptable implantable stimulator. For ease of illustration, and purposes of example, the methods illustrated in FIGS. 21-23 will be described with reference to implantable stimulator 4, although implantable stimulator 34, or other stimulators may be used to perform such methods.

In the example of FIG. 21, stimulator 4 is configured to source a first amount of electrical stimulation current to a first electrode via a first regulated current path (420), and source a second amount of electrical stimulation current to a second electrode via a second regulated current path (422). The first and second electrodes may also be referred to as regulated anodes. When implemented as a switchable implantable stimulator, implantable stimulator 4 may source the first and second amounts of electrical stimulation current via respective regulated current sources. In contrast, when implemented as an adaptable implantable stimulator, stimulator 4 may source the first and second amounts of electrical stimulation via respective adaptable current sources selected to operate as regulated current sources. As further shown in FIG. 21, implantable stimulator 4 is configured to sink approximately the sum of the first and second amounts of electrical stimulation current from a third electrode to a low reference voltage via an unregulated current path (424). The stimulation current may be delivered via the first, second and third electrodes as continuous stimulation waveforms or stimulation pulses.

In accordance with terminology used in this description, the third electrode may also be referred to as an unregulated cathode. In this way, implantable stimulator 4 delivers balanced constant current stimulation to patient 6 via a combination of regulated and unregulated electrodes. In particular, in FIG. 21, implantable stimulator 4 delivers current via two regulated anodes and one unregulated cathode. The configuration of stimulator 4 to use one or more unregulated electrodes may provide increased battery life since operation of circuitry for regulating the current at the third electrode, the unregulated electrode, is not required. Implantable stimulator 4 may use a switch to couple the third electrode to the low reference voltage via an unregulated current path when implemented as a switchable implantable stimulator. When implemented as an adaptable implantable stimulator, however, implantable stimulator 4 may selectively control the operation of an adaptive current sink coupled to the third electrode to operate as a switch that connects the third electrode to the low reference voltage via an unregulated current path.

FIG. 22 illustrates another example method that may be performed by implantable stimulator 4 for configuring the stimulator to deliver constant current stimulation therapy to patient 6. In general, implantable stimulator 4 uses this method for selecting electrodes to deliver current using two regulated cathodes and an unregulated cathode. As shown in FIG. 21, implantable stimulator 4 is configured to sink a first amount of electrical stimulation current to a first electrode via a first regulated current path (440). Implantable stimulator 4 also is configured to sink a second amount of electrical stimulation current to a second electrode via a second regulated current path (442). In order to balance the current, implantable stimulator 4 is configured to also source approximately the sum of the first and second amounts of electrical stimulation current to a third electrode from a high reference voltage via an unregulated current path (444).

When implemented as a switchable implantable stimulator, implantable stimulator 4 may sink the first and second amounts of electrical stimulation current using respective regulated current sinks, and use a switch to couple the third electrode to the high reference voltage while deactivating regulated current sources and sinks also coupled to the third electrode. In contrast, when implemented as an adaptable implantable stimulator, stimulator 4 may sink the first and second amounts of electrical stimulation using respective adaptable current sinks selected to operate as regulated current sinks, and source the sum of the first and second amounts of electrical stimulation current using a corresponding adaptable current sink selected to operate as a switch that connects the third electrode to the high reference potential.

FIG. 23 is another example method that may be performed by implantable stimulator 4 to configure the stimulator for delivering constant current stimulation therapy to patient 6. In general, in the example of FIG. 23, implantable stimulator 4 is configured to deliver stimulation current using a regulated anode, a regulated cathode, and an unregulated anode or cathode, depending on whether the difference between the source regulated current and the sunk regulated current is positive or negative. As shown in FIG. 23, implantable stimulator 4 is configured to sink a first amount of electrical stimulation current to a first electrode via a first regulated current path (450). Implantable stimulator 4 also is configured to source a second amount of electrical stimulation current to a second electrode via a second regulated current path (452).

Implantable stimulator 4 is configured to source or sink approximately the sum (or net difference) of the first and second amounts of electrical stimulation current via a third electrode. In particular, if the first amount of sunk regulated current (−i1) is greater than the second amount of sourced regulated current (+i2) (453) (e.g., −i1+i2 equals−idifference), then the third, unregulated electrode may be configured as an unregulated anode that sources current equal to an approximate difference between the first and second amounts of electrical stimulation current from a high reference voltage via an unregulated current path (454).

If the second amount of sourced regulated current (+i2) is greater than the first amount of sunk regulated current (−i1) (456) (e.g., +i2−i1=+idifference), then the third, unregulated electrode may be configured as an unregulated cathode that sinks current equal to an approximate difference between the first and second amounts of stimulation current from the third electrode to a low reference voltage via an unregulated current path (458). If the first and second amounts are equal, then there is no current unbalance, and the current distribution can be delivered by the regulated anode and regulated cathode without the need for an unregulated anode or unregulated cathode to source or sink significant amounts of current.

If the second amount of sourced regulated current is equal to the first amount of sunk regulated current, as indicated by the NO branches from decisions 453 and 456, then the first and second amounts of current offset each other. In this case, the third electrode would be inactive, e.g., as indicated by the return of the NO branch from decision 456 to block 450. This effective zero source or sink current can happen if the user is adjusting one of the regulated outputs up or down, which may cause the unregulated electrode to switch from an unregulated sink to an unregulated source. Alternatively, the third electrode could be configured to be active to be coupled to a reference voltage such as a low reference voltage via an unregulated current path but sink or source substantially zero current as long as the first and second amounts of current offset one another and do not produce a current. In this case, there would still be three active electrodes, as may be intended by a user, even though the current sourced or sunk by one of the electrodes may be at or near zero.

In practice, programming of electrode configurations, including selection of regulated and unregulated anodes and cathodes, and specification of pertinent sink and source currents, may be performed via a programming device or automatically by a stimulator. The programming device may provide various features for automation of electrode selection and specification of current amounts. In some cases, the programming device, which may be an external programmer such as the programmer shown in FIG. 4, may specify all electrode configurations and parameter values based on user input, and download such electrode configurations and values to the implantable stimulator, e.g., stimulator 4 or 34, as program data.

For example, program data for a particular stimulation program may specify a reference source current, a reference sink current, and percentages of the source or sink currents to be carried by selected electrodes. In addition, the program data may indicate which of the selected electrodes are coupled to regulated current paths and which of the selected electrodes are coupled to unregulated current paths. Upon user entry of reference source and sink currents, and assignment of percentages to selected electrodes, the programmer may automatically specify whether selected electrodes are coupled to regulated and unregulated current paths. In other examples, the programmer may specify basic electrode configurations and values, such as selected electrodes, reference currents, and current percentages, but permit the implantable stimulator to assign regulated or unregulated current paths to the selected electrodes.

As an illustration, it will be assumed that programming is generally automated within a programmer, without limitation as to implementations in which one or more aspects of such programming may be performed in the implantable stimulator. In the case of automated programming within the programmer, a physician, technician or other user may wish to specify a particular electrode configuration, including applicable source and sink currents for selected electrodes, e.g., by specifying reference source and sink currents and assigning percentages of such reference current to selected electrodes. The user may specify other parameters for a stimulation program.

For example, a physician may define a program in which sink or source stimulation currents are delivered with selected pulse widths, rates, and current amplitudes (e.g., expressed as percentages of reference currents) via a selected set of electrodes. If the physician specifies, for example, an electrode configuration in which a first electrode sources first current at a level of 8 mA, a second electrode sources second current at a level of 5 mA, and a third electrode sinks the sum of the first and second currents at a level of 13 mA, the programmer may be configured to automatically program the implantable stimulator to configure the first electrode as a regulated anode, the second electrode as a regulated anode, and the third electrode as an unregulated cathode, e.g., by selectively switching or adapting various regulated current sources or sinks as described in this disclosure. In this case, the physician may or may not need to select which electrode functions as the unregulated electrode. Instead, in a cathodic reference example, the programmer may automatically select, as the unregulated electrode, the cathode that is specified as carrying the largest current sink level, among one or more cathodes in the electrode configuration.

In another example, for an anodic reference, if the physician specifies, for example, an electrode configuration in which a first electrode sources first current at a level of 8 mA, a second electrode sinks second current at a level of 12 mA, and a third electrode sources the difference between the first and second currents at a level of 4 mA, the programmer may be configured to automatically program the implantable stimulator to configure the first electrode as an regulated anode, the second electrode as a regulated cathode, and the third electrode as an unregulated anode, e.g., by selectively switching or adapting various regulated current sources or sinks as described in this disclosure. In this case, the programmer may automatically select the anode carrying the smallest anodic current to be the unregulated electrode.

When configuring electrodes, e.g., as shown in FIG. 23, with a regulated sink electrode and a regulated source electrode, an unregulated electrode may be configured as a source or sink electrode depending on the difference between the regulated source and sink currents. In general, if the regulated source current is greater than the regulated sink current, an unregulated sink electrode will be provided. In this case, there are two cathodes, one of which is regulated and the other of which is unregulated. If the regulated source current is less than the regulated sink current, an unregulated source electrode will be provided. In this case, there are two anodes, one of which is regulated and the other of which is unregulated. If there are two cathodes, a default may be to program the cathode with the highest current value as the unregulated cathode.

If the regulated cathode is out of regulation, i.e., the current regulator coupled to the regulated cathode does not deliver current according to one or more required current regulator specifications, then the out of regulation cathode may be reconfigured to be the unregulated cathode and the other cathode may be reconfigured to be a regulated cathode. If this change still results in an out of regulation condition, then the existing configuration can be retained while the voltage source for the current regulator is increased. Upon increasing the voltage source level, the configuration process may be repeated if an out of regulation condition occurs.

Conversely, if there are two anodes, a default may be to program the anode with the lowest current value as the unregulated anode. If the regulated anode is out of regulation, i.e., the current regulator coupled to the regulated anode does not deliver current according to one or more required current regulator specifications, then the out of regulation anode may be reconfigured to be the unregulated anode and the other anode may be reconfigured to be a regulated anode. If this change still results in an out of regulation condition, then the existing configuration can be retained while the voltage source for the current regulator is increased. Upon increasing the voltage source level, the configuration process may be repeated if an out of regulation condition occurs.

Set forth below in Table 1 is a set of example scenarios illustrating selection of unregulated current paths in different electrode configurations. Such scenarios may represent selections by a user or automatic selections within a programmer or implantable stimulator to select regulated or unregulated current paths for particular electrodes included in specified electrode configurations. Table 1 reflects different scenarios in which either a common anode or common cathode scheme has been selected by a user or otherwise specified for an electrode configuration.

TABLE 1

| Electrode Configuration | Scheme | Reg/Unreg Selection |
| --- | --- | --- |
| 1 (10 mA), 2 (−6 mA), 3 (−4 mA) | Common Cathode | 1 (Reg), 2 (Unreg), 3 (Reg) |
| 1 (4 mA), 2 (−10 mA), 3 (6 mA) | Common Anode | 1 (Unreg), 2 (Reg), 3 (Reg) |
| 1 (5 mA), 2 (6 mA), 3 (−11 mA) | Common Anode | 1 (Unreg), 2 (Reg), 3 (Reg) |
| 1 (−5 mA), 2 (11 mA), 3 (−6 mA) | Common Cathode | 1 (Reg), 2 (Reg), 3 (Unreg) |

In Table 1, the electrode configuration column indicates source and sink current levels for selected electrodes, the scheme column indicates whether the common cathode or common anode scheme has been selected, and the reg/unreg selection column indicates assignments of the electrodes from the first column to regulated or unregulated current paths. As indicated in Table 1, in general, if the common cathode mode is selected, the unregulated current path may be assigned to the electrode that is assigned the largest sink current, i.e., electrode 2, as indicated in the first row of Table 1. The second row indicates a common anode scenario in which the unregulated current path may be assigned to the electrode with the smallest source current, i.e., electrode 1. The third row indicates another common anode scenario in which the unregulated current path is assigned to the electrode with the smallest source current, i.e., electrode 1. The fourth row indicates a common cathode scenario in which the unregulated current path is assigned to the electrode having the largest sink value, i.e., electrode 3.

The ability to program an implantable stimulator 4 or 34 to use one or more unregulated anodes or cathodes in combination with regulated anodes or cathodes may provide one or more advantages. As an example, an implantable stimulator that uses one or more unregulated electrodes may exhibit decreased power consumption and increased battery life by reducing the number of electrodes that are required to be current regulated. Increased battery life may be achieved because current regulator circuitry can be turned OFF for electrodes operating as unregulated current sources or sinks. In this manner, the power consumption overhead associated with at least some of the regulated current sources or sinks can be reduced or eliminated.

In addition, the use of unregulated electrodes may enhance current carrying capacity for a given number of electrodes by providing a direct unregulated current path between unregulated electrodes and a reference voltage. The unregulated electrode may sum currents from multiple regulated electrodes and direct them to or from the reference voltage via a switch or other connection that provides increased current capacity. Use of unregulated electrodes also may simplify stimulation field configuration and programming as unregulated electrodes generally do not require reprogramming when current levels and polarities are reprogrammed for regulated electrodes. Selective adaptation of a current source or sink to configure an electrode as a regulated electrode or unregulated electrode supports flexibility to provide precise current control or voltage compliance, as needed. An adaptable current source or sink, in some implementations, may eliminate the need for a separate switch for unregulated operation, thereby avoiding increased size, complexity and cost that may be associated with incorporation of such a switch.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various embodiments of the disclosure have been described. These and other embodiments are within the scope of the following claims.

The invention claimed is:

1. A device for delivering electrical nerve, muscle, or brain tissue stimulation therapy to a patient, the device comprising:
    a plurality of implantable electrodes;
    a regulated current source path;
    a regulated current sink path;
    an unregulated current path; and
    a stimulation generator comprising a stimulation controller configured to couple a first electrode of the plurality of electrodes to a regulated current source of the regulated current source path to deliver electrical stimulation current to the patient for delivering the electrical nerve, muscle, or brain tissue stimulation therapy to the patient, couple a second electrode of the plurality of electrodes to a regulated current sink of the regulated current sink path to deliver the electrical stimulation current to the patient for delivering the electrical nerve, muscle, or brain tissue stimulation therapy to the patient, and couple a third electrode of the plurality of electrodes to a reference voltage of the unregulated current path via a switch to deliver the electrical stimulation current to the patient for delivering the electrical nerve, muscle, or brain tissue stimulation therapy to the patient, wherein the reference voltage comprises a low reference voltage when the unregulated current path sinks current and a high reference voltage when the unregulated current path sources current, and wherein the stimulation generator is configured to deliver the electrical nerve, muscle, or brain tissue stimulation therapy to the patient by delivering the electrical stimulation current to the patient via a combination of the electrodes that includes the first electrode, the second electrode, and the third electrode.

2. The device of claim 1, further comprising one or more implantable leads, wherein each of the electrodes is located on a respective one of the one or more leads.

3. The device of claim 1, wherein the stimulation generator is further configured to:

deliver a first amount of the electrical stimulation current via the regulated current source path;

deliver a second amount of the electrical stimulation current via the regulated current sink path; and deliver a third amount of the electrical stimulation current via the unregulated current path, the third amount of the electrical stimulation current being approximately equal to a difference between the first and second amounts of the electrical stimulation current.

4. The device of claim 3, wherein:

the regulated current source sources the first amount of the electrical stimulation current via the regulated current source path, the regulated current sink sinks the second amount of the electrical stimulation current via the regulated current sink path, the second amount of the electrical stimulation current is less than the first amount of the electrical stimulation current, the unregulated current path sinks the third amount of the electrical stimulation current to the reference voltage, and the third amount of the electrical stimulation current is greater than the second amount of the electrical stimulation current.

5. The device of claim 3, wherein:

the regulated current source sources the first amount of the electrical stimulation current via the regulated current source path, the regulated current sink sinks the second amount of the electrical stimulation current via the regulated current sink path, the second amount of the electrical stimulation current is less than the first amount of the electrical stimulation current, the unregulated current path sinks the third amount of the electrical stimulation current to the reference voltage, and the reference voltage required to produce the unregulated sink current is less than another voltage required to produce the regulated sink current.

6. The device of claim 3, wherein:

the regulated current sink sinks the second amount of the electrical stimulation current via the regulated current sink path, the regulated current source sources the first amount of the electrical stimulation current via the regulated current source path, the first amount of the electrical stimulation current is less than the second amount of the electrical stimulation current, the unregulated current path sources the third amount of the electrical stimulation current from the reference voltage, and the third amount of the electrical stimulation current is greater than the first amount of the electrical stimulation current.

7. The device of claim 3, wherein:

the regulated current sink sinks the second amount of the electrical stimulation current via the regulated current sink path, the regulated current source sources the first amount of the electrical stimulation current via the regulated current source path, the first amount of the electrical stimulation current is less than the second amount of the electrical stimulation current, the unregulated current path sources the third amount of the electrical stimulation current from the reference voltage, and the reference voltage required to produce the third amount of the electrical stimulation current is greater than another voltage required to produce the first amount of the electrical stimulation current.

8. The device of claim 3, wherein the regulated current source path comprises a plurality of parallel regulated current source paths, the regulated current sink path comprises a plurality of parallel regulated current sink paths, and the unregulated current path comprises a plurality of parallel unregulated current paths.

9. The device of claim 1, wherein the unregulated current path is a first unregulated current path, wherein the device further comprises a second unregulated current path, wherein the stimulation controller is further configured to couple a fourth electrode of the plurality of electrodes to the second unregulated current path, and wherein the third and fourth electrodes are positioned between the first and second electrodes along the length of one or more implantable leads.

10. The device of claim 1, wherein the unregulated current path is a first unregulated current path, wherein the device further comprises a second unregulated current path, wherein the stimulation controller is further configured to couple a fourth electrode of the plurality of electrodes to the second unregulated current path, and wherein the first and second electrodes are positioned between the third and fourth electrodes along the length of one or more implantable leads.

11. The device of claim 1, wherein the stimulation controller is configured to couple a fourth electrode of the plurality of electrodes to a regulated current path.

12. The device of claim 1,
wherein the regulated current source is one of a plurality of regulated current sources and the regulated current sink is one of a plurality of regulated current sinks, and
wherein at least one of the electrodes of the plurality of electrodes is configurable by the stimulation controller to be electrically coupled to one of the regulated current sources, electrically coupled to one of the regulated current sinks, electrically coupled to the high reference voltage, or electrically coupled to the low reference voltage.

13. The device of claim 1, wherein a current level sourced or sunk by the unregulated current source path varies with different impedance load conditions.

14. The device of claim 1,
wherein the regulated current source is one of a plurality of regulated current sources and the regulated current sink is one of a plurality of regulated current sinks,
wherein at least one of the plurality of electrodes is configurable by the stimulation controller to be electrically coupled to one of the regulated current sources, electrically coupled to one of the regulated current sinks, electrically coupled to the high reference voltage, or electrically coupled to the low reference voltage,
wherein each respective regulated current source of the plurality of regulated current sources comprises a respective first plurality of transistors arranged in an active cascode configuration to control an amount of current coupled to the at least one of the electrodes when the respective regulated current source is coupled to the at least one of the electrodes, and
wherein each respective regulated current sink of the plurality of regulated current sinks comprises a respective second plurality of transistors arranged in an active cascode configuration to control an amount of current coupled to the at least one of the electrodes when the respective regulated current sink is coupled to the at least one of the electrodes.

15. The device of claim 1, wherein the stimulation controller is further configured to deliver the electrical stimulation current to the patient via the first electrode, the second electrode, and the third electrode as part of an electrical stimulation program.

16. The device of claim 1, wherein the electrical nerve, muscle, or brain tissue stimulation therapy comprises at least one of deep brain stimulation (DBS) therapy, cortical stimulation (CS) therapy, spinal cord stimulation (SCS) therapy, peripheral nerve stimulation (PNS) therapy, peripheral nerve field stimulation (PNFS) therapy, pelvic floor stimulation therapy, peripheral nerve stimulation therapy, and gastric stimulation therapy.

17. A method for delivering electrical nerve, muscle, or brain stimulation therapy to a patient, the method comprising:
coupling, with a stimulation controller, a first electrode of a plurality of electrodes implanted within the patient to a regulated current source path to deliver electrical stimulation current to the patient for delivering the electrical nerve, muscle, or brain tissue stimulation therapy to the patient, wherein coupling the first electrode to the regulated current source path comprises coupling the first electrode to a regulated current source;
coupling, with the stimulation controller, a second electrode of the plurality of electrodes implanted within the patient to a regulated current sink path to deliver the electrical stimulation current to the patient for delivering the electrical nerve, muscle, or brain tissue stimulation therapy to the patient, wherein coupling the second electrode to the regulated current sink path comprises coupling the second electrode to a regulated current sink;
coupling, with the stimulation controller, a third electrode of the plurality of electrodes implanted within the patient to an unregulated current path to deliver the electrical stimulation current to the patient for delivering the electrical nerve, muscle, or brain tissue stimulation therapy to the patient, wherein coupling the third electrode to an unregulated current path comprises coupling the third electrode to a reference voltage via a switch, and wherein the reference voltage comprises a low reference voltage when the unregulated current path sinks current and a high reference voltage when the unregulated current path sources current; and
delivering the electrical nerve, muscle, or brain tissue stimulation therapy to the patient by delivering the electrical stimulation current to the patient via a combination of the electrodes that includes the first electrode, the second electrode, and the third electrode.

18. The method of claim 17, wherein each of the electrodes is located on a respective one of one or more leads implanted within the patient.

19. The method of claim 17, wherein delivering the electrical nerve, muscle, or brain tissue stimulation therapy comprises:
delivering a first amount of the electrical stimulation current via the regulated current source path;
delivering a second amount of the electrical stimulation current via the regulated current sink path; and
delivering a third amount of the electrical stimulation current via the unregulated current path, the third amount of the electrical stimulation current being approximately equal to a difference of the first and second amounts of the electrical stimulation current.

20. The method of claim 19, wherein the first amount of the electrical stimulation current is a regulated source current, the second amount of the electrical stimulation current is a regulated sink current less than the regulated source current, and the third amount of the electrical stimulation current is an unregulated sink current that is equal to approximately a difference between the regulated source current and the regulated sink current, wherein the unregulated sink current is greater than the regulated sink current.

21. The method of claim 19, wherein the first amount of the electrical stimulation current is a regulated source current, the second amount of the electrical stimulation current is a regulated sink current less than the regulated source current, and the third amount of the electrical stimulation current is an unregulated sink current that is equal to approximately a difference between the regulated source current and the regulated sink current, wherein the reference voltage required to produce the unregulated sink current is less than another voltage required to produce the regulated sink current.

22. The method of claim 19, wherein the second amount of the electrical stimulation current is a regulated sink current, the first amount of the electrical stimulation current is a regulated source current less than the regulated sink current, and the third amount of the electrical stimulation current is an unregulated source current that is equal to approximately a difference between the regulated sink current and the regulated source current, wherein the unregulated source current is greater than the regulated source current.

23. The method of claim 19, wherein the second amount of the electrical stimulation current is a regulated sink current, the first amount of the electrical stimulation current is a regulated source current less than the regulated sink current, and the third amount of the electrical stimulation current is an unregulated source current that is equal to approximately a difference between the regulated sink current and the regulated source current, wherein the reference voltage required to produce the third amount of current is greater than another voltage required to produce the first amount of the electrical stimulation current.

24. The method of claim 19, wherein the regulated current source path comprises a plurality of parallel regulated current source paths, the regulated current sink path comprises a plurality of parallel regulated current sink paths, and the unregulated current path comprises a plurality of parallel unregulated current paths.

25. The method of claim 17,
wherein the unregulated current path is a first unregulated current path,
wherein the method further comprises coupling a fourth electrode of the plurality of electrodes to a second unregulated current path, and
wherein the third and fourth electrodes are positioned between the first and second electrodes along the length of one or more implanted leads.

26. The method of claim 17,
wherein the unregulated current path is a first unregulated current path,
wherein the method further comprises coupling a fourth electrode of the plurality of electrodes to a second unregulated current path, and
wherein the first and second electrodes are positioned between the third and fourth electrodes along the length of one or more implanted leads.

27. The method of claim 17, wherein the method further comprises:
coupling a fourth electrode of the plurality of electrodes to a regulated current path.

28. The method of claim 17, wherein the regulated current source is one of a plurality of regulated current sources and the regulated current sink is one of a plurality of regulated current sinks, and at least one of the electrodes of the plurality of electrodes is configurable by the stimulation controller to be electrically coupled to one of the regulated current sources, electrically coupled to one of the regulated current sinks, electrically coupled to the high reference voltage, or electrically coupled to the low reference voltage.
selectively coupling the at least one of the plurality of electrodes to the regulated current source via the regulated current source path, the regulated current sink via the regulated current sink path, the first reference voltage via the unregulated current source path, or the second reference voltage via the unregulated sink path.

29. The method of claim 17,
wherein a current level sourced or sunk by the unregulated current path varies with different impedance load conditions.

30. The method of claim 17,
wherein the regulated current source is one of a plurality of regulated current sources and the regulated current sink is one of a plurality of regulated current sinks,
wherein at least one of the plurality of electrodes is configurable by the stimulation controller to be electrically coupled to one of the regulated current sources, electrically coupled to one of the regulated current sinks, electrically coupled to the high reference voltage, or electrically coupled to the low reference voltage,
wherein each respective regulated current source of the plurality of regulated current sources comprises a respective first plurality of transistors arranged in an active cascode configuration to control an amount of current coupled to the at least one of the plurality of electrodes when the respective regulated current source is coupled to the at least one of the electrodes, and
wherein each respective regulated current sink of the plurality of regulated current sinks comprises a respective second plurality of transistors arranged in an active cascode configuration to control an amount of current coupled to the at least one of the electrodes when the respective regulated current sink is coupled to the at least one of the plurality of electrodes.

31. The method of claim 17, further comprising:
delivering the electrical stimulation current to the patient via the first electrode, the second electrode, and the third electrode as part of an electrical stimulation program.

32. The method of claim 17, wherein the electrical nerve, muscle, or brain tissue stimulation therapy comprises at least one of deep brain stimulation (DBS) therapy, cortical stimulation (CS) therapy, spinal cord stimulation (SCS) therapy, peripheral nerve stimulation (PNS) therapy, peripheral nerve field stimulation (PNFS) therapy, pelvic floor stimulation therapy, peripheral nerve stimulation therapy, and gastric stimulation therapy.

33. A device for delivering electrical nerve, muscle, or brain tissue stimulation therapy to a patient, the device comprising:
means for coupling, via a regulated current source, a first electrode of a plurality of implantable electrodes to a regulated current source path to deliver electrical stimulation current to the patient for delivering the electrical nerve, muscle, or brain tissue stimulation therapy to the patient;
means for coupling, via a regulated current sink, a second electrode of the plurality of implantable electrodes implanted within the patient to a regulated current sink path to deliver the electrical stimulation current to the patient for delivering the electrical nerve, muscle, or brain tissue stimulation therapy to the patient;
means for coupling, via a reference voltage and a switch, a third electrode of the plurality of implantable electrodes to an unregulated current path to deliver the electrical stimulation current to the patient for delivering the electrical nerve, muscle, or brain tissue stimulation therapy to the patient, wherein the reference voltage comprises a low reference voltage when the unregulated current path sinks current and a high reference voltage when the unregulated current path sources current; and
means for delivering the electrical nerve, muscle, or brain tissue stimulation therapy to the patient by delivering the electrical stimulation current to the patient via a combination of the implantable electrodes that includes the first electrode, the second electrode, and the third electrode.

34. The device of claim 33, further comprising one or more implantable leads, wherein each of the electrodes is located on a respective one of the one or more leads.

35. The device of claim 33, wherein the means for delivering the electrical nerve, muscle, or brain tissue stimulation therapy comprises:
  means for delivering a first amount of the electrical stimulation current via the regulated current source path;
  means for delivering a second amount of the electrical stimulation current via the regulated current sink path; and
  means for delivering a third amount of the electrical stimulation current via the unregulated current path, the third amount of the electrical stimulation current being approximately equal to a difference between the first and second amounts of the electrical stimulation current.

36. The device of claim 35, wherein the first amount of the electrical stimulation current is a regulated source current, the second amount of the electrical stimulation current is a regulated sink current less than the regulated source current, and the third amount of the electrical stimulation current is an unregulated sink current that is equal to approximately a difference between the regulated source current and the regulated sink current, wherein the unregulated sink current is greater than the regulated sink current.

37. The device of claim 35, wherein the first amount of the electrical stimulation current is a regulated source current, the second amount of the electrical stimulation current is a regulated sink current less than the regulated source current, and the third amount of the electrical stimulation current is an unregulated sink current that is equal to approximately a difference between the regulated source current and the regulated sink current, wherein the reference voltage required to produce the unregulated sink current is less than another voltage required to produce the regulated sink current.

38. The device of claim 33, wherein the means for delivering the electrical stimulation therapy comprises:
  means for delivering a first amount of the electrical stimulation current via the regulated current source path;
  means for delivering a second amount of the electrical stimulation current via the regulated current sink path; and
  means for delivering a third amount of the electrical stimulation current via the unregulated current path.

39. The device of claim 38, wherein the second amount of the electrical stimulation current is a regulated sink current, the first amount of the electrical stimulation current is a regulated source current less than the regulated sink current, and the third amount of the electrical stimulation current is an unregulated source current that is equal to approximately a difference between the regulated sink current and the regulated source current, wherein the unregulated source current is greater than the regulated source current.

40. The device of claim 38, wherein the second amount of the electrical stimulation current is a regulated sink current, the first amount of the electrical stimulation current is a regulated source current less than the regulated sink current, and the third amount of the electrical stimulation current is an unregulated source current that is equal to approximately a difference between the regulated sink current and the regulated source current, wherein the reference voltage required to produce the unregulated sink current is less than another voltage required to produce the regulated sink current.

41. The device of claim 33, wherein the regulated current source is one of a plurality of regulated current sources and the regulated current sink is one of a plurality of regulated current sinks, and wherein at least one of the electrodes of the plurality of implantable electrodes is configurable by a stimulation controller to be electrically coupled to one of the regulated current sources, electrically coupled to one of the regulated current sinks, electrically coupled to the high reference voltage, or electrically coupled to the low reference voltage.

42. The device of claim 33, wherein the electrical nerve, muscle, or brain tissue stimulation therapy comprises at least one of deep brain stimulation (DBS) therapy, cortical stimulation (CS) therapy, spinal cord stimulation (SCS) therapy, peripheral nerve stimulation (PNS) therapy, peripheral nerve field stimulation (PNFS) therapy, pelvic floor stimulation therapy, peripheral nerve stimulation therapy, and gastric stimulation therapy.

43. A device for programming a medical electrical stimulator to deliver electrical nerve, muscle, or brain tissue stimulation therapy to a patient, the device comprising:
  a user interface configured to receive programming information from a user;
  a processor configured to define electrical stimulation programs based at least in part on the programming information; and
  a communication interface configured to communicate the programs to the medical electrical stimulator,
  wherein at least some of the electrical stimulation programs cause the medical electrical stimulator to generate electrical stimulation current for delivery to the patient via implantable electrodes, to couple a first electrode of the implantable electrodes to a regulated current source of a regulated current source path to deliver the electrical stimulation current to the patient for delivering the electrical nerve, muscle, or brain tissue stimulation therapy to the patient, to couple a second electrode of the implantable electrodes to a regulated current sink of a regulated current sink path to deliver the electrical stimulation current to the patient for delivering the electrical nerve, muscle, or brain tissue stimulation therapy to the patient, to couple a third electrode of the implantable electrodes to a reference voltage of an unregulated current path via a switch to deliver the electrical stimulation current to the patient for delivering the electrical nerve, muscle, or brain tissue stimulation therapy to the patient, and to deliver the electrical nerve, muscle, or brain tissue stimulation therapy to the patient by delivering the electrical stimulation current to the patient via a combination of the implantable electrodes that includes the first electrode, the second electrode, and the third electrode, wherein the reference voltage comprises a low reference voltage when the unregulated current path sinks current and a high reference voltage when the unregulated current path sources current.

44. The device of claim 43, wherein each of the electrodes is located on a respective one of one or more implantable leads.

45. The device of claim 43, wherein at least some of the electrical stimulation programs cause the electrical stimulator to deliver a first amount of the electrical stimulation current via the regulated current source path, deliver a second amount of the electrical stimulation current via the regulated current sink path, and deliver a third amount of the electrical stimulation current via the unregulated current path, the third amount of the electrical stimulation current being approximately equal to a difference between the first and second amounts of the electrical stimulation current.

46. The device of claim 45, wherein the programming information includes information defining the first amount of the electrical stimulation current delivered by the first electrode, the second amount of the electrical stimulation current delivered by the second electrode, and the third amount of the electrical stimulation current delivered by the third electrode, and the processor is configured to define, based on the programming information, an electrical stimulation program that causes the medical electrical stimulator to couple the first electrode to the regulated current source path, the second electrode to the regulated current sink path, and the third electrode to the unregulated current path.

47. The device of claim 43, wherein the electrical nerve, muscle, or brain tissue stimulation therapy comprises at least one of deep brain stimulation (DBS) therapy, cortical stimulation (CS) therapy, spinal cord stimulation (SCS) therapy, peripheral nerve stimulation (PNS) therapy, peripheral nerve field stimulation (PNFS) therapy, pelvic floor stimulation therapy, peripheral nerve stimulation therapy, and gastric stimulation therapy.

48. A non-transitory computer-readable storage medium comprising instructions that, when executed by a processor, cause the processor to:
couple a first electrode of a plurality of electrodes implanted within the patient to a regulated current source of a regulated current source path to deliver electrical stimulation current to the patient for delivering the electrical nerve, muscle, or brain tissue stimulation therapy to the patient;
couple a second electrode of the plurality of electrodes implanted within the patient to a regulated current sink of a regulated current sink path to deliver the electrical stimulation current to the patient for delivering the electrical nerve, muscle, or brain tissue stimulation therapy to the patient;
couple a third electrode of the plurality of electrodes implanted within the patient to a reference voltage of an unregulated current path via a switch to deliver the electrical stimulation current to the patient for delivering the electrical nerve, muscle, or brain tissue stimulation therapy to the patient, wherein the reference voltage comprises a low reference voltage when the unregulated current path sinks current and a high reference voltage when the unregulated current path sources current; and
deliver the electrical nerve, muscle, or brain tissue stimulation therapy to the patient by delivering the electrical stimulation current to the patient via a combination of the electrodes that includes the first electrode, the second electrode, and the third electrode.

49. The non-transitory computer-readable storage medium of claim 48, wherein each of the electrodes is located on a respective one of one or more leads implanted within the patient.

50. The non-transitory computer-readable storage medium of claim 48, wherein the instructions that, when executed by the processor, cause the processor to deliver the electrical nerve, muscle, or brain tissue stimulation therapy further comprise instructions that, when executed by the processor, cause the process to:
deliver a first amount of the electrical stimulation current via the regulated current source path;
deliver a second amount of the electrical stimulation current via the regulated current sink path; and
deliver a third amount of the electrical stimulation current via the unregulated current path, the third amount of the electrical stimulation current being approximately equal to a difference between the first and second amounts of the electrical stimulation current.

51. The non-transitory computer-readable storage medium of claim 50, wherein the first amount of the electrical stimulation current is a regulated source current, the second amount of the electrical stimulation current is a regulated sink current less than the regulated source current, and the third amount of the electrical stimulation current is an unregulated sink current that is equal to approximately a difference between the regulated source current and the regulated sink current, wherein the unregulated sink current is greater than the regulated sink current.

52. The non-transitory computer-readable storage medium of claim 50, wherein the first amount of the electrical stimulation current is a regulated source current, the second amount of the electrical stimulation current is a regulated sink current less than the regulated source current, and the third amount of the electrical stimulation current is an unregulated sink current that is equal to approximately a difference between the regulated source current and the regulated sink current, wherein the reference voltage required to produce the unregulated sink current is less than another voltage required to produce the regulated sink current.

53. The non-transitory computer-readable storage medium of claim 50, wherein the second amount of the electrical stimulation current is a regulated sink current, the first amount of the electrical stimulation current is a regulated source current less than the regulated sink current, and the third amount of the electrical stimulation current is an unregulated source current that is equal to approximately a difference between the regulated sink current and the regulated source current, wherein the unregulated source current is greater than the regulated source current.

54. The non-transitory computer-readable storage medium of claim 50, wherein the second amount of the electrical stimulation current is a regulated sink current, the first amount of the electrical stimulation current is a regulated source current less than the regulated sink current, and the third amount of the electrical stimulation current is an unregulated source current that is equal to approximately a difference between the regulated sink current and the regulated source current, wherein the reference voltage required to produce the third amount of current is greater than another voltage required to produce the first amount of the electrical stimulation current.

55. The non-transitory computer-readable storage medium of claim 50, wherein the regulated current source path comprises a plurality of parallel regulated current source paths, the regulated current sink path comprises a plurality of parallel regulated current sink paths, and the unregulated current path comprises a plurality of parallel unregulated current paths.

56. The non-transitory computer-readable storage medium of claim 48,
wherein the unregulated current path is a first unregulated current path,
wherein the non-transitory computer-readable storage medium further comprises instructions that, when executed by the processor, cause the processor to couple a fourth electrode of the plurality of electrodes to a second unregulated current path, and
wherein the third and fourth electrodes are positioned between the first and second electrodes along the length of one or more implanted leads.

57. The non-transitory computer-readable storage medium of claim 48, wherein the unregulated current path is a first unregulated current path, wherein the non-transitory computer-readable storage medium further comprises instructions that, when executed by the processor, cause the processor to couple a fourth electrode of the plurality of electrodes to a second unregulated current path, and wherein the first and second electrodes are positioned between the third and fourth electrodes along the length of one or more implanted leads.

58. The non-transitory computer-readable storage medium of claim 48, further comprising instructions that, when executed by the processor, cause the processor to:

couple a fourth electrode of the plurality of electrodes to a regulated current path.

59. The non-transitory computer-readable storage medium of claim 48, wherein the regulated current source is one of a plurality of regulated current sources and the regulated current sink is one of a plurality of regulated current sinks, and wherein at least one of the electrodes of the plurality of electrodes is configurable by a stimulation controller to be electrically coupled to one of the regulated current sources, electrically coupled to one of the regulated current sinks, electrically coupled to the high reference voltage, or electrically coupled to the low reference voltage.

60. The non-transitory computer-readable storage medium of claim 48, wherein the electrical nerve, muscle, or brain tissue stimulation therapy comprises at least one of deep brain stimulation (DBS) therapy, cortical stimulation (CS) therapy, spinal cord stimulation (SCS) therapy, peripheral nerve stimulation (PNS) therapy, peripheral nerve field stimulation (PNFS) therapy, pelvic floor stimulation therapy, peripheral nerve stimulation therapy, and gastric stimulation therapy.

* * * * *